United States Patent
Bonnemann et al.

(10) Patent No.: US 11,655,470 B2
(45) Date of Patent: May 23, 2023

(54) DIAGNOSING COL6-RELATED DISORDERS AND METHODS FOR TREATING SAME

(71) Applicants: THE USA, AS REPRESENTED BY THE SECRETARY, DEPT. OF HEALTH AND HUMAN SERVICES, Bethesda, MD (US); MURDOCH UNIVERSITY, Perth (AU); THE GENERAL HOSPITAL CORPORATION, Boston, MA (US); PRESIDENT AND FELLOWS OF HARVARD COLLEGE, Cambridge, MA (US); UCL BUSINESS PLC, London (GB)

(72) Inventors: Carsten G. Bonnemann, Washington, DC (US); Veronique Bolduc, Rockville, MD (US); Francesco Muntoni, London (GB); Steve Wilton, Applecross (AU); Daniel Macarthur, Cambridge, MA (US); Monkol Lek, Braintree, MA (US); Beryl Cummings, Brookline, MA (US)

(73) Assignee: The USA, as represented by the Secretary, Dept. of Health and Human Services, Bethesda, MD (US)

( * ) Notice: Subject to any disclaimer, the term of this patent is extended or adjusted under 35 U.S.C. 154(b) by 0 days.

(21) Appl. No.: 16/315,278

(22) PCT Filed: Jul. 5, 2017

(86) PCT No.: PCT/US2017/040726
§ 371 (c)(1),
(2) Date: Jan. 4, 2019

(87) PCT Pub. No.: WO2018/009547
PCT Pub. Date: Jan. 11, 2018

(65) Prior Publication Data
US 2019/0367917 A1 Dec. 5, 2019

Related U.S. Application Data

(60) Provisional application No. 62/358,482, filed on Jul. 5, 2016.

(51) Int. Cl.
*C12N 15/113* (2010.01)
*C12N 15/86* (2006.01)
*C12Q 1/6883* (2018.01)

(52) U.S. Cl.
CPC ............ *C12N 15/113* (2013.01); *C12N 15/86* (2013.01); *C12Q 1/6883* (2013.01); *C12N 2310/11* (2013.01); *C12N 2310/3233* (2013.01); *C12N 2320/33* (2013.01); *C12N 2800/60* (2013.01); *C12Q 2600/156* (2013.01)

(58) Field of Classification Search
CPC .. C12N 15/113; C12N 15/86; C12N 2310/11; C12N 2310/3233; C12N 2320/33; C12N 2800/60; C12N 15/111; C12Q 1/6883; C12Q 2600/156; C12Q 1/6886
See application file for complete search history.

(56) References Cited

U.S. PATENT DOCUMENTS

| | | | |
|---|---|---|---|
| 5,888,750 A | 3/1999 | Vanmaele et al. | |
| 6,001,567 A | 12/1999 | Brow et al. | |
| 6,043,031 A | 3/2000 | Koster et al. | |
| 6,045,996 A | 4/2000 | Cronin et al. | |
| 6,068,818 A | 5/2000 | Ackley et al. | |
| 6,806,084 B1 | 10/2004 | Debs et al. | |
| 8,569,256 B2 | 10/2013 | Heyes et al. | |
| 8,765,703 B2 | 7/2014 | Vickers et al. | |
| 8,946,183 B2 | 2/2015 | Baker et al. | |
| 9,303,076 B2 | 4/2016 | Brinkmann et al. | |
| 2005/0255487 A1* | 11/2005 | Khvorova | C12Y 502/01008 435/6.16 |
| 2012/0270254 A1 | 10/2012 | Liao et al. | |
| 2013/0059901 A1 | 3/2013 | Bauer et al. | |
| 2014/0275212 A1 | 9/2014 | van Deutekom | |
| 2015/0141320 A1* | 5/2015 | Krieg | A61K 31/7088 514/1.1 |
| 2015/0238627 A1 | 8/2015 | Leger et al. | |
| 2015/0361428 A1 | 12/2015 | Bestwick et al. | |
| 2015/0376615 A1 | 12/2015 | Wilton et al. | |

FOREIGN PATENT DOCUMENTS

WO   WO 99/67641   12/1999
WO   WO 00/39587   7/2000

OTHER PUBLICATIONS

Van Deutekom et al (Hum. Mol. Gen. 10(15):1547-1554, 2001) (Year: 2001).*
Aartsma-Rus et al (Neuromuscular Disorders 12: S71-S77, 2002) (Year: 2002).*
Mann et al (J. Gene Med. 4(6):644-54, 2002) (Year: 2002).*
(Continued)

*Primary Examiner* — Richard A Schnizer
(74) *Attorney, Agent, or Firm* — Tracey S. Truitt; Armstrong Teasdale LLP

(57) ABSTRACT

A single nucleotide polymorphism (SNP) that results in development of a Type VI collagen, alpha 1 chain-related disorder, and the use of the SNP to identify individuals at risk for developing COL6-related disorders (COL6-RD). Also provided are antisense oligomers for treating individuals at risk for developing COL6-RD, as well as methods for screening compounds for their potential as therapeutic agents.

8 Claims, 18 Drawing Sheets

Specification includes a Sequence Listing.

(56) References Cited

OTHER PUBLICATIONS

Arechavala-Gomeza et al (Hum. Gene Ther. Sep. 2007;18(9):798-810) (Year: 2007).*
Aartsma-Rus et al (Mol. Ther. 17(3): 548-553, 2009) (Year: 2009).*
Wu et al (PLoS One 6(5): 12 pages, 2011) (Year: 2001).*
International Search Report and Written Opinion prepared by the U.S. Patent and Trademark Office dated Oct. 6, 2017, for International Application No. PCT/US2017/040726.
International Preliminary Report on Patentability for International (PCT) Patent Application No. PCT/US2017/040726, dated Jan. 17, 2019 9 pages.
Berger et al. "Universal bases for hybridization, replication and chain termination," Nucleic Acids Research, Aug. 2000, vol. 28, No. 15, pp. 2911-2914.
Bustin "Absolute quantification of mRNA using real-time reverse transcription polymerase chain reaction assays," Journal of Molecular Endocrinology, Oct. 2000, vol. 25, No. 2, pp. 169-193.
Oldenburg et al. "New Cleavase® Fragment Length Polymorphism Method Improves the Mutation Detection Assay," BioTechniques, Feb. 2000, vol. 28, No. 2, pp. 351-357.
Olivier "The Invader® assay for SNP genotyping," Mutation Research, Jun. 2005, vol. 573, No. 1-2, pp. 103-110 (abstract only).
Peat et al. Variable penetrance of COL6A1 null mutations: Implications for prenatal diagnosis and genetic counselling in Ullrich congenital muscular dystrophy families, Neuromuscular Disorders, 2007, vol. 17, pp. 547-557.

* cited by examiner

C.

DIAGNOSING COL6-RELATED DISORDERS AND METHODS FOR TREATING SAME

CROSS REFERENCE TO RELATED APPLICATIONS

This application is a national stage application under 35 U.S.C. 371 and claims the benefit of PCT Application No. PCT/US2017/040726 having an international filing date of 5 Jul. 2017, which designated the United States, which PCT application claimed the benefit of U.S. Provisional Patent Application No. 62/358,482 filed 5 Jul. 2016, the disclosure of each of which are incorporated herein by reference.

REFERENCE TO SEQUENCE LISTING

This application contains a Sequence Listing submitted as an electronic text file named "6137NINDS-2-PCT_sequence_listing_ST25.txt", having a size in bytes of 34 KB, and created on Jul. 5, 2017. The information contained in this electronic file is hereby incorporated by reference in its entirety pursuant to 37 CFR § 1.52(e)(5).

TECHNOLOGICAL FIELD

This disclosure relates to identifying individuals at risk of developing, or who have, a COL6A1-related disorder such as Ullrich muscular dystrophy, by detecting a specific nucleotide substitution in the gene encoding the alpha 1 chain of Type VI collagen. It also relates to the use of antisense oligonucleotides for treating individuals having such nucleotide substitution.

BACKGROUND

Collagen type VI is an important component of the extracellular matrix and plays crucial roles in organizing the matrix, and in supporting cell adhesion and survival. Type VI collagen is abundant predominantly in muscle, tendon and skin, tissues where collagen VI dysfunction may have important clinical sequelae. Collagen VI is produced from three independent genes, COL6A1, COL6A2 and COL6A3, each encoding an alpha chain essential for forming the collagen VI monomer, the basic unit of this complex protein. Three additional collagen VI genes have been identified in recent years (COL6A4, COL6A5, and COL6A6), although their importance is unknown at this time. The three alpha chains ($\alpha$1, $\alpha$2, and $\alpha$3), which share a similar structure, namely a triple helical (TH) domain composed of the Gly-X-Y repeated motif flanked by two globular domains, come together starting at the C-terminal end of the TH domain, and assemble, in a zipper-like fashion, through hydrogen bonding mediated by the glycine residues. Two monomers assemble to form antiparallel dimers, and subsequently tetramers, and these quaternary structures are stabilized by disulfur bridges from critical cysteine residues present in the TH domains. Tetramers are secreted in the extracellular space, where they unite end-to-end to form microfibrils. Residues in globular domains of the three chains are important for these interactions. In muscle, collagen VI microfibrils are located at the interface of the extracellular matrix and the myofibers basement membrane, from where they bind to other constituents of these networks, such as collagen type IV and biglycan. The main sources of collagen VI in muscle are the interstitial fibroblasts, as opposed to the muscle fibers themselves.

Mutations in any of the three main collagen VI genes (COL6A1, COL6A2 and COL6A3) are responsible for a number of neuromuscular disorders, collectively referred as collagen VI-related disorders (COL6-RD), that are now considered part of a spectrum rather than as distinct disorders. Ullrich muscular dystrophy, on the severe end of the spectrum, manifests by progressive, early-onset muscle weakness, proximal joint contractures, distal joint hyperlaxity, and respiratory dysfunction. Ullrich patients never acquire the ability to walk, or are delayed and later lose ambulation. Respiratory insufficiency is also a critical aspect of the disease, as it can be life-threatening if not properly managed. Bethlem myopathy, which is on the mild end of the spectrum, also presents with muscle weakness, proximal joint contractures, and distal laxity, although moderate. It is an adult-onset disorder, usually not associated with loss of ambulation. In between Ullrich and Bethlem myopathy lie a series of intermediate phenotypes with different degrees of disease severity.

Col6-RD can be inherited as recessive or dominant, but are most commonly caused by de novo dominant-negative mutations that act by interfering at different stages of the assembly process of the collagen VI tetramer molecules. Mutations that prevent mutant monomers from assembling into dimers and tetramers should be associated with a milder phenotype, as only normal tetramers are secreted. Alternatively, mutations that can be carried up until the tetramers will have a strong dominant-negative effect, as the vast majority of tetramers will be dysfunctional in the extracellular space. The two main categories of dominant-negative mutations are glycine substitutions (in the Gly-X-Y motif of the TH domain), and in-frame exon deletions (or mutations resulting in in-frame exon skipping), occurring typically at the N-terminal end of the TH, and therefore being incorporated into monomers. These mutations usually result in mislocalization of collagen VI in the muscle tissue, and reduced collagen VI deposition and increased retention in the cultured fibroblasts.

Patients suffering from COL6-RD usually present with progressive muscle weakness and stiffness in the spine and joints. Following clinical assessment, a suspicion of COL6-RD can be confirmed in the laboratory through standard diagnosis tools including biochemical analyses (muscle biopsy and cultured fibroblasts immunostaining) and genetic testing. Targeted genetic testing by sequencing the cDNA of the triple helical domains of COL6A1, COL6A2 and COL6A3 efficiently detects most of the mutations, such as exon deletion and glycine substitution mutations. Despite the availability of such procedures, they fail to identify a mutational cause for a considerable number of patients who meet the clinical and biochemical criteria of COL6-RD. Such findings suggest that additional mutations in collagen VI, or other genes, exist and remain to be identified and/or associated with COL6-RD.

Currently no cure exists for COL6-RD. The main form of treatment is physiotherapy, the goal of which is to keep the muscles active and to prevent the formation of contractures. If scoliosis develops, a spine brace may help prevent further deterioration, and severe cases may need surgical correction. Finally, night-time breathing problems may occur, resulting in headaches, drowsiness, and loss of appetite and weight, and which requires the initiation of night time mechanical ventilatory support. Respiratory failure can then progress to require daytime mechanical ventilatory support.

It is clear that current methods of diagnosing and treating COL6-RD are insufficient. Moreover, the currently available treatments merely attempt to slow onset or worsening of the disease, and fail to provide a permanent cure. Thus, what is needed are improved methods for diagnosing and treating individuals at risk for, or who are suffering from, COL6-RD. The present application provides such methods and therapies, and offers other benefits as well.

SUMMARY

The inventors have discovered a mutation in intron 11 of the COL6A1 gene that alters splicing of COL6A1 pre-mRNA, and produces a mature alpha 1(VI) chain mRNA that comprises an additional exon. Translation of such mRNA results in the production of an aberrant Type VI alpha 1 chain protein, leading to the development of neuromuscular disorders. Detection of this mutation can be used to diagnose individuals at risk for developing collagen VI-related disorders. Normal splicing of pre-mRNA containing the mutation can be achieved through the use of exon-skipping technology.

Thus, this disclosure provides antisense oligomers targeted to a sequence in intron 11 of an COL6A1 pre-mRNA molecule, wherein hybridization of the antisense oligomer to the target sequence in mutated COL6A1 pre-mRNA results in production of normal (wt) alpha 1(VI) chain protein. In one aspect, hybridization of the antisense oligomer to the target sequence results in normal splicing from exon 11 to exon 12. In one aspect, production of a normal alpha 1(VI) chain protein is due to the alteration or modulation of splicing resulting from hybridization of the antisense oligomer to the target sequence in the pre-mRNA. In one aspect, hybridization of the antisense oligomer to the target sequence results in production of a mature COL6A1 mRNA lacking a pseudo-exon (SEQ ID NO:4). In one aspect, hybridization of the antisense oligomer to the target sequence results in production of a mature alpha 1(VI) chain protein lacking SEQ ID NO:5. In one aspect, hybridization of the antisense oligomer to the target sequence results in production of a mature COL6A1 mRNA encoding a normal alpha 1(VI) chain protein. In one aspect, hybridization of the antisense oligomer to the target sequence results in production of a mature COL6A1 mRNA comprising SEQ ID NO:61. In one aspect, hybridization of the antisense oligomer to the target sequence results in production of a mature COL6A1 mRNA encoding a protein comprising SEQ ID NO:62.

Antisense oligomers of this disclosure may specifically hybridize with polynucleotide sequences in intron 11 of COL6A1 pre-mRNA. In one aspect, the antisense oligomer does not hybridize with sequences in exon 11 or exon 12. In one aspect, the target sequence is at least 90% identical to a polynucleotide sequence in intron 11 of COL6A1 pre-mRNA. In one aspect, the target sequence is at least 90% identical to a polynucleotide sequence in SEQ ID NO:3. In one aspect, the antisense oligomer is targeted to a polynucleotide sequence in SEQ ID NO:3 or SEQ ID NO:4.

The length of antisense oligomers of the invention can be optimized for specific hybridization to a target sequence. In one aspect, the antisense oligomer is 10 to 50 nucleotides in length. In one aspect, the antisense oligomer is 10 to 30 nucleotides in length. In one aspect, the antisense oligomer is 15 to 25 nucleotides in length. In one aspect, the antisense oligomer comprises, or consists of, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases.

Preferred antisense oligomers are those having a high degree of complementarity with the target sequence. In one aspect, the antisense oligomer is sufficiently complementary to the target sequence such that the antisense oligomer specifically hybridizes to a COL6A1 pre-mRNA comprising the target sequence. In one aspect, the antisense oligomer comprises a nucleic acid sequence comprising at least six contiguous nucleobases fully complementary to at least six contiguous nucleobases in the target sequence. In one aspect, the target sequence comprises a sequence at least 90% identical to a SEQ ID NO:23, SEQ ID NO:24, SEQ ID NO:25, NO:26, SEQ ID NO:27, SEQ ID NO:28, SEQ ID NO:29, SEQ ID NO:30, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, or SEQ ID NO:58. In one aspect, the target sequence comprises SEQ ID NO:23, SEQ ID NO:24, SEQ ID NO:25, NO:26, SEQ ID NO:27, SEQ ID NO:28, SEQ ID NO:29, SEQ ID NO:30, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, or SEQ ID NO:58.

In one aspect, the antisense oligomer comprises a sequence at least 85%, at least 90%, at least 95%, at least 97% or at least 99% identical to SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, or SEQ ID NO:44. In one aspect, the antisense oligomer comprises SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, or SEQ ID NO:44.

Antisense oligomers can be made from RNA, DNA, combinations thereof, and/or modified forms thereof. In one aspect, the antisense oligomer is an antisense RNA molecule. In one aspect, the antisense oligomer is an RNA molecule that comprises a modification selected from the group consisting of a nucleoside modification, an internucleoside modification, a sugar modification, a sugar-internucleoside linkage modification, a peptide addition, and combinations thereof. In one aspect, the antisense oligomer is modified to reduce degradation by a ribonuclease. The antisense oligomer may be a morpholino oligomer.

Antisense oligomers of this disclosure may be produced using expression vectors. One aspect of the invention is an expression vector encoding an antisense oligomer of the invention. In one aspect, the expression vector is an isolated nucleic acid molecule. In one aspect, the expression vector is viral expression vector (e.g., AAV vector).

Antisense oligomers of the invention can be used to modulate splicing of COL6A1 pre-mRNA. One aspect of the invention is a method of modulating splicing of a COL6A1 pre-mRNA molecule comprising a non-native splice donor or splice acceptor site in intron 11, comprising contacting a cell expressing COL6A1 pre-mRNA molecule comprising a non-native splice donor or splice acceptor site with an antisense oligomer of the invention or an expression vector expressing an oligomer of the invention.

One aspect of the invention is a method of treating a collagen VI-related disorder (COL6-RD), comprising administering to an individual in need of such treatment an antisense oligomer of this disclosure. In one aspect, the COL6-RD is a COL6A1-RD. In one aspect, the individual comprises a COL6A1 gene comprising a mutation in intron 11 that introduces a new splice donor site. In one aspect, the individual comprises a COL6A1 gene comprising a NH_001848 c.930+189 C>T mutation. In one aspect, the individual is treated by administering to the individual an expression vector expressing an antisense oligomer of this disclosure. In one aspect, the individual is treated by administering to the individual an antisense oligomer targeted to a sequence comprising SEQ ID NO:3 or SEQ ID NO:4. In one aspect, the individual is treated by administering to the individual an antisense oligomer targeted to a sequence comprising a sequence at least 90% identical to SEQ ID NO:23, SEQ ID NO:24, SEQ ID NO:25, NO:26, SEQ ID NO:27, SEQ ID NO:28, SEQ ID NO:29, SEQ ID NO:30, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, or SEQ ID NO:58. In one aspect, the individual is treated by administering to the individual an antisense oligomer targeted to a sequence comprising SEQ ID NO:23, SEQ ID NO:24, SEQ ID NO:25, NO:26, SEQ ID NO:27, SEQ ID NO:28, SEQ ID NO:29, SEQ ID NO:30, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, or SEQ ID NO:58.

In one aspect, the individual is treated by administering to the individual an antisense oligomer comprising a sequence at least 85%, at least 90%, at least 95%, at least 97%, or at least 99% identical to SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, or SEQ ID NO:44. In one aspect, the individual is treated by administering to the individual an antisense oligomer comprising SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, or SEQ ID NO:44.

One aspect of the invention is a method of diagnosing the likelihood of an individual to develop a Collagen VI related disorder (COL6-RD) comprising obtaining a biological sample from the individual, and analyzing the sample to determine if the C or T allele is present at a locus in chromosome 21 represented by SEQ ID NO:3 or SEQ ID NO:6, wherein the presence of the T allele indicates the individual will develop a COL6-RD.

One aspect of the invention is a method of diagnosing the likelihood of an individual to develop a neuromuscular disorder, comprising obtaining a biological sample from the individual, and, analyzing the sample to determine if the C or T allele is present at a locus in chromosome 21 represented by SEQ ID NO:3 or SEQ ID NO:6, wherein the presence of the T allele indicates the individual will develop a neuromuscular disorder.

One aspect of the invention is a method of diagnosing the likelihood of an individual to develop Ullrich muscular dystrophy, comprising obtaining a biological sample from the individual, and, analyzing the sample to determine if the C or T allele is present at a locus in chromosome 21 represented by SEQ ID NO:3 or SEQ ID NO:6, wherein the presence of the T allele indicates the individual will develop Ullrich muscular dystrophy.

One aspect of the invention is a method of diagnosing a COL6-RD in an individual comprising:
 a. obtaining a plasma sample from an individual,
 b. separating the sample into a cellular and non-cellular fraction,
 c. detecting the presence of the T allele in the cellular fraction, and
 d. providing a diagnosis of a COL6-RD based on the presence of the T allele in the cellular fraction of the sample.

In these methods, the biological sample may comprise a blood sample, a tissue sample (esp. a muscle biopsy), and a buccal swab. The presence or absence of the C or T allele may be detected by analyzing genomic DNA, RNA transcripts, and/or the alpha1(VI) protein.

Another aspect of this disclosure is a method of detecting a SNP in intron 11 of the COL6A1 gene, comprising obtaining a nucleic acid sample from an individual that includes a locus in chromosome 21 represented by SEQ ID NO:3, and detecting the presence of the T allele at position 21 of SEQ ID NO:6.

Another aspect of this disclosure is a method of detecting a SNP in intron 11 of the COL6A1 gene, comprising obtaining a nucleic acid sample from an individual that includes a locus in chromosome 21 represented by SEQ ID NO:3, and detecting the presence of the T allele at position 21 of SEQ ID NO:6.

Another aspect of this disclosure is a method of detecting a SNP in intron 11 of the COL6A1 gene, comprising obtaining a plasma sample from a human patient, and detecting whether the T allele or the C allele is present at position 21 of the genomic DNA sequence of SEQ ID NO:6.

Another aspect of this disclosure is a method of detecting Ullrich muscular dystrophy in a patient comprising obtaining a plasma sample from a human patient, and detecting whether the T allele or the C allele is present at position 21 of the genomic DNA sequence of SEQ ID NO:6.

Another aspect of this disclosure is a method of confirming a diagnosis of Ullrich muscular dystrophy in a patient comprising obtaining a plasma sample from a human patient, and detecting whether the T allele or the C allele is present at position 21 of the genomic DNA sequence of SEQ ID NO:6, wherein the presence of the T allele is confirmatory of a diagnosis of Ullrich muscular dystrophy.

This disclosure also provides recombinant nucleic acid molecules comprising an insert comprising at least a portion of intron 11 comprising SEQ ID NO:6, wherein the portion of intron 11 is flanked by at least a 5' splice donor site and at least a 3' splice acceptor site, the insert being operationally linked to a promoter sequence.

Another aspect of this disclosure is a method of identifying compounds capable of modulating splicing of COL6A1 pre-mRNA, comprising: introducing a test compound into a cell comprising a recombinant expression vector comprising an insert comprising at least a portion of intron 11 comprising SEQ ID NO:6, wherein the portion of intron 11 is flanked by at least a 5' splice donor site and at least a 3' splice acceptor site, the insert being operationally linked to a promoter sequence; performing a first polymerase chain reaction (PCR) assay on nucleic acid molecules obtained from the cell, using a set of primers that bind sequences flanking the 3' splice acceptor-intron 11 portion-5' splice donor insert; and, comparing the size of the PCR product with a PCR product produced from a second PCR assay performed on a second cell comprising the recombinant expression vector but lacking the test antisense oligomer, and using the same pair of primers; wherein if the PCR product produced from the first PCT assay is smaller than the PCR product produced in the second PCR assay, identifying the test compound as capable of modulating splicing of COL6A1 pre-mRNA.

This disclosure also provides kits for practicing methods of the invention. These kits may be used to predict the risk of an individual to develop a COL6-RD, and may comprise an antisense oligomer of the invention; and instructions for using antisense oligomer. In one aspect, the kit is useful for modulating splicing of COL6A1 pre-mRNA, and comprises an antisense oligomer of the invention and instructions for using the antisense oligomer.

BRIEF DESCRIPTION OF THE DRAWINGS

FIG. 7A illustrates the design and positioning strategy of the tested AONs. FIG. 7B shows representative gel images of HEK293T cells transfected with the minigene construct (+Ex-11-13), and treated with the 2'OMe antisense oligonucleotides, performed in duplicate and amplified by reverse-transcriptase PCR. FIG. 7C shows the percentage of expression determined using the gel density to measure the ratio of mutant to normal expression of the experiments illustrated in FIG. 7B.

FIG. 8A shows the strategy used to design phosphorothioate morpholino antisense oligonucleotides (PMO) to promote skipping of the pseudo-exon. The PMO were positioned either at the splice acceptor site (PMO-1, PMO-1b, PMO-1c), at the splice donor site (PMO-3, PMO-3b, PMO-3c), or within the pseudo-exon at a predicted splicing enhancer site (PMO-2, PMO-2b, PMO-2c, PMO-2d, PMO-2e, PMO-2f, PMO-4, PMO-5). FIG. 8B shows representative gel images of HEK cells transfected with the minigene construct (+Ex-11-13), and treated with the PMO antisense oligonucleotides, performed in duplicate and amplified by reverse-transcriptase PCR. FIG. 8C shows the percentage of expression determined using the gel density to measure the ratio of mutant to normal expression of the experiments illustrated in FIG. 8B.

FIG. 9A shows the relative pseudoexon expression levels in patient-derived cultured fibroblasts treated with the indicated oligomer. A reverse-transcriptase PCR assay designed to specifically detect the pseudoexon was used to measure its expression. Bars represent the average of three biological replicates±standard error of the mean. Each biological replicate is the average of 2 to 3 transfections. Statistical analyzes were performed using multiple comparisons ANOVA followed by Dunnet correction, for each treatment compared to PMO-Negative treatment. *p<0.01, **p<0.001. FIG. 9B shows the relative pseudoexon expression levels (calculated as in FIG. 9A) in fibroblasts treated with the indicated combination of oligomers. FIG. 9C shows representative images of patient-derived fibroblasts treated with either a non-targeting PMO (PMO-Neg), or with a combination of PMO-2b and PMO-3 for 5 days, and with sodium ascorbate for 3 days, before staining for matrix-deposited collagen VI. FIG. 9D shows the number of tetramers per microfibril following treatment with PMO-2b and PMO-3, calculated using rotary shadowing electron microscopy images.

FIG. 10A is a schematic a chimeric splicing reporter that was prepared by cloning the mouse genomic sequence encompassing exon 11 to exon 13, and by replacing the intron 11 sequence with human intron 11, in presence of the wildtype (+189C) or the mutant (+189T) genotype.

DETAILED DESCRIPTION

Figure 1:
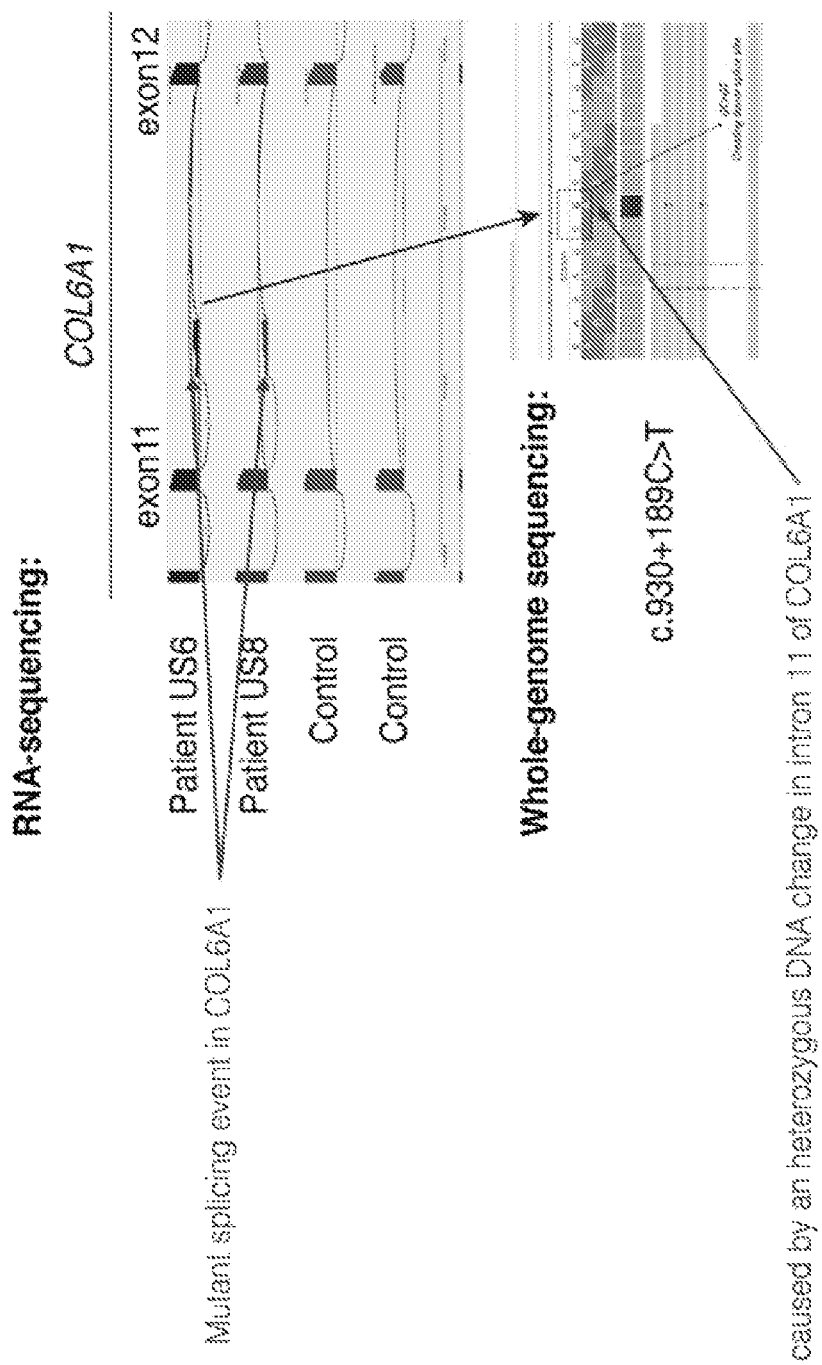
FIG. 1 shows RNA-sequencing analysis (top) of two collagen VI patients revealed the retention of intronic sequence (72 bp) in mature transcripts between exon 11 and exon 12 of COL6A1. This splicing event was not identified in 195 additional patient and control samples. Whole-genome sequencing of patient 1 (bottom) showed the presence of a de novo heterozygous mutation in intron 11, adjacent to the new splicing event.

This disclosure provides methods of identifying individuals at risk for developing Collagen VI-related disorders (COL6-RD), as well as methods for treating such individuals. The invention is based on the inventors' discovery of a mutation in the COL6A1 gene (NCBI Gene ID: 1291) that results in production of a mutant form of the Type VI collagen alpha 1 chain protein ("alpha 1(VI) chain"), leading to neuromuscular disorders. The newly discovered substitution mutation (C>T) at a specific location in the region between exon 11 and exon 12 of the alpha 1(VI) chain gene (COL6A1) introduces a new, functional 5'-splice donor site in the pre-mRNA molecule transcribed from the mutated gene. Utilization of the splice donor site resulting from this mutation alters splicing of COL6A1 pre-mRNA, such that the mature mRNA contains 72 additional nucleotides (a pseudo-exon; SEQ ID NO:4) between exon 11 and exon 12. Individuals possessing the T allele of this C>T mutation that results in the inclusion of the pseudo-exon in the COL6A1 gene transcripts develop COL6-RD, particularly neuromuscular disorders such as Ullrich muscular dystrophy.

The inventors tested the frequency of known mutations in COL6 genes in a cohort of NIH patients and found that this COL6A1 intronic mutation was the most common individual mutation. Thus, this mutation is a newly-discovered single nucleotide polymorphism (SNP), which results in a mutant form of the alpha 1(VI) chain, and the presence of this SNP is predictive of an individual developing a COL6-RD.

A diagnostic method of this disclosure may generally be accomplished by obtaining a biological sample from an individual and analyzing the sample to identify the allele(s) of this polymorphism carried by the individual. Nucleic acid molecules in the sample are analyzed to determine the nucleotide present at the position corresponding to position 189 of intron 11 (SEQ ID NO:3) [NM_001848 c.930+189) of the gene encoding the alpha 1 chain of Type VI collagen. The presence of cytosine (C) at the position corresponding to position 189 of intron 11 indicates the individual produces normally spliced COL6A1 mRNA. In contrast, the presence of a thymidine (T) at the position corresponding to position 189 of intron 11 indicates aberrant splicing COL6A1 pre-mRNA.

It should be understood that the invention is not limited to the specific embodiments described herein, as such may vary. Additionally, the terminology used herein is for the purpose of describing particular embodiments only, and is not intended to be limiting on the finally claimed invention, since the scope of the invention will be limited only by the claims.

As used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly, the terms "comprising", "including" and "having" can be used interchangeably. It is further noted that the claims may be drafted to exclude any optional element. As such, this statement is intended to serve as antecedent basis for use of such exclusive terminology as "solely," "only" and the like, in connection with the recitation of claim elements, or use of a "negative" limitation.

As used herein, a biological sample refers to any fluid or tissue from an individual that can be analyzed for the presence of a polymorphism. Preferably, such samples comprise nucleic acid molecules, such as DNA, cDNA, and/or RNA, including mRNA and miRNA. Examples of the type of sample that can be used to practice the methods of this disclosure include, but are not limited to, a blood sample, a tissue sample (esp. a muscle biopsy), and a buccal swab. Methods of obtaining such samples are known to those skilled in the art.

Once a sample has been obtained, it is analyzed for the presence or absence of specific alleles (i.e., C or T) of intron 11 from the COL6A1 gene. This may include one or more of detecting the point mutation in genomic DNA, detecting the presence of the pseudo exon in RNA transcripts, and/or detecting the 9-amino acid sequence in the COL6A1 protein produced as a result of the insertion of the pseudo exon. The presence of the 'T' allele (as evidenced by any one or more of these biomarkers of this SNP) indicates the individual is at greatly increased risk of developing a neuromuscular dystrophy, especially Ullrich muscular dystrophy.

As used herein, the COL6A1 gene, refers to a nucleic acid sequence encoding an alpha (a) chain of Type VI collagen from a mammal. One example of a COL6A1 coding sequence is the gene at position number hg38 chr21:45,981,737-46,005,050 of the human genome assembly found at genome.ucsc.edu. Another example is the nucleic acid sequence represented as GenBank Accession No. BC052575.1. Further, a COL6A1 coding sequence can refer to a nucleic acid sequence encoding at least a portion of an alpha 1 chain from Type VI collagen. Such a portion can encode a fragment of the protein (e.g., a 10, 20, 30, 40, 50, 60, 70, 80, 90 or 100 contiguous amino acid segments from any part of the whole protein), may encode a domain (e.g., a transmembrane domain), may be an exon, or may refer to the entire protein, including any splicing variants. COL6A1 genes or coding sequences of this disclosure can be from any mammal having such a gene or coding sequence. Such mammals include, but are not limited to, humans, mice, canines, felines, and equines.

As used herein, an allele refers to one specific form of a polymorphism. If a specific sequence contains a polymorphism having several sequence variations, each unique variation is referred to as an allele. For example, if a particular position in a nucleotide sequence in a chromosome contains a cytosine, and the corresponding position in the homologous chromosome contains a thymidine, such polymorphism is said to have two alleles. If a third form of the chromosome exists in which the corresponding position is a guanine, the polymorphism would be said to have three alleles. Moreover, as an example of how such alleles can be identified, or differentiated from one another, the exemplified alleles can be referred to as "a C allele, a T allele and G allele," respectively. The specific nucleotide changes at these variant sites that differ between different alleles are termed variants, mutations, or polymorphisms.

One allelic form of a polymorphism may be arbitrarily designated as the reference form and other allelic forms are designated as alternative or variant alleles. For example, if a particular allele is associated with a particular phenotypic characteristic (e.g., the presence of a disease, the ability to respond to a disease, the ability to respond to treatment for a disease, etc.), the beneficial allelic form may be referred to as a "wild-type form" or beneficial form, while the unfavorable, disease-associated allelic form can be referred to as the disadvantageous form, the unfavorable form, the mutant form, the alternative form, the genetic risk variant, and the like. With regard to this disclosure, the wild-type (wt) or reference form is the C allele, and the mutant or genetic risk variant is the T allele.

Sequences referred to throughout this application are shown Table 1 below.

TABLE 1

| SEQ ID NO | Sequence | Comments |
|---|---|---|
| 1 | GGAGAAAAAGGGAGCCGTGGGGAGAAG | Exon 11 |
| 2 | GEKGSRGEK (GlyGluLysGlySerArgGlyGluLys) | Amino acid sequence of Exon 11 (9 amino acids) |

TABLE 1-continued

| SEQ ID NO | Sequence | Comments |
|---|---|---|
| 3 | gtgagtgaggctcgacctcggagctggtctctccagg cgcagatgtgccatcctggacgagggtgtccccgggg atgaggacagtgtccctgacaggagaccacgtgtcct gcagacccgctccaccgcccctcgccgtcccctccat ctggaaggacaaggacagccacccaggcacccagcaa aggcgcctgtgtcactttcaccccaccccagagcagg ggtccccgggcggttaccctctgcggagccgggggt ccccgggcggttaccctctgcggagccgggggtccc ccgggcggttaccctctgcagagcggcccctcccat cactgtcagtcccatgattctcagcagtgatgttgt ccctcgggttgggggcacccaagcccctgcctcgcg tgggcctaagccaggcttgccctgccctccccacccc aaataccccctcacacccgcttcctgtctccgcag | Intron 11 |
| 4 | acccgctccaccgcccctcgccgtcccctccatctgg aaggacaaggacagccacccaggcacccagcaaag | Sequence of insertion = pseudo exon (72 base pairs) |
| 5 | TRSTAPRRPLHLEGQGQPPRHPAK | Amino acid sequence of pseudo exon (24 aa's) |
| 6 | acccaggcacccagcaaagg(c/t)gcctgtgtcact ttcaccccc | Mutation site +/-20 bases (C is wildtype; T is mutation) mutation is at position 21 of SEQ ID NO: 6 |
| 7 | GGCTCCAGGGGACCCAAGGGCTACAAG | Exon 12 |
| 8 | GSRGPKGYK (GlySerArgGlyProLysGlyTyrLys) | Amino acid sequence of Exon 12 (9 amino acids) |
| 9 | CGTGGGGAGAAGacccgctccacc | Exon 11/pseudo-exon junction |
| 10 | RGEKTRST | Translation of SEQ ID NO: 9 |
| 11 | cacccagcaaagGGCTCCAGGGGA | Pseudo-exon/exon 12 junction |
| 12 | HPAKGSRG | Translation of SEQ ID NO: 11 |
| 13 | CGTGGGGAGAAGGGCTCCAGGGGA | Exon 11/exon 12 junction |
| 14 | RGEKGSRG | Translation of SEQ ID NO: 13 |
| | 2'O-Methyl Phosphorothioate oligonucleotide (2'O-Me) sequences | |
| 15 | GUGGAGCGGGUCUGCAGGACACGUG | COL6Aps11_A(-14 +11)(ID: 23) |
| 16 | GGCUGUCCUUGUCCUCCCAGAUGGA | COL6Aps11_A(+29 +53)(ID: 24) |
| 17 | AGGCACCUUUGCUGGGUGCCUGGGU | COL6Aps11_D(+19 -6)(ID: 25) |
| 18 | UGAAAGUGACACAGGCACCUUUGCU | COL6Aps11_D(+7 -18)(ID: 26) |
| 19 | GGUGAAAGUGACACAGGCAACCU | COL6Aps11_D(+2 -20)(ID: 27) |
| 20 | AGAUGGAGGGGACGGCGAGG | COL6Aps11_A(+16 +35)(ID: 17) |

TABLE 1-continued

| SEQ ID NO | Sequence | Comments |
|---|---|---|
| 21 | GGCUGUCCUUGUCCUUCCAG | COL6Aps11_A(+33 +52)(ID: 18) |
| 22 | GUGCCUGGGUGGCUGUCCUU | COL6Aps11_A(+37 +56)(ID: 19) |
| | Target Sequences on (alpha 1(Vi) chain) pre-mRNA for SEQ ID Nos 15-22 | |
| 23 | CACGUGUCCUGCAGACCCGCUCCAC | Target sequence for COL6Aps11_A(-14 +11) |
| 24 | UCCAUCUGGAAGGACAAGGACAGCC | Target sequence for COL6Aps11_A(+29 +53) |
| 25 | ACCCAGGCACCCAGCAAAGGUGCCU | Target sequence for COL6Aps11_D(+19 -6) |
| 26 | AGCAAAGGUGCCUGUGUCACUUUCA | Target sequence for COL6Aps11_D(+7 -18) |
| 27 | AGGUGCCUGUGUCACUUUCACC | Target sequence for COL6Aps11_D(+2 -20) |
| 28 | CCUCGCCGUCCCCUCCAUCU | Target sequence for COL6Aps11_A(+16 +35) |
| 29 | CUGGAAGGACAAGGACAGCC | Target sequence for COL6Aps11_A(+33 +52) |
| 30 | AAGGACAGCCACCCAGGCAC | Target sequence for COL6Aps11_A(+37 +56) |
| | Phosphorothiamidate morpholino oligonucleotide (PMO) sequences | |
| 31 | AGGACACCTGGTCTCCTGTCAGGGA | COL6A1-ex11b-1 (ID:1) |
| 32 | GCTGTCCTTGTCCTTCCAGATGGAG | COL6A1-ex11b-2 (ID:2) |
| 33 | TGAAAGTGACACAGGCACCTTTGCT | COL6A1-ex11b-3 (ID:3) |
| 34 | GTGGCTGTCCTTGTCCTTCCAGATG | COL6A1-ex11b-2b (ID:2b) |
| 35 | TTGTCCTTCCAGATGGAcGGGAC | COL6A1-ex11b-4 (ID:4) |
| 36 | GTGCCTGGGTcGCTGTCCTTGTCCT | COL6A1-ex11b-5 (ID:5) |
| | New oligo sequences added to PCT | |
| 37 | TCTGCAGGACACGTGGTCTCCTGTC | COL6A1-intron11-1b |
| 38 | GGTCTGCAGGACACGTGGTCTCCTG | COL6A1-intron11-1c |
| 39 | CTGTCCTTGTCCTTCCAGATGGAGG | COL6A1-intron11-2c |
| 40 | GGCTGTCCTTGTCCTTCCAGATGGA | COL6A1-intron11-2d |

TABLE 1-continued

| SEQ ID NO | Sequence | Comments |
|---|---|---|
| 41 | TGGCTGTCCTTGTCCTTCCAGATGG | COL6A1-intron11-2e |
| 42 | GGTGGCTGTCCTTGTCCTTCCAGAT | COL6A1-intron11-2f |
| 43 | TGGGGTGAAAGTGACACAGGCACCT | COL6A1-intron11-3b |
| 44 | GGTGAAAGTGACACAGGCACCTTTG | COL6A1-intron11-3c |
| | Target Sequences on (alpha 1(Vi) chain) pre-mRNA for SEQ ID Nos 15-22 | |
| 45 | UCCCUGACAGGAGACCACGUGUCCU | Target sequence for COL6A1-ex11b-1 |
| 46 | CUCCAUCUGGAAGGACAAGGACAGC | Target sequence for COL6A1-ex11b-2 |
| 47 | AGCAAAGGUGCCUGUGUCACUUUCA | Target sequence for COL6A1-ex11b-3 |
| 48 | CAUCUGGAAGGACAAGGACAGCCAC | Target sequence for COL6A1-ex11b-2b |
| 49 | GUCCCCUCCAUCUGGAAGGACAA | Target sequence for COL6A1-ex11b-4 |
| 50 | AGGACAAGGACAGCCACCCAGGCAC | Target sequence for COL6A1-ex11b-5 |
| | New target sequences in PCT | |
| 51 | gacaggagaccacguguccugcagA | Target sequence for COL6A1-intron11-1b |
| 52 | caggagaccacguguccugcagACC | Target sequence for COL6A1-intron11-1c |
| 53 | CCUCCAUCUGGAAGGACAAGGACAG | Target sequence for COL6A1-intron11-2c |
| 54 | UCCAUCUGGAAGGACAAGGACAGCC | Target sequence for COL6A1-intron11-2d |
| 55 | CCAUCUGGAAGGACAAGGACAGCCA | Target sequence for COL6A1-intron11-2e |
| 56 | AUCUGGAAGGACAAGGACAGCCACC | Target sequence for COL6A1-intron11-2f |
| 57 | AGgugccugugucacuuucacccca | Target sequence for COL6A1-intron11-3b |
| 58 | CAAAGgugccugugucacuuucacc | Target sequence for COL6A1-intron11-3c |
| | Sequences for alpha 1 (VI) ORF and protein | |
| 59 | AGCCGTGGGGAGAAGgtgagtgaggctcga | Exon 11/intron 11 junction |
| 60 | ttcctgtctccgcagGGCTCCAGGGGACCC | Intron 11/exon 12 junction |
| 61 | Nucleic acid sequence encoding wt alpha 1 (VI) chain protein | NM_001848 |

TABLE 1-continued

| SEQ ID NO | Sequence | Comments |
|---|---|---|
| 62 | MRAARALLPLLLQACWTAAQDEPETPRAVAFQDCPVD LFFVLDTSESVALRLKPYGALVDKVKSFTKRFIDNLR DRYYRCDRNLVWNAGALHYSDEVEIIQGLTRMPGGRD ALKSSVDAVKYFGKGTYTDCAIKKGLEQLLVGGSHLK ENKYLIVVTDGHPLEGYKEPCGGLEDAVNEAKHLGVK VFSVAITPDHLEPRLSIIATDHTYRRNFTAADWGQSR DAEEAISQTIDTIVDMIKNNVEQVCCSFECQPARGPP GLRGDPGFEGERGKPGLPGEKGEAGDPGRPGDLGPVG YQGMKGEKGSRGEKGSRGPKGYKGEKGKRGIDGCDGV KGEMGYPGLPGCKGSPGFDGIQGPPGPKGDPGAFGLK GEKGEPGADGEAGRPGSSGPSGDEGQPGEPGPPGEKG EAGDEGNPGPDGAPGERGGPGERGPRGTPGTRGPRGD PGEAGPQGDQGREGPVGVPGDPGEAGPIGPKGYRGDE GPPGSEGARGAPGPAGPPGDPGLMGERGEDGPAGNGT EGFPGFPGYPGNRGAPGINGTKGYPGLKGDEGEAGDP GDDNNDIAPRGVKGAKGYRGPEGPQGPPGHQGPPGPD ECEILDIIMKMCSCCECKCGPIDLLFVLDSSESIGLQ NFEIAKDFVVKVIDRLSRDELVKFEPGQSYAGVVQYS HSQMQEHVSLRSPSIRNVQELKEAIKSLQWMAGGTFT GEALQYTRDQLLPPSPNNRIALVITDGRSDTQRDTTP LNVLCSPGIQVVSVGIKDVFDFIPGSDQLNVISCQGL APSQGRPGLSLVKENYAELLEDAFLKNVTAQICIDKK CPDYTCPITFSSPADITILLDGSASVGSHNFDTTKRF AKRLAERFLTAGRTDPAHDVRVAVVQYSGTGQQRPER ASLQFLQNYTALASAVLAMDFINDATDVNDALGYVTR FYREASSGAAKKRLLLFSDGNSQGATPAAIEKAVQEA QRAGIEIFVVVVGRQVNEPHIRVLVTGKTAEYDVAYG ESHLFRVPSYQALLRGVFHQTVSRKVALG | Sequence of wt alpha 1(VI) chain protein. Translation of exon 11/12 sequences is underlined |
| 63 | MRAARALLPLLLQACWTAAQDEPETPRAVAFQDCPVD LFFVLDTSESVALRLKPYGALVDKVKSFTKRFIDNLR DRYYRCDRNLVWNAGALHYSDEVEIIQGLTRMPGGRD ALKSSVDAVKYFGKGTYTDCAIKKGLEQLLVGGSHLK ENKYLIVVTDGHPLEGYKEPCGGLEDAVNEAKHLGVK VFSVAITPDHLEPRLSIIATDHTYRRNFTAADWGQSR DAEEAISQTIDTIVDMIKNNVEQVCCSFECQPARGPP GLRGDPGFEGERGKPGLPGEKGEAGDPGRPGDLGPVG YQGMKGEKGSRGEKTRSTAPRRPLHLEGQGQPPRHPA KGSRGPKGYKGEKGKRGIDGVDGVKGEMGYPGLPGCK GSPGFDGIQGPPGPKGDPGAFGLKGEKGEPGADGEAG RPGSSGPSGDEGQPGEPGPPGEKGEAGDEGNPGPDGA PGERGGPGERGPRGTPGTRGPRGDPGEAGPQGDQGRE GPVGVPGDPGEAGPIGPKGYRGDEGPPGSEGARGAPG PAGPPGDPGLMGERGEDGPAGNGTEGFPGFPGYPGNR GAPGINGTKGYPGLKGDEGEAGDPGDDNNDIAPRGVK GAKGYRGPEGPQGPPGHQGPPGPDECEILDIIMKMCS CCECKCGPIDLLFVLDSSESIGLQNFEIAKDFVVKVI DRLSRDELVKFEPGQSYAGVVQYSHSQMQEHVSLRSP SIRNVQELKEAIKSLQWMAGGTFTGEALQYTRDQLLP PSPNNRIALVITDGRSDTQRDTTPLNVLCSPGIQVVS VGIKDVFDFIPGSDQLNVISCQGLAPSQGRPGLSLVK ENYAELLEDAFLKNVTAQICIDKKCPDYTCPITFSSP ADITILLGDSASVGSHNFDTTKRFAKRLAERFLTAGR TDPAHDVRVAVVQYSGTGQQRPERASLQFLQNYTALA SAVDAMDFINDATDVNDALGYVTRFYREASSGAAKKR LLLFSDGNSQGATPAAIEKAVQEAQRAGIEIFVVVVG RQVNEPHIRVLVTGKTAEYDVAYGESHLFRVPSYQAL LRGVFHQTVSRKVALG | Sequence of alpha 1(VI) chain protein containing pseudo-exon; (TRSTAPRRPLHL EGQGQPPRHPAK) Translations of exon 11 and exon 12 sequences are underlined. Translation of pseudoexon sequence is bolded |

It is well known that chromosomes are composed of double-stranded DNA molecules. Thus, while this disclosure refers to detecting the presence of particular nucleotides in a particular nucleic acid strand or sequence (e.g., SEQ ID NO:3, SEQ ID NO:4, SEQ ID NO:6, etc.), this disclosure may also be practiced by detecting the corresponding nucleotide in a complementary strand. The newly discovered polymorphism of this disclosure is located in an intronic segment of the genome (intron 11 of the COL6A1 gene) which is represented by SEQ ID NO:3.

Thus, this disclosure provides methods of diagnosing the likelihood of an individual to develop a Collagen VI related disorder (COL6-RD). These methods include obtaining a biological sample from the individual, and analyzing the sample to determine if the C or T allele is present at a locus in chromosome 21 represented by SEQ ID NO:3. The presence of the T allele indicates the individual will develop a COL6-RD.

Another method of this disclosure is a method of diagnosing the likelihood of an individual to develop a neuromuscular disorder. This method includes obtaining a biological sample from the individual, and analyzing the sample to determine if the C or T allele is present at a locus in chromosome 21 represented by SEQ ID NO:3. The presence of the T allele indicates the individual will develop a neuromuscular disorder.

A related method of this disclosure is a method of diagnosing the likelihood of an individual to develop Ullrich muscular dystrophy. This method includes obtaining a biological sample from the individual, and analyzing the sample to determine if the C or T allele is present at a locus in chromosome 21 represented by SEQ ID NO:3. The presence of the T allele indicates the individual will develop Ullrich muscular dystrophy.

A related method is a method of diagnosing a COL6-RD in an individual including obtaining a plasma sample from an individual, separating the sample into a cellular and non-cellular fraction, detecting the presence of the T allele in the cellular fraction, and providing a diagnosis of a COL6-RD based on the presence of the T allele in the cellular fraction of the sample.

In these methods, as noted above, the biological sample may include, for example, a blood sample, a tissue sample (esp. a muscle biopsy), and a buccal swab, and the presence or absence of the C or T allele may be detected by analyzing genomic DNA, RNA transcripts, and/or the COL6A1 protein.

Similarly, this disclosure provides methods of detecting a SNP in intron 11 of the COL6A1 gene, including obtaining a nucleic acid sample from an individual that includes a locus in chromosome 21 represented by SEQ ID NO:3, and detecting the presence of the T allele at a position corresponding to position 21 of SEQ ID NO:6.

A related method of detecting a SNP in intron 11 of the COL6A1 gene, provided by this disclosure, includes obtaining a plasma sample from a human patient, and detecting whether the T allele or the C allele is present at a position corresponding to position 21 of the genomic DNA sequence of SEQ ID NO:6.

Thus, a related method provided by this disclosure is a method of detecting Ullrich muscular dystrophy in a patient by obtaining a plasma sample from a human patient, and detecting whether the T allele or the C allele is present at a position corresponding to position 21 of the genomic DNA sequence of SEQ ID NO:6.

A number of methods are available for analyzing the presence or absence of the SNP described in this disclosure, which can be applied to the COL6A1 region of the genome in a nucleic acid sample isolated from a biological sample obtained from a subject. Assays for detection of polymorphisms or mutations fall into several categories, including but not limited to, direct sequencing assays, fragment polymorphism assays, hybridization assays, and computer based data analysis. Protocols and commercially available kits or services for performing these general methods are available. These assays may be performed in combination or in hybrid (i.e., different reagents or technologies from several assays are combined to yield one assay). The following assays are useful, and are described in relationship to detection of the SNP found in the COL6A1 region of the genome.

The presence or absence of alleles may be determined using a direct sequencing technique. In these assays, DNA samples are first isolated from a subject using any suitable method. DNA in the region of interest may be amplified using the Polymerase Chain Reaction (PCR). Alternatively, or additionally, RNA may be used to generate cDNA and then perform detection analysis of the polymorphism. Following amplification, DNA or cDNA in the region of interest (i.e., the region containing the polymorphism) is sequenced using any suitable method, including but not limited to, manual sequencing (e.g., using labeled marker nucleotides), or automated sequencing. The results of the sequencing are displayed using any suitable method. The sequence is examined and the presence or absence of a given allele is determined.

Alleles may also be determined using a PCR-based assay. The PCR assay comprises the use of oligonucleotide primers to amplify a fragment containing the polymorphism of interest. Amplification of a target polynucleotide sequence may be carried out by any method known to the skilled artisan. Amplification methods include, but are not limited to, PCR, including real time PCR (RT-PCR), strand displacement amplification, pyrosequencing, strand displacement amplification using Phi29 DNA polymerase (U.S. Pat. No. 5,001,050), transcription-based amplification, self-sustained sequence replication ("3SR"), the Qbeta replicase system, nucleic acid sequence-based amplification ("NASBA"), the repair chain reaction ("RCR"), boomerang DNA amplification (or "BDA"), and mismatch PCR. PCR is the preferred method of amplifying the target polynucleotide sequence.

PCR may be carried out in accordance with techniques known by the skilled artisan. In general, PCR includes first treating a nucleic acid sample (e.g., in the presence of a heat stable DNA polymerase) with a pair of amplification primers. One primer of the pair hybridizes to one strand of a target polynucleotide sequence. The second primer of the pair hybridizes to the other, complementary strand of the target polynucleotide sequence. The primers are hybridized to their target polynucleotide sequence strands under conditions such that an extension product of each primer is synthesized which is complementary to each nucleic acid strand. The extension product synthesized from each primer, when it is separated from its complement, can serve as a template for synthesis of the extension product of the other primer. After primer extension, the sample is treated with denaturing conditions to separate the primer extension products from their templates. These steps are cyclically repeated until the desired degree of amplification is obtained. The amplified target polynucleotide can then be used in one of the detection assays described herein to identify the presence or absence of polymorphism of this disclosure.

Because mismatches between the primer sequence and the template sequence can result in inability of the polymerase to extend the primer, and thus failure to generate an amplification product, primers designed to hybridize perfectly with one or more allele can be used to detect such alleles. While mismatches can be designed at any position on the primer, mismatches at the 3' terminal end of the primer are most beneficial as such primers usually cannot be extended by the polymerase. For example, a primer consisting of 21 nucleotides, the first 20 of which are identical to nucleotides 1-20 of SEQ ID NO:6, the $21^{st}$ nucleotide being a cytosine, would successfully produce a PCR amplification product from template DNA comprising SEQ ID NO:3. Alternatively, a primer consisting of 21 nucleotides, the first 20 of which are identical to nucleotides 1-20 of SEQ ID NO:6, the $21^{st}$ nucleotide being a thymidine, would only produce a PCR amplification product from template DNA comprising SEQ ID NO:3 if the SNP of this disclosure were present. Thus, use of such primers would discriminate between DNA comprising wildtype COL6A1 and COL6A1 in which the T allele is present.

The SNP may also be detected using a fragment length polymorphism assay, in which a unique DNA banding pattern based on cleaving the DNA at a series of positions is generated using an enzyme (e.g., a restriction endonuclease). DNA fragments from a sample containing a polymorphism will have a different banding pattern than wild type.

The SNP may also be detected by fragment sizing analysis. Such analysis can be performed using, for example, the Beckman Coulter CEQ 8000 genetic analysis system, a method well-known in the art for microsatellite polymorphism determination.

The SNP may also be detected using a restriction fragment length polymorphism assay (RPLP). The region of interest is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining, or other means know in the art, and compared to controls (wild-type).

The SNP may also be detected using a CLEAVASE fragment length polymorphism assay (CFLP; Third Wave Technologies, Madison, Wis.: see e.g., U.S. Pat. No. 5,888,750). This assay is based on the observation that, when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme is a structure-specific, thermostable nuclease that recognizes and cleaves the junctions between these single-stranded and double-stranded regions. Such assay is exemplified in Oldenburg, M. C., Siebert, M., "New Cleavase Fragment Length Polymorphism Method Improves the Mutation Detection Assay" 2000 Biotechniques 28:351-357.

The SNP may also be detected by hybridization assay, in which the presence or absence of a given allele or mutation is determined based on the ability of the DNA from the sample to hybridize to a complementary DNA molecule (e.g., an oligonucleotide probe). A variety of hybridization assays using a variety of technologies for hybridization and detection are available. The hybridized nucleic acids may be detected using one or more labels attached to the sample nucleic acids. The labels may be incorporated by any of a number of means well known to those of skill in the art. In one embodiment, the label is simultaneously incorporated during the amplification step in the preparation of the sample nucleic acids. For example, PCR can be performed using labeled primers or labeled nucleotides, resulting in a labeled amplification product. Additionally, or alternatively, transcription amplification using a labeled nucleotide (e.g. fluorescein-labeled UTP and/or CTP) incorporates a label into the transcribed nucleic acids. Alternatively, a label may be added directly to the original nucleic acid sample (e.g., mRNA, polyA mRNA, cDNA, genomic DNA etc.) or to the amplification product after the amplification is completed. Means of attaching labels to nucleic acids are well known to those of skill in the art and include, for example, nick translation or end-labeling (e.g. with a labeled RNA) by kinasing the nucleic acid and subsequent attachment (ligation) of a nucleic acid linker joining the sample nucleic acid to a label (e.g., a fluorophore). A label may also be added to the end of fragments using terminal deoxytransferase (TdT).

Detectable labels suitable for use in the methods of this disclosure include any composition detectable by spectroscopic, photochemical, biochemical, immunochemical, electrical, optical or chemical means. Useful labels include, but are not limited to: biotin for staining with labeled streptavidin conjugate; anti-biotin antibodies; magnetic beads (e.g., Dynabeads.TM.); fluorescent, dyes (e.g., fluorescein, Texas Red, rhodamine, green fluorescent protein, and the like); radiolabels (e.g., $H^3$, $I^{125}$, $S^{35}$, $C^{14}$, or $P^{32}$); phosphorescent labels; enzymes (e.g., horse radish peroxidase, alkaline phosphatase and others commonly used in an ELISA); and calorimetric labels such as colloidal gold or colored glass or plastic (e.g., polystyrene, polypropylene, latex, etc.) beads. Other labels are known to those skilled in the art.

Means of detecting such labels are well known to those of skill in the art. Thus, for example, radiolabels may be detected using photographic film or scintillation counters; fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

The label may be added to the target nucleic acid(s) prior to, or after the hybridization. So-called "direct labels" are detectable labels that are directly attached to or incorporated into the target nucleic acid prior to hybridization. In contrast, so-called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids, see Tijssen, 1993, Laboratory Techniques in Biochemistry and Molecular Biology, Vol. 24; Hybridization with Nucleic Acid Probes.

Hybridization of a probe to the sequence of interest (e.g., polymorphism) may be detected directly by visualizing a bound probe (e.g., a Northern or Southern assay; See e.g., Ausabel et al. (Eds.), 1991, Current Protocols in Molecular Biology, John Wiley & Sons, NY). In an example of such assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., agarose gel electrophoresis) and transferred to a membrane. A labeled (e.g., by incorporating a radionucleotide) probe or probes specific for the mutation being detected is allowed to contact the membrane under a condition of low, medium, or high stringency conditions. Unbound probe is removed and the presence of binding is detected by visualizing the labeled probe.

The SNP may also be detected using a DNA chip hybridization assay, in which a series of oligonucleotide probes are affixed to a solid support. The oligonucleotide probes are designed to be unique to a given single nucleotide polymorphism. The DNA sample of interest is contacted with the DNA "chip" and hybridization is detected. An example of such technology is a GeneChip (Affymetrix, Santa Clara, Calif.; see e.g., U.S. Pat. No. 6,045,996) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated from a biological sample obtained from the subject, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Because the sequence and positions of each probe on the array are known, by complementarity, the identity of the target nucleic acid applied to the probe array can be determined.

The SNP may also be detected using a DNA microchip containing electronically captured probes. One example of such technology is a NanoChip (Nanogen, San Diego, Calif.; see e.g., U.S. Pat. No. 6,068,818). Through the use of microelectronics, this technology enables the active movement and concentration charged molecules to and from designated test sites on its semiconductor microchip. DNA capture probes unique to a given polymorphism or mutation are electronically placed at, or "addressed" to, specific sites on the microchip. Since DNA has a strong negative charge, it can be electronically moved to an area of positive charge. First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete. A test sample is then analyzed for the presence of target DNA molecules by determining which of the DNA capture probes hybridize to complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound nonspecifically bound DNA from each site, the polarity or charge of the site is reversed to negative, thereby forcing any unbound or nonspecifically bound DNA back into solution away from the capture probes. A laser-based fluorescence scanner is used to detect binding.

The SNP may also be detected using a "bead array" for the detection of polymorphisms (Illumina, San Diego, Calif.; see e.g., PCT Publications WO99/67641 and WO00/39587, which are herein incorporated by reference). Illumina uses a bead array technology that combines fiber optic bundles and beads that self-assemble into an array. Each fiber optic bundle contains thousands to millions of individual fibers depending on the diameter of the bundle. The beads are coated with an oligonucleotide specific for the detection of a given polymorphism or mutation. Batches of beads are combined to form a pool specific to the array. To perform an assay, the bead array is contacted with a prepared subject sample (e.g., DNA). Hybridization is detected using any suitable method, such as for example, Enzymatic Detection of Hybridization Genomic profiles may be generated using an assay that detects hybridization by enzymatic cleavage of specific structures. One example of such an assay is the INVADER® assay (Third Wave Technologies; see e.g., U.S. Pat. No. 6,001,567, and Olivier, M., The Invader assay for SNP Genotyping, 2005 Mutat. Res. June 3; 573(1-2):103-110, both of which are incorporated herein by reference). The INVADER™ assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with fluorescein that is quenched by an internal dye. Upon cleavage, the dequenched fluorescein labeled product may be detected using a standard fluorescence plate reader.

A MassARRAY system (Sequenom, San Diego, Calif.) may be used to detect polymorphisms (see e.g., U.S. Pat. No. 6,043,031).

Genomic DNA samples are usually, but need not be, amplified before being analyzed. Genomic DNA can be obtained from any biological sample. Amplification of genomic DNA generates a single species of nucleic acid if the individual from whom the sample was obtained is homozygous at the polymorphic site, or two species of nucleic acid if the individual is heterozygous.

RNA samples also are often subject to amplification. In this case, amplification is typically, but not necessarily, proceeded by reverse transcription. Amplification of all expressed mRNA can be performed as described in Innis et al., 1990. Academic Press. "PCR Protocols: A Guide to Methods and Applications"; and Bustin, Absolute quantification of mRNA using real-time reverse transcription polymerase chain reaction assays, Journal of Molecular Endocrinology 25:169-193, 2000. Amplification of an RNA sample from a diploid sample can generate two species of target molecules if the individual providing the sample is heterozygous at a polymorphic site occurring within the expressed RNA, or possibly more if the species of the RNA is subjected to alternative splicing. Amplification generally can be performed using the polymerase chain reaction (PCR) methods known in the art. Nucleic acids in a target sample can be labeled in the course of amplification by inclusion of one or more labeled nucleotides in the amplification mixture. Labels also can be attached to amplification products after amplification (e.g., by end-labeling). The amplification product can be RNA or DNA, depending on the enzyme and substrates used in the amplification reaction.

Once a sample has been analyzed to determine which allele of a polymorphism is present, the individual can be selected, or identified, as having a significantly increased risk of developing a neuromuscular disorder, particularly Ullrich muscular dystrophy, if the SNP of this disclosure is present in one or both alleles of COL6A1.

Therapeutic Compositions

As previously described, the inventors have discovered a newly identified mutation in the COL6A1, that such mutated gene encodes a mutated form of the Type VI collagen alpha 1 chain, and that individuals possessing such mutation develop neuromuscular disorders. Based on this discovery, the inventors have developed a novel method of treatment for the above-described collagen VI-related disorder, the method involving re-directing splicing of the mutated COL6A1 pre-mRNA so that it undergoes normal splicing.

Such methods may be accomplished by administering to the individual a therapeutic compound that binds to the COL6A1 pre-mRNA molecule, thereby preventing use of the newly introduced 5' splice donor site, and forcing the cellular splicing apparatus to use the normal splice donor site (i.e., exon 11 splice donor site) and the normal splice acceptor site (i.e., the exon 12 splice acceptor site). The resulting mature mRNA molecule lacks the afore-mentioned pseudo-exon and thus encodes a normal alpha 1(VI) chain protein.

As used herein, pre-mRNA refers to messenger RNA (mRNA) transcribed from the genome, which has not yet undergone splicing. As used herein, mature mRNA refers to pre-mRNA that has completed the splicing process and is ready to undergo translation to produce the encoded protein.

Figure 6:
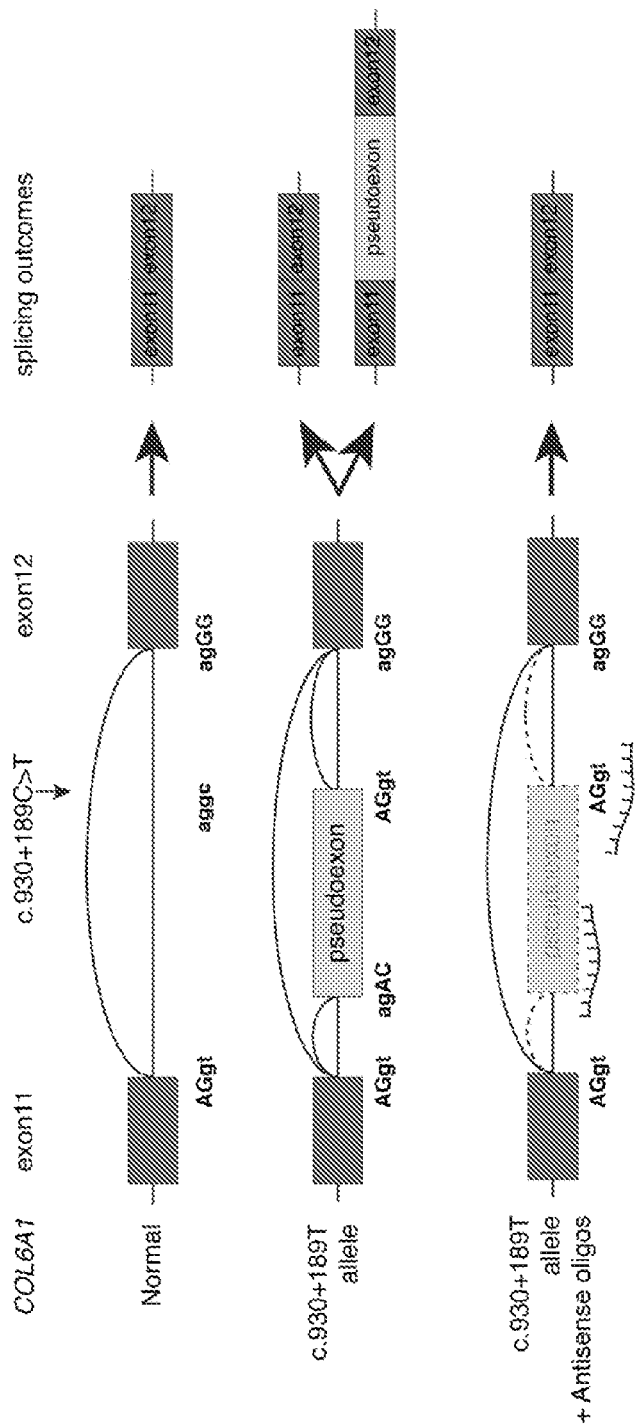
FIG. 6 illustrates the therapeutic approach of using splice modulation to "skip" the mutant exon in the COL6A1 gene in patients with the T allele.
Figure 7:
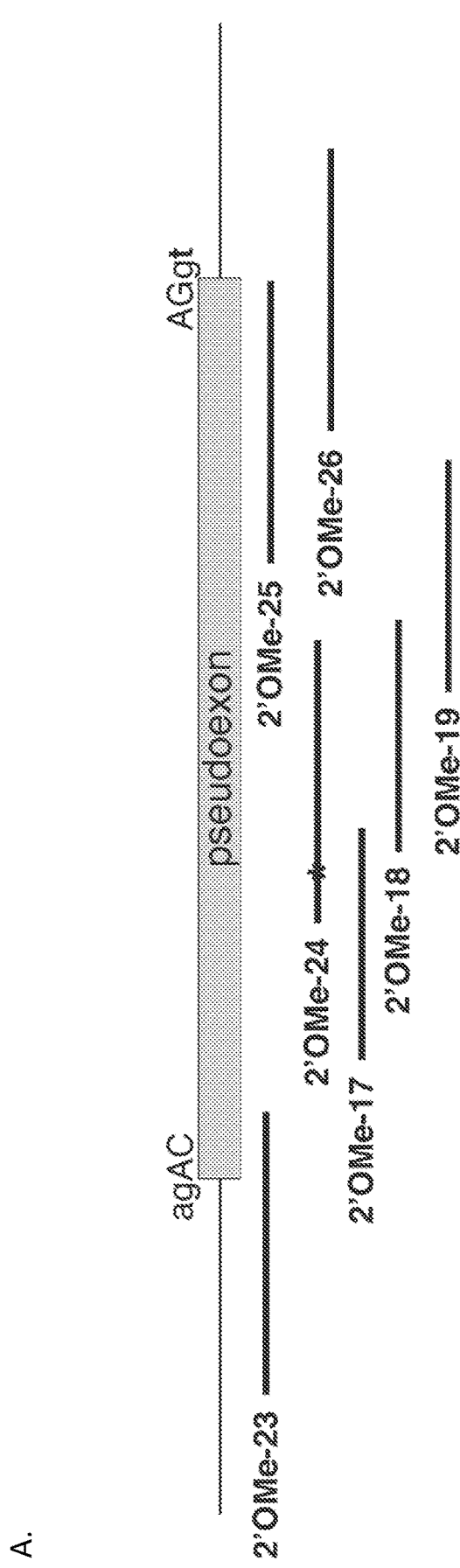
FIGS. 7A-C shows the strategy for design and testing of 2'OMe antisense oligonucleotides (AON).
Figure 7:
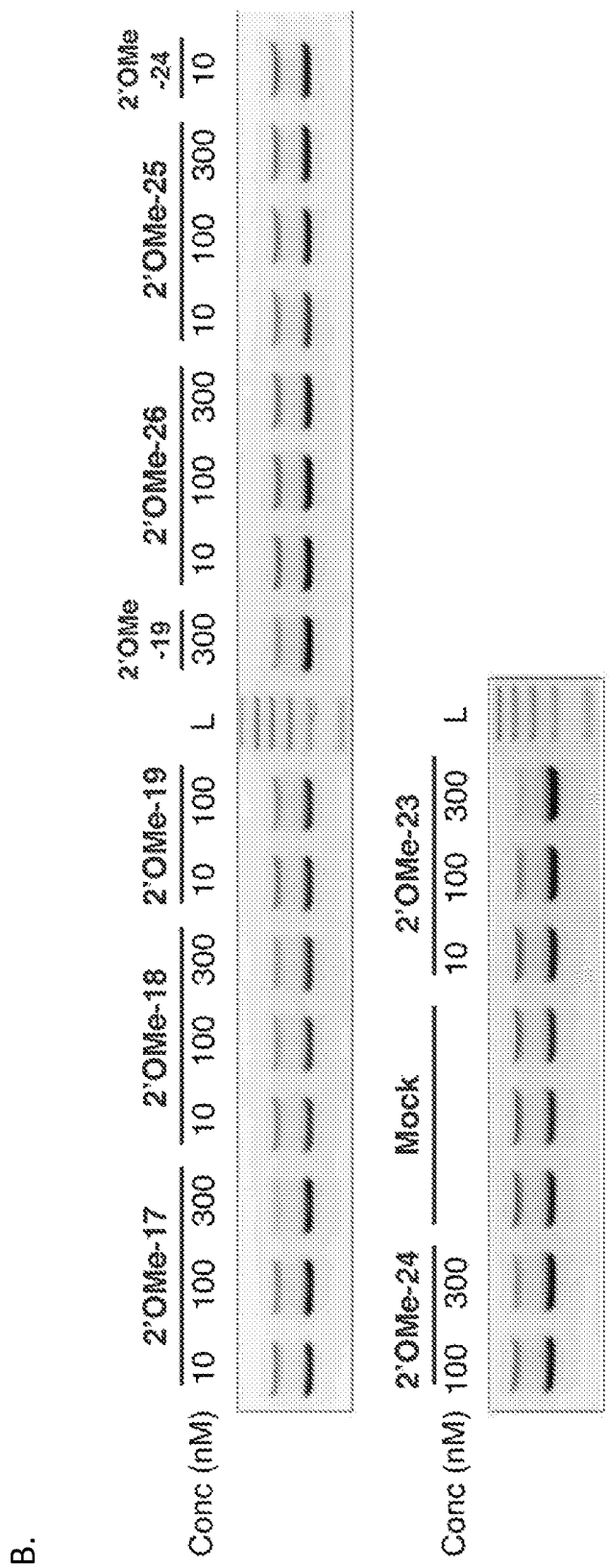
Figure 7:
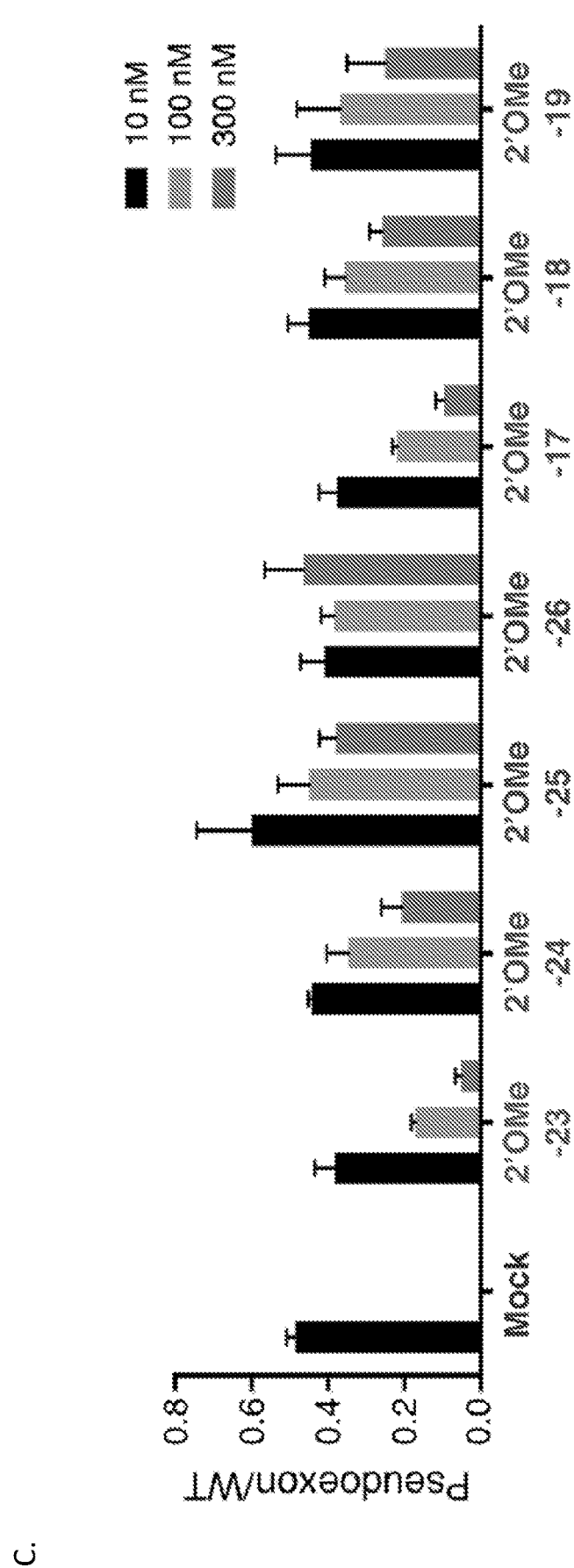

With regard to the present invention, normal splicing refers to joining of the native exon 11 splice donor site to the native exon 12 splice acceptor site. Following normal splicing of wild type COL6A1 pre-mRNA, exon 11 is joined, in-frame, directly to exon 12, with no intervening coding sequence. As used herein, a native splice donor or splice acceptor site is a splice donor, or acceptor, site that is used most commonly, or exclusively, during splicing of a pre-mRNA molecule transcribed from a wild-type (wt) gene. For example, in a pre-mRNA molecule from a wild-type COL6A1 gene, the AGgt at the 3' end of exon 11 is the splice donor site used to join exon 11 to exon 12. The agGG sequence at the 5' end of exon 12 serves as the splice acceptor site for exon 12. After splicing, the splice junction has the sequence AGGG. These sites are illustrated in FIG. 6 (top diagram labeled "normal"). As used herein, a non-native splice donor or splice acceptor site is a splice donor, or acceptor, site that is not present in mRNA transcribed from a wild-type gene, such as wt COL6A1. Non-native splice donor or splice acceptor sites arise because of one or more alterations or mutations in the wild-type gene that result in the formation of a new splice donor or splice acceptor site. For example, as illustrated in FIG. 6, a mutation of the nucleotide at position 189 of intron 11 (SEQ ID NO:3) alters the sequence aggc to aggt, which creates a new splice donor site. This new site is considered a non-native splice donor site. As previously described, the cellular splicing apparatus joins this site with the splice acceptor site at the beginning of exon 12. Consequently, the splice donor site at the 3' end of exon 11, which is normally joined to the exon 12 acceptor site, is joined to an acceptor site 115 bp downstream of the 3' end of exon 11. This downstream acceptor site is referred to as a cryptic site, since it is present in the wt pre-mRNA but is not normally used during splicing.

With regard to this disclosure, aberrant splicing, or mutant splicing, refers to joining of a non-native splice donor, or splice acceptor, site to a native (or non-native) splice donor, or acceptor, site. For example, with regard to the present invention, the 189C>T mutation introduced a non-native splice donor site that is then joined to the exon 12 splice acceptor site. Such splicing can be referred to as aberrant splicing. In addition, aberrant splicing also includes joining of the exon 11 splice donor site to the cryptic splice acceptor lying 115 bp downstream of the 3' end of exon 11. In regard to the present invention, the result of aberrant splicing is that a pseudo-exon is incorporated into the mature COL6A1 mRNA (see FIG. 6).

Antisense technology has been demonstrated to be an effective method of modifying the expression levels of gene products (see, for example, U.S. Pat. Nos. 8,765,703, 8,946,183, and U.S. Patent Publication No. 2015/0376615, incorporated herein by reference in their entirety). Antisense technology works by interfering with known steps in the normal processing of mRNA. Briefly, RNA molecules are transcribed from genomic DNA in the nucleus of the cell. These newly synthesized mRNA molecules, called primary mRNA or pre-mRNA, must be processed prior to transport to the cytoplasm for translation into protein at the ribosome. Such processing includes the addition of a 5' methylated cap and the addition of a poly(A) tail to the 3' end of the mRNA.

Maturation of 90-95% of mammalian mRNAs then occurs with splicing of the precursor (pre-) mRNA. Introns (or intervening sequences) are regions of a primary transcript (or the DNA encoding it) that are not included in the coding sequence of the mature mRNA. Exons (expressed sequences) are regions of a primary transcript (or the DNA encoding it) that remain in the mature mRNA when it reaches the cytoplasm. During the splicing process, exons in the pre-mRNA molecule are spliced together to form the mature mRNA sequence. Splice junctions, also referred to as splice sites, are utilized by cellular apparatus to determine which sequences are removed and where the ends to be joined start and stop. Sequences on the 5' side of the junction are called the 5' splice site, or splice donor site, whereas sequences on the 3' side the junction are referred to as the 3' splice site, or the splice acceptor site. In splicing, the 3' end of an upstream exon is joined to the 5' end of the downstream exon. Thus, the un-spliced RNA (or pre-mRNA) has an exon/intron junction at the 5' end of an intron and an intron/exon junction at the 3' end of an intron. After the intron is removed, the exons are contiguous at what is sometimes referred to as the exon/exon junction or boundary in the mature mRNA. Cryptic splice sites are those which are less often used but may be used when the usual splice site is blocked or unavailable. The use of different combinations of exons by the cell can result in multiple mRNA transcripts from a single gene.

Antisense technology can also be used to affect splicing of a gene transcript. In this application, the antisense oligonucleotide binds to a pre-spliced RNA molecule (pre-messenger RNA or pre-mRNA) and re-directs the cellular splicing apparatus, thereby resulting in modification of the exon content of the spliced mRNA molecule. Thus, the overall sequence of a protein encoded by the modified mRNA differs from a protein translated from mRNA, the splicing of which was not altered. The protein that is translated from the altered mRNA may be truncated and/or it may be missing amino acid sequences. Typically, the compounds used to affect splicing are, or contain, oligonucleotides having a base sequence complementary to the mRNA being targeted. Such oligonucleotides are referred to herein as "antisense oligonucleotides" (AONs).

A therapeutic compound of this disclosure is a compound that, upon administration to an individual possessing the afore-mentioned mutation, results in normal splicing of COL6A1 pre-mRNA molecules, and production of normal alpha 1(VI) chain protein. These therapeutic compounds may comprise antisense oligomers targeted to the COL6A1 pre-mRNA so that the newly introduced splice donor site (i.e., non-native splice site) in the COL6A1 pre-mRNA is not used, and the COL6A1 pre-mRNA molecule undergoes normal splicing.

One aspect of the invention is an antisense oligomer targeted to a sequence in an intron of a COL6A1 pre-mRNA molecule, wherein hybridization of the antisense oligomer to the target sequence in the COL6A1 pre-mRNA molecule results in normal splicing of the COL6A1 pre-mRNA molecule. In certain aspects, the COL6A1 pre-mRNA molecule comprises a non-native splice donor or splice acceptor site in the intron. In certain aspects, the presence of the non-native splice donor or splice acceptor site causes aberrant splicing of the COL6A1 pre-mRNA molecule. In certain aspects, hybridization of the antisense oligomer to the target sequence in the COL6A1 pre-mRNA molecule prevents use of a non-native splice donor or splice acceptor site.

As used herein, an antisense oligomer is a polymeric molecule comprising nucleobases that is capable of hybridizing to a sequence in a nucleic acid molecule, such as a pre-mRNA or mRNA molecule. In this regard, the ability to hybridize represents the antisense activity of the antisense oligomer. The term nucleobase, as used herein, refers to the heterocyclic base portion of a nucleoside. In general, a nucleobase is any group that contains one or more atoms, or groups of atoms, capable of hydrogen bonding to one or more atoms in the base of another nucleoside. In addition to "unmodified" or "natural" nucleobases such as the purine nucleobases adenine (A) and guanine (G), and the pyrimidine nucleobases thymine (T), cytosine (C) and uracil (U), modified nucleobases or nucleobase mimetics known to those skilled in the art are also amenable to the invention. The term "modified nucleobase" refers to a nucleobase that is similar in structure to the parent nucleobase, such as for example, a 7-deaza purine, a 5-methyl cytosine, a G-clamp, or a tricyclic phenoxazine nucleobase mimetic. Methods for preparation of these modified nucleobases are well known to those skilled in the art.

As is known in the art, a nucleoside is a base-sugar combination. The base portion of the nucleoside is normally a heterocyclic base (e.g., a nucleobase or simply a "base"). The two most common classes of such heterocyclic bases are purines and the pyrimidines. Nucleotides are nucleosides that include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage.

The term oligomer includes oligonucleotides, oligonucleosides, oligonucleotide analogs, oligonucleotide mimetics and chimeric combinations thereof. Oligomers of the invention include, but are not limited to, primers, probes, antisense compounds, antisense oligonucleotides, antisense RNA, antisense DNA, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops.

Oligomers may be any length suitable for administering to a cell or individual in order to modulate splicing of an mRNA molecule. For example, antisense oligomers of this disclosure may comprise from about 10 to about 50 nucleobases (i.e. from about 10 to about 50 linked nucleosides). This embodies antisense oligomers of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases. Antisense oligomers of the invention may comprise, or consist of, 10 to 30 nucleobases, or 10 to 25 nucleobases. In one embodiment of the invention, antisense oligomers of the invention comprise, or consists of, 18 nucleobases, 19 nucleobases, 20 nucleobases, 21 nucleobases, 22 nucleobases, 23 nucleobases, 24 nucleobases, 25 nucleobases, 26 nucleobases, 27 nucleobases, 28 nucleobases, 29 nucleobases or 30 nucleobases Methods of determining the optimal length for antisense oligomers of the invention are known to those skilled in the art.

It is understood in the art that RNA molecules often have a short half-life, making their use as therapeutic agents problematic. Thus, it is often preferable to include chemical modifications in oligonucleotides to alter their activity. Chemical modifications can alter oligomer activity by, for example, increasing affinity of an antisense oligomer for its target RNA, increasing nuclease resistance (e.g., resistance to ribonucleases such as RNaseH), and/or altering the pharmacokinetics (e.g. half-life) of the oligomer. Thus, for example, it is possible to replace sugars, nucleobases and/or internucleoside linkages with a group that maintains the ability of the oligomer to hybridize to its target sequence, but which impart one or more desirable characteristics, such as resistance to degradation or increased half-life, to the oligomer. Such groups can be referred to as analogs (e.g., sugar analog, nucleobase analog, etc.). Generally, an analog is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged, achiral linkages. In some instances, an analog is used in place of the nucleobase. Representative nucleobase mimetics are well known in the art and include, but are not limited to, tricyclic phenoxazine analogs and universal bases (Berger et al., Nuc. Acid Res. 2000, 28:2911-14, incorporated herein by reference). Examples of such sugar, nucleoside and nucleobase mimetics are disclosed in U.S. Pat. Nos. 8,765,703 and 8,946,183, both of which are incorporated herein by reference in their entirety). Methods of synthesis of sugar, nucleoside and nucleobase mimetics, and the use of such mimetics to produce oligonucleotides are well known to those skilled in the art.

Oligomers of the invention can also be conjugated to cell-penetrating peptides (CPPs). Such peptides are short peptides that enhance the cellular uptake of oligomers to which they are attached. CPPs and their use to enhance cellular uptake are known to those skilled in the art, and are also described in U.S. Pat. No. 9,303,076, which is incorporated herein by reference.

As used herein, the terms targeted to, targeting, and the like, refer to a process of designing an antisense oligomer so that it specifically hybridizes with a desired nucleic acid molecule, such as a desired pre-mRNA or mRNA molecule. The terms "hybridizes," "hybridization," "hybridize to," and the like, are terms of art that refer to the pairing of nucleobases in complementary strands of oligonucleotides (e.g., an antisense oligomer and a selected/target sequence in a pre-mRNA molecule). While embodiments of this disclosure are not limited to a particular pairing mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is complementary to the natural nucleobases thymidine and uracil, which pair through the formation of hydrogen bonds. Similarly, the natural base guanine is complementary to the natural bases cytosine and 5-methyl cytosine.

In the context of the invention, the phrase "specifically hybridizes" refers to the capacity of an antisense oligomer of the invention to preferentially binds COL6A1 mRNA molecule (e.g., pre-mRNA) rather than binding a mRNA molecule encoding a protein unrelated in structure to the alpha 1 chain of Type VI collagen. Further, an antisense oligomer that preferentially binds a COL6A1 mRNA molecule is one that hybridizes with a sequence in an mRNA encoding alpha 1(VI) chain protein (e.g., an alpha 1(VI) chain pre-mRNA), but which does not significantly hybridize with an mRNA molecule encoding a protein unrelated in structure to an alpha 1(VI) chain protein. In this context, significant hybridization refers to binding of an antisense oligomer of the invention with an affinity or avidity sufficiently high enough to interfere with the ability of the antisense oligomer to achieve the desired effect. Examples of such desired effects include, but are not limited to, modulation of splicing of a COL6A1 pre-mRNA, reduced production of an aberrant alpha 1(VI) chain, increased production in normal alpha 1(VI) chain or a reduction in symptoms of a COL6A1-related disorder. Thus, it will be understood by those skilled in the art that an antisense oligomer is considered specific for a COL6A1 mRNA molecule (i.e., specifically hybridizes with) when there is a sufficient degree of complementarity between the linear sequence of nucleobases in the antisense oligomer and a linear sequence of nucleobases (target sequence) in the mRNA molecule, to avoid significant binding of the antisense oligomer to non-target sequences under conditions in which specific binding is desired (i.e., under physiological conditions in the case of in vivo assays or therapeutic treatment, and under conditions in which assays are performed in the case of in vitro assays).

A used herein, the terms complement, complementary, complementarity, and the like, refer to the capacity for precise pairing between nucleobases in an antisense oligomer and nucleobases in a target sequence. Thus, if a nucleobase (e.g., adenine) at a specific position in an antisense oligomer is capable of hydrogen bonding with a nucleobase (e.g., uracil) at a specific position in a target sequence, then the nucleobases at those specific positions in the antisense oligomer and the target sequence are considered complementary. Usually, the terms complement, complementary, complementarity, and the like, are viewed in the context of a comparison between a defined number of contiguous nucleotides in a first nucleic acid molecule (e.g., an oligomer) and a similar number of contiguous nucleotides in a second nucleic acid molecule (e.g., a mRNA molecule), rather than in a single base to base manner. For example, if an antisense oligomer is 25 nucleotides in length, its complementarity with a target sequence is usually determined by comparing the sequence of the entire oligomer, or a defined portion thereof, with a number of contiguous nucleotides in a target sequence. An oligomer and a target sequence are complementary to each other when a sufficient number of corresponding positions in each molecule are complementary. Positions in two separate nucleic acid molecules are considered corresponding if, when the sequences of the two separate nucleic acid molecules are aligned, the nucleobases at those positions are adjacent to one another. As an example, when comparing the sequence of an oligomer to a similarly sized sequence in a target sequence, the first nucleotide in the oligomer is compared with a chosen nucleotide at the start of the target sequence. The second nucleotide in the oligomer (3' to the first nucleotide) is then compared with the nucleotide directly 3' to the chosen start nucleotide. This process is then continued with each nucleotide along the length of the oligomer. Thus, the terms "specifically hybridizable" and "complementary" are terms which are used to indicate a sufficient degree of precise pairing or complementarity over a sufficient number of contiguous nucleobases such that stable and specific binding occurs between the antisense compound and a target nucleic acid.

Hybridization conditions under which a first nucleic acid molecule will specifically hybridize with a second nucleic acid molecule are commonly referred to in the art as stringent hybridization conditions. It is understood by those skilled in the art that stringent hybridization conditions are sequence-dependent and can be different in different circumstances. Thus, stringent conditions under which an oligomer of the invention specifically hybridizes to a target sequence are determined by the complementarity of the oligomer sequence and the target sequence and the nature of the assays in which they are being investigated. Persons skilled in the relevant art are capable of designing complementary sequences that specifically hybridize to a particular target sequence for a given assay or a given use.

The process of designing an antisense oligomer that is targeted to a nucleic acid molecule usually begins with identification of a target nucleic acid molecule, the expression or splicing of which is to be modulated, and determining the sequence of the target nucleic acid molecule. In the present invention, the target nucleic acid molecule is a COL6A1 pre-mRNA molecule.

The next step in the process of designing an antisense oligomer targeted to COL6A1 pre-mRNA molecule is the identification of a target sequence in the mRNA molecule. As used herein, a target sequence is a nucleic acid sequence in a COL6A1 pre-mRNA molecule to which an antisense oligomer of the invention will specifically hybridize, wherein such binding results in normal splicing of the COL6A1 pre-mRNA molecule. Any sequence in the COL6A1 pre-mRNA molecule can serve as a target sequence, as long as binding of such sequence by the antisense oligomer modulates splicing of the COL6A1 pre-mRNA molecule. Preferably, binding of a target sequence by the antisense oligomer results in normal splicing of the COL6A1 pre-mRNA molecule. Preferred sequences to target are those that result in normal splicing of exon 11 to exon 12. In this regard, the inventors have demonstrated that sequences between exon 11 and exon 12 (i.e., intron 11) in the pre-mRNA molecule can be used as target sequences to effect normal splicing of COL6A1 pre-mRNA molecules.

Once a target sequence has been identified, the antisense oligomer is designed to include a nucleobase sequence sufficiently complementary to the target sequence so that the antisense oligomer specifically hybridizes to the target sequence in the COL6A1 pre-mRNA molecule. It is well known in the art that the greater the degree of complementarity between two nucleic acid sequences, the stronger and more specific is the hybridization interaction. It is also well understood that the strongest and most specific hybridization occurs between two nucleic acid molecules that are fully complementary. As used herein, the term fully complementary refers to a situation when each nucleobase in a nucleic acid sequence is capable of hydrogen binding with the nucleobase in the corresponding position in a second nucleic acid molecule. For example, a nucleic acid molecule having the sequence 5'-ACUGA-3' is fully (100%) complementary to a nucleic acid molecule having the sequence 3'-UGACU-5'. Likewise, a nucleic acid molecule having the sequence 5'-ACUGACACGU-3' is 90% complementary to a nucleic acid molecule having the sequence 3'-UAACUGUGCA-5', and 80% complementary to a nucleic acid molecule having the sequence 3'-UAACUUUGCA-5'. Such examples demonstrate the concept of percent complementarity.

Thus, the targeting sequence may be fully complementary to the target sequence. The antisense oligomer may comprise an at least 6 contiguous nucleobase region that is fully complementary to an at least 6 contiguous nucleobase region in the target sequence. Similarly, the antisense oligomer may comprise an at least 8, 10, 12, 14, 16, 18, 20, 21, 22, 23, 24, 25, 26, or 27-contiguous nucleobase sequence that is fully complementary to an at least 8, 10, 12, 14, 16, 18, 20, 21, 22, 23, 24, 25, 26, or 27-contiguous nucleobase sequence in the respective target sequence.

Each nucleobase in the antisense oligomer may be complementary to the nucleobase at the corresponding position in the target sequence, or only some nucleobases at corresponding positions may be complementary. For example, in an antisense oligomer consisting of 30 nucleotides, all 30 nucleotides can be complementary to a 30 contiguous nucleotide target sequence. Alternatively, a 30-mer antisense oligomer may comprise only 20 contiguous nucleotides that are complementary to 20-contiguous nucleotides in the target sequence, with the remaining 10 nucleotides in the oligomer being mismatched to nucleotides outside of the target sequence. Oligomers of the invention may have a targeting sequence of at least 10, 11, 12, 13, 14, 15, 16, 17, 18, 19, 20, 21, 22, 23, 24, 25, 26, or 27-contiguous nucleobases that are fully complementary to the same number of contiguous nucleobases in the target sequence.

The inclusion of mismatches between nucleobases of an antisense oligomer and nucleobases of a target sequence is possible without eliminating the activity of the oligomer (e.g., modulation of splicing). Moreover, such mismatches can occur at any location in the interaction between the antisense oligomer and the target sequence, so long as the antisense oligomer is capable of specifically hybridizing to the targeted nucleic acid molecule. Thus, antisense oligomers of the invention may comprise up to about 20% of nucleotides that are mismatched, as long as the antisense oligomer specifically hybridizes to the target sequence. Thus, antisense oligomers comprise no more than 20%, 15%, 10%, 5% or 3% mismatches, or less. There may be no mismatches between nucleotides in the antisense oligomer involved in pairing and a complementary target sequence. Preferably, mismatches do not occur at contiguous positions. For example, in an antisense oligomer containing 3 mismatch positions, it is preferred if the mismatched positions are separated by runs (e.g., 3, 4, 5, etc.) of contiguous nucleotides that are complementary with nucleotides in the target sequence The use of percent identity is a common way of defining the number of mismatches between two nucleic acid sequences. For example, two sequences having the same nucleobase pairing capacity (i.e., they are fully complementary) would be considered 100% complementary. Moreover, it should be understood that both uracil and thymidine will bind with adenine. Consequently, two molecules that are otherwise identical in sequence would be considered identical, even if one had uracil at position x and the other had a thymidine at corresponding position x. Percent identity may be calculated over the entire length of the oligomeric compound, or over just a portion of an oligomer. For example, the percent identity of an antisense oligomer to a target sequence can be calculated to determine the capacity of an oligomer comprising the targeting sequence to bind to a nucleic acid molecule comprising the target sequence. The sequence of an antisense oligomer of this disclosure may be at least 80%, 85%, 90%, 95%, 97%, 98%, or 99% complementary over its entire length to a target sequence in a COL6A1 pre-mRNA. In one embodiment, the antisense oligomer is full complementary to a target sequence in a target sequence in a COL6A1 pre-mRNA molecule.

Antisense oligomers of this disclosure need not be identical to the oligomer sequences disclosed herein in order to function similarly to the antisense oligomers described herein. Shortened versions of antisense oligomers disclosed herein, or non-identical versions of the antisense oligomers taught herein, fall within the scope of this disclosure. Non-identical versions are those wherein each base does not have 100% identity with the antisense oligomers disclosed herein. A non-identical version can include at least one base replaced with a different base with different pairing activity (e.g., G can be replaced by C, A, or T). Percent identity is calculated according to the number of bases that have identical base pairing corresponding to the oligomer to which it is being compared. The non-identical bases may be adjacent to each other, dispersed throughout the oligomer, or both. For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art. Thus, antisense oligomers of the invention comprise oligonucleotide sequences at least 80%, 85%, 90%, 92%, 94%, 96%, or 98% identical to antisense oligomer sequences disclosed herein, as long as the antisense oligomers are able to modulate splicing of alpha 1(VI) chain-m pre-mRNA molecule.

Thus, this disclosure provides antisense oligomers targeted to a sequence in a COL6A1 pre-mRNA molecule, wherein binding of the antisense oligomer to the target sequence results in production of a mature a COL6A1 mRNA molecule lacking a pseudo-exon. Binding of the antisense oligomer to the target sequence may result in the production of a mature a COL6A1 mRNA molecule lacking SEQ ID NO:4. Binding of the antisense oligomer to the target sequence may result in production of a mature a COL6A1 mRNA molecule lacking SEQ ID NO:3. Binding of the antisense oligomer to the target sequence may result in the production of a mature a COL6A1 mRNA molecule comprising SEQ ID NO:13. Binding of the antisense oligomer to the target sequence may result in the production of a mature alpha COL6A1 mRNA molecule encoding a normal alpha 1(VI) chain protein. Binding of the antisense oligomer to the target sequence may result in the production of a mature COL6A1 mRNA encoding a alpha 1(VI) chain protein comprising SEQ ID NO:14.

Antisense oligomers may be DNA molecules, RNA molecules, synthetic nucleic acid molecules, and combinations thereof. These antisense oligomers may also comprise a modification selected from the group consisting of a nucleoside modification, an internucleoside modification, a sugar modification, a sugar-internucleoside linkage modification, and combinations thereof. These modifications may reduce degradation by a ribonuclease or may increase the half-life of the antisense oligomer. The antisense oligomer may be a morpholino oligomer.

The antisense oligomer may consist of between 9 and 51 nucleosides, or between 14 and 26 nucleosides, including each integer nucleotide length between 9 and 51 nucleosides.

As has been described, the target sequence is a sequence which, if bound by the antisense oligomer, can modulate splicing of exon 11 and exon 12 sequences in an alpha 1(VI) chain pre-mRNA molecule. As such, the target sequence may be located in any region of the alpha 1(VI) chain pre-mRNA, as long as it causes the desired effect. Thus, the target sequence may be located in intron 11 in the alpha 1(VI) chain pre-mRNA. The target sequence can, but need not include, any nucleobases from exon 11 or exon 12. The target sequence does not necessarily comprise SEQ ID NO:1 or SEQ ID NO:7. The target sequence may be located in intron 11. The target sequence may be located within a sequence at least 90%, 95%, 97%, or 99% identical to SEQ ID NO:3. The target sequence may be located within a sequence consisting of SEQ ID NO:3, SEQ ID NO:4, or SEQ ID NO:6.

The target sequence may be at least 90%, 95%, 97% or 99% identical to a sequence selected from the group consisting of SEQ ID NO:23, SEQ ID NO:24, SEQ ID NO:25, NO:26, SEQ ID NO:27, SEQ ID NO:28, SEQ ID NO:29, SEQ ID NO:30, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, and SEQ ID NO:58. The target sequence may comprise a sequence selected from the group consisting of SEQ ID NO:23, SEQ ID NO:24, SEQ ID NO:25, NO:26, SEQ ID NO:27, SEQ ID NO:28, SEQ ID NO:29, SEQ ID NO:30, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, and SEQ ID NO:58

The antisense oligomer may comprise a sequence at least 90%, 95%, 97% or 99% identical to a sequence selected from the group consisting of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, and SEQ ID NO:44. The antisense oligomer may comprise a sequence selected from the group consisting of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, or SEQ ID NO:44.

Antisense oligomers comprise a nucleic acid sequence sufficiently complementary to a target sequence in a COL6A1 pre-mRNA molecule such that the antisense oligomer specifically hybridizes to the target sequence resulting in normal splicing of the COL6A1 pre-mRNA molecule. As used herein, the phrase sufficiently complementary refers to a situation in which the number of nucleobases in the antisense oligomer that are complementary to the nucleobases at corresponding locations in the target sequence is high enough that the antisense oligomer specifically hybridizes with the target sequence. Those skilled in the art will understand that in such a situation, the nucleic acid sequence in the antisense oligomer and the nucleic acid sequence in the target sequence have a high degree of complementarity.

Thus, the nucleic acid sequence in the antisense oligomer and the nucleic acid sequence in the target sequence may be at least 90%, 95%, 97%, 99%, or 100% complementary. Hybridization of the nucleic acid sequence in the oligomer to the target sequence may result in production of a mature COL6A1 mRNA lacking SEQ ID NO:4. Hybridization of the nucleic acid sequence in the oligomer to the target sequence may result in the production of a mature COL6A1 mRNA lacking SEQ ID NO:3, SEQ ID NO:9, or SEQ ID NO:12. Hybridization of the nucleic acid sequence in the oligomer to the target sequence may result in the production of a mature COL6A1 mRNA comprising SEQ ID NO:13. Hybridization of the nucleic acid sequence in the oligomer to the target sequence may result in the production of a mature COL6A1 mRNA encoding a normal alpha 1(VI) chain protein. Hybridization of the nucleic acid sequence in the oligomer to the target sequence may result in the production of a mature COL6A1 mRNA encoding an alpha 1(VI) chain protein comprising SEQ ID NO:14.

This disclosure includes expression vectors comprising, or encoding, an antisense oligomer of the invention. As used herein, an "expression vector" is a nucleic acid molecule comprising a polynucleotide sequence functionally linked to a promoter, such that transcription of the polynucleotide sequence by a polymerase results in production of an antisense oligomer of the invention. Exemplary expression vectors include polynucleotide molecules, preferably DNA molecules, that are derived, for example, from a plasmid, bacteriophage, yeast or virus (e.g., adenovirus, adeno-associated virus, lentivirus, retrovirus, etc.), into which a polynucleotide can be inserted or cloned. Suitable expression vectors are known to those skilled in the art.

This disclosure also includes pharmaceutical compositions comprising an antisense oligomer or expression vector of the invention. Such compositions are suitable for the therapeutic delivery of antisense oligomers, or expression vectors, described herein. Hence, the invention provides pharmaceutical compositions that comprise a therapeutically-effective amount of one or more of the antisense oligomers or expression vectors described herein, formulated together with one or more pharmaceutically-acceptable carriers (additives) and/or diluents. While it is possible for an antisense oligomer or expression vector of the invention to be administered alone, it is preferable to administer the compound as a pharmaceutical composition.

Pharmaceutical compositions of the invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) inhaled into the lungs, for example, by nebulizer or aerosol inhaler; or (9) nasally. Examples of suitable carriers, additives and diluents are described in U.S. Patent Publication No. 2015/0361428, which is incorporated herein by reference in its entirety.

As previously described, the inventors have discovered that the afore-mentioned C>T mutation results in aberrant splicing of a COL6A1 pre-mRNA. Moreover, the inventors have described antisense oligomers that are capable of altering splicing of the mutated pre-mRNA, thereby causing normal splicing of the mutated COL6A1 pre-mRNA. Thus, one embodiment of the invention is a method for restoring normal splicing of a mutated COL6A1 pre-mRNA in a cell comprising the 189C>T mutation in its COL6A1 gene, the method comprising contacting the cell with an antisense oligomer of the invention.

Because the afore-mentioned aberrant splicing of the COL6A1 pre-mRNA leads to the development of neuromuscular disorders, the compounds and methods disclosed herein for restoring normal splicing of the mutant pre-mRNA can be used for treating individuals at risk for, or that have been diagnosed as having, such disorders. Thus, this disclosure provides methods for restoring normal splicing of mutated COL6A1 pre-mRNA in an individual having the 189C>T mutation in their COL6A1 gene, comprising administering to the individual an antisense oligomer of the invention. This disclosure also provides a method for treating an individual having the 189C>T mutation in their COL6A1 gene, comprising administering to the individual an antisense oligomer of this disclosure. This disclosure also provides methods for treating an individual suspected of having a neuromuscular disorder, the method comprising administering to the individual an antisense oligomer of the invention. This disclosure also provides methods for treating an individual diagnosed as having a neuromuscular disorder, comprising administering to the individual an antisense oligomer of the invention.

As used herein, the terms individual, subject, patient, and the like, are meant to encompass any mammal that expresses alpha 1(VI) chain protein, with a preferred mammal being a human. The terms individual, subject, and patient by themselves do not denote a particular age, sex, race, and the like. Thus, individuals of any age, whether male or female, are intended to be covered by this disclosure. Likewise, the methods of this disclosure can be applied to any race of human, including, for example, Caucasian (white), African-American (black), Native American, Native Hawaiian, Hispanic, Latino, Asian, and European. Such characteristics may be significant, and in such cases, the significant characteristic(s) (e.g., age, sex, race, etc.) will be indicated. Additionally, the term "individual" encompasses both human and non-human animals. Suitable non-human animals to which antisense oligomers of the invention may be administered include, but are not limited to companion animals (i.e. pets), food animals, work animals, or zoo animals. Preferred animals include, but are not limited to, cats, dogs, horses, ferrets and other Mustelids, cattle, sheep, swine, and rodents.

Antisense oligomers of the invention may be administered to an individual by any suitable route of administration. Examples of such routes include, but are not limited to, oral and parenteral routes, (e.g., intravenous (IV), subcutaneous, intraperitoneal (IP), and intramuscular), inhalation (e.g., nebulization and inhalation) and transdermal delivery (e.g., topical). It is appreciated that any methods effective to deliver an antisense oligomer into the bloodstream of an individual are also contemplated. For example, transdermal delivery of antisense oligomers may be accomplished by use of a pharmaceutically acceptable carrier adapted for topical administration. Antisense oligomers can be administered in the absence of other molecules, such as proteins or lipids, or they be administered in a complex with other molecules, such as proteins or lipids. For example, the use of cationic lipids to encapsulate antisense oligomers is disclosed in U.S. Pat. Nos. 8,569,256, and 6,806,084, which are incorporated herein by reference in their entirety. Similarly, the use of peptide-linked morpholino antisense oligonucleotides is disclosed in U.S. Patent Publication No. 2015/0238627, which is incorporated herein by reference.

Screening Vectors

Figure 4:
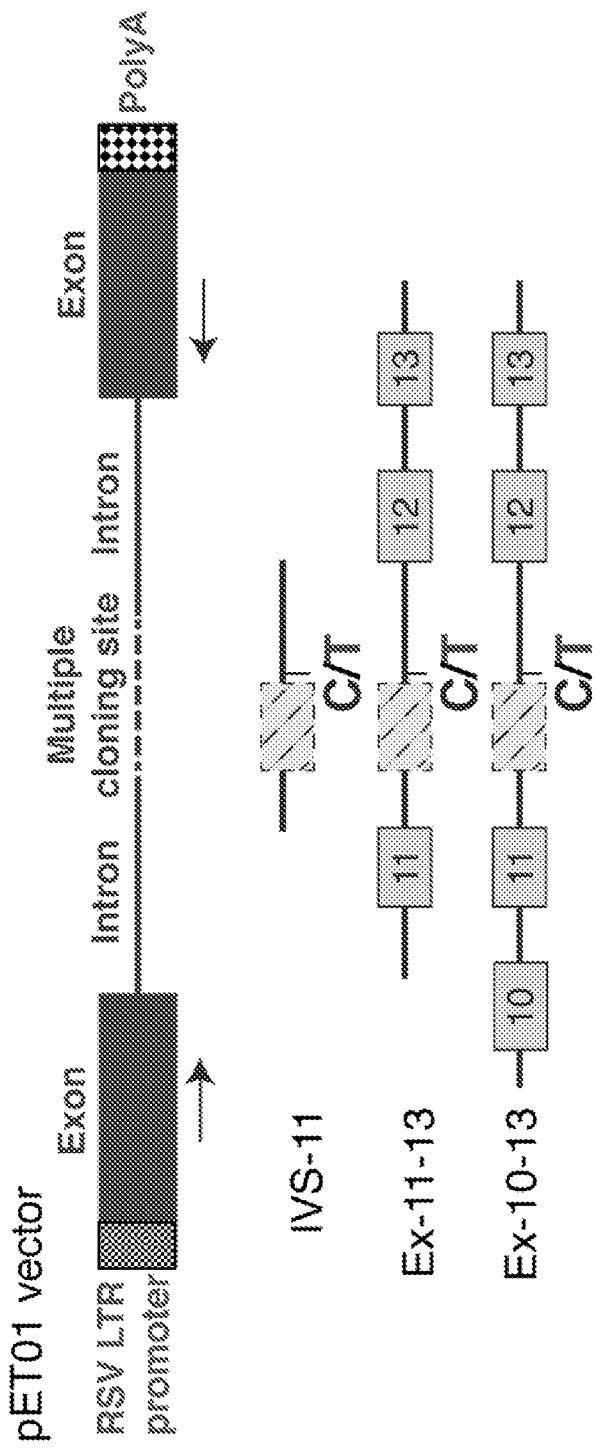
FIG. 4 is an illustration of the reporter constructs ("minigene" constructs) prepared from portions of the COL6A1 genomic DNA sequence.
Figure 5:
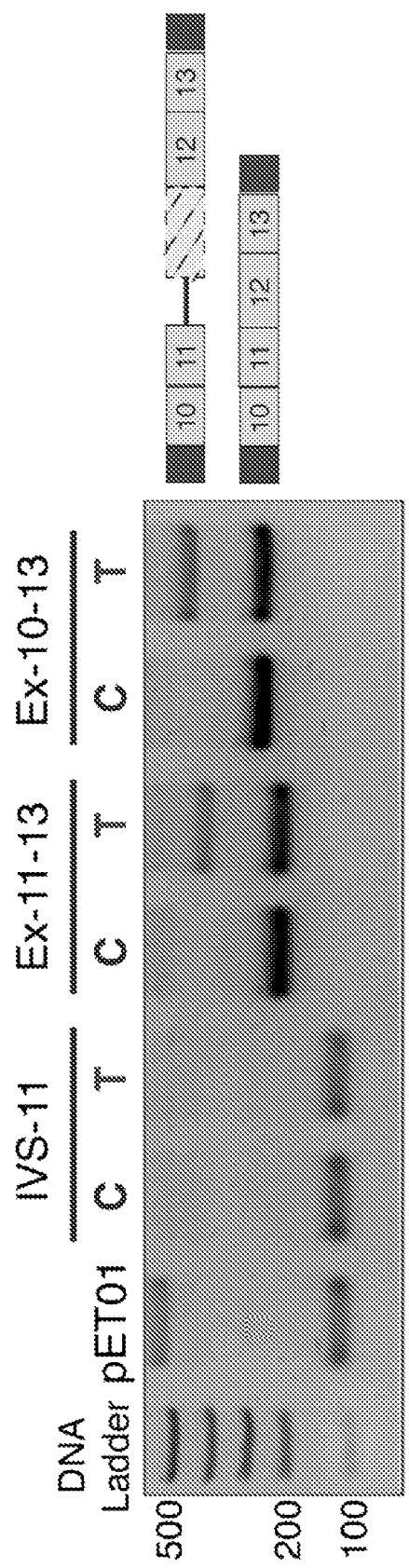
FIG. 5 shows an analysis of the effect of the T allele on splicing from the reporter constructs illustrated in FIG. 4. Expressing the splicing reporters in HEK293T cells demonstrated aberrant splicing only on the reporter constructs carrying the mutant ("T") allele.

As previously described, a spontaneous mutation in intron 11 of COL6A1 results in aberrant splicing of pre-mRNA transcribed from the gene. More specifically, substitution of the cytosine at position 189 of intron 11 (SEQ ID NO:3) with a thymidine introduces a new 5' donor splice site into the COL6A1 pre-mRNA. The cellular splicing apparatus joins the newly created donor site to the exon 12 acceptor site, resulting in introduction of an in-frame pseudo-exon into the mature mRNA. Consequently, the mature COL6A1 mRNA is 72 nucleotides longer than mature mRNA from a gene encoding a wild-type alpha 1(VI) chain. The inventors have discovered that this altered splicing pattern, and the resulting difference in size between mature wild-type mRNA and mature mutant mRNA, can be used to test compounds for their ability to cause normal splicing of COL6A1 pre-mRNA. In particular, the inventors have constructed vectors comprising the mutant intron 11 (i.e., intron 11 containing 189C>T) flanked by exon 11 and exon 12. The exon 11-intron 11:189C>T-exon 12 construct is functionally linked to a promoter sequence. When the construct is introduced into a cell, the exon 11-intron 11:189C>T-exon 12 sequence is transcribed into pre-mRNA, which is then spliced to produce the mutant mRNA comprising the pseudo-exon. This product can be detected using, for example, hybridization assays, or PCR primers that bind to sequences flanking the exon 11-intron 11:189C>T-exon 12 sequence. When an antisense oligomer capable of modulating splicing is introduced into the cell, it binds to the pre-spliced mRNA thereby blocking the new 5' donor splice site in the intron. The cellular splicing machinery then joins exon 11 to exon 12, resulting in normal splicing of exon 11 and exon 12. This normally-spliced mRNA lacks the pseudo-exon and is therefore smaller in size than the mutant spliced mRNA. Thus, a PCR product produced from the normally spliced mRNA will be shorter than a product produced from the mutant spliced mRNA, using the same primers. Such constructs and their principle of operation are shown in FIGS. 4 and 5.

Thus, this disclosure also provides recombinant nucleic acid molecules comprising an insert containing at least a portion of intron 11 (e.g., comprising SEQ ID NO:6), wherein the portion of intron 11 is flanked by at least a 3' splice acceptor site and at least a 5' splice donor site, the insert being operationally linked to a promoter sequence. The portion of intron 11 is flanked by at least a portion of a COL6A1 exon 11 comprising the donor site, and at least a portion of COL6A1 exon 12 comprising the acceptor site. The at least a portion of exon 11 may be 5' to the portion of intron 11. The at least a portion of exon 12 may be 3' of the portion of intron 11. The at least a portion of exon 11 may comprise SEQ ID NO:59. The at least a portion of exon 11 may comprise SEQ ID NO:1. The at least a portion of exon 12 may comprise SEQ ID NO:60. The at least a portion of exon 12 may comprise SEQ ID NO:7. Examples of such constructs are shown in FIGS. 4, 5 and 6.

These constructs may be used in the methods of this disclosure to determine if a compound is capable modulating splicing of exon 11 and exon 12 of COL6A1 pre-mRNA. These methods include: introducing a test antisense oligomer into a cell comprising a recombinant expression vector of the invention; performing a first polymerase chain reaction (PCR) assay on nucleic acid molecules obtained from the cell, using a set of primers that bind sequences flanking the 3' splice acceptor-intron 11 portion-5' splice donor insert; and comparing the size of the PCR product with a PCR product produced from a second PCR assay performed on a second cell comprising the recombinant expression vector but lacking the test antisense oligomer, and using the same pair of primers. If the PCR product produced from the first PCR assay is smaller than the PCR product produced in the second PCR assay, it may be concluded that the test antisense primer is capable of modulating splicing of exon 11 and exon 12 of COL6A1 pre-mRNA.

Once compounds that affect COL6A1 pre-mRNA splicing (e.g., cause normal splicing of COL6A1 pre-mRNA) have been identified (e.g., by using the disclosed screening vectors), the effectiveness of such compounds can be tested in whole organisms. Thus, the present disclosure also provides transgenic animals comprising a Col6a1 locus comprising the disclosed c.930+189C>T mutation. In one aspect, the transgenic animal has been engineered to comprise the c.930+189C>T mutation, or to comprise a mutation at the corresponding location in the animal's genome. In one aspect, the animal is a mouse. Such a mouse can be engineered so that the mouse gene contains the c.930+189C>T mutation, or a mutation at the corresponding location (e.g., in the COL6A1 intron 11). In one aspect, the animal has been engineered so that a portion of the mouse Col6a1 locus has been replaced with the corresponding portion from the human genome. For example, the region of the mouse Col6a1 locus spanning exon 9 to exon 14 may be replaced with the human counterpart. In one aspect, the human counterpart comprises the c.930+189C>T mutation. Mice may also be produced in which a portion of the mouse Col6a1 locus has been replaced with the corresponding portion from the genome of a human having a normal Col6a1 locus (i.e., lacking the c.930+189C>T mutation). Also provided are guide RNAs for producing transgenic animals of the invention.

Kits

Also included in this disclosure are kits useful for practicing the disclosed methods. A kit for determining the likelihood of developing a neuromuscular disorder, in accordance with the methods of this disclosure may include: i) reagents for selectively detecting the presence or absence of the SNP of this disclosure in a nucleic acid sample isolated from a biological sample obtained from an individual tested and ii) instructions for using the kit. Thus, such kit may be used for determining the risk of an individual to develop a neuromuscular disorder, or to determine the risk of an individual to develop Ullrich muscular dystrophy. Such kit may also be used for confirming a diagnosis, or suspected diagnosis of Ullrich muscular dystrophy in an individual.

These kits may also contain at least some of the reagents required to determine the presence or absence of particular alleles of this disclosure. Reagents for these kits may include, but are not limited to, an isolated nucleic acid, preferably a primer, a set of primers, or an array of primers, as described elsewhere herein. The primers may be fixed to a solid substrate. The kits may further comprise a control target nucleic acid and primers. One skilled in the art will, without undue experimentation, able to select primers in accordance with the requirements of the detection methods to be utilized. The isolated nucleic acids of the kit may also comprise a molecular label or tag. Usually, the primer, set of primers, or array of primers, are directed to detect the presence or absence of at least one allele of the SNP of this disclosure.

This disclosure also provides kits for testing compounds for their ability to modulate splicing of COL6A1 pre-mRNA. Such kits can comprise screening vectors of the invention, related probes, and relates primers. Such kits may also comprise control compounds, such as oligomers, that are known to modulate splicing COL6A1 pre-mRNA. Examples of such oligomers are disclosed herein.

This disclosure also provides kits for modulating splicing of COL6A1 pre-mRNA, and/or treating an individual suspected of having, or diagnosed as having a neuromuscular disorder, the kit comprising at least one antisense oligomer of the invention or a vector encoding at least one antisense oligomer of the invention. The kit may also comprise instructions for using the kit, and various reagents, such as buffers, necessary to practice the methods of the invention. These reagents or buffers may be useful for administering an antisense oligomer of the invention to a cell or an individual.

The kit may also comprise any material necessary to practice the methods of the invention, such as syringes, tubes, swabs, and the like.

These kits may also comprise various reagents, such as buffers, necessary to practice the methods of this disclosure. These reagents or buffers may, for example, be useful to extract and/or purify the nucleic from the biological sample obtained from the individual to be tested. The kit may also comprise all the necessary materials such as microcentrifuge tubes necessary to practice the methods of this disclosure.

EXAMPLES

Example 1. Discovery of an Intronic Mutation in the COL6A1 Gene

Figure 2:
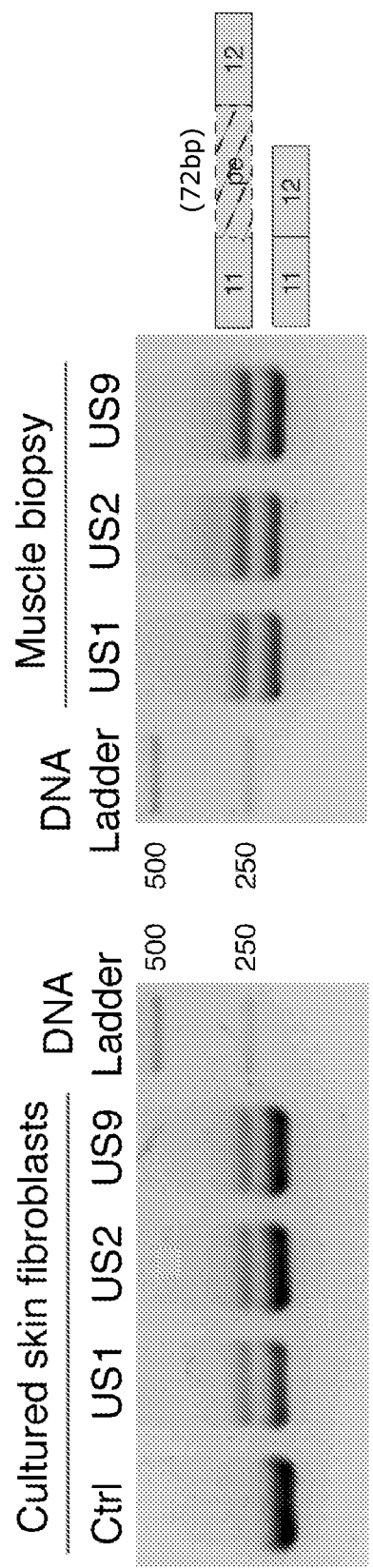
FIG. 2 shows confirmation that the mutation correlates with insertion of a 72 bp, intronic sequence into the mature mRNA. The pseudo-exon inclusion was detected with reverse transcriptase (RT)-PCR in patient-derived skin fibroblasts and muscle biopsy, and showed low abundance as compared to the normal allele.

RNA-sequencing (RNA-seq) and whole genome sequencing (WGS) in undiagnosed collagen VI-like patients at the NIH identified a new intronic mutation in COL6A1. Patients with a clinical and biochemical presentation of collagen VI-related disorder, but for whom no mutation had been identified by routine genetic testing, were selected for whole-transcriptome analysis. Two muscle RNA samples were sent for RNA-sequencing, and analyzed for variations in gene expression and splicing events. For the two patients (US6 and US8), a new splicing event was identified in COL6A1 intron 11, which leads to the retention of a 72-bp intronic sequence between exons 11 and 12 (FIG. 1). This splicing event was not observed in control samples. Genomic DNA from patient US6 was further analyzed by WGS, and a heterozygous variant was identified adjacent to the 5' splice site of the new splicing event (FIG. 1). This variant was absent in all control genomes sequenced. The mutation (NM_001848 c.930+189C>T) predicts the creation of a 5' donor splice site (aggc>AGgt; Human Splicing Finder Matrices splicing site motif strength of 50.23 vs 77.07 for C and T alleles, respectively), likely causing the retention of the intronic sequence. The retention of the 72-bp pseudo-exon sequence was validated by RT-PCR in RNA samples isolated from patients' muscle biopsies and cultured fibroblasts (FIG. 2). The retention of the pseudo-exon occurs at the N-terminal end of the triple helical domain of alpha 1(VI) collagen, and by its position would not affect the cysteine residues important for monomer dimerization, nor the critical region important for assembly. The retention of the pseudo-exon instead predicts a dominant-negative mechanism of action for this mutation, similar to the most common exon deletion and glycine mutations.

Figure 3:
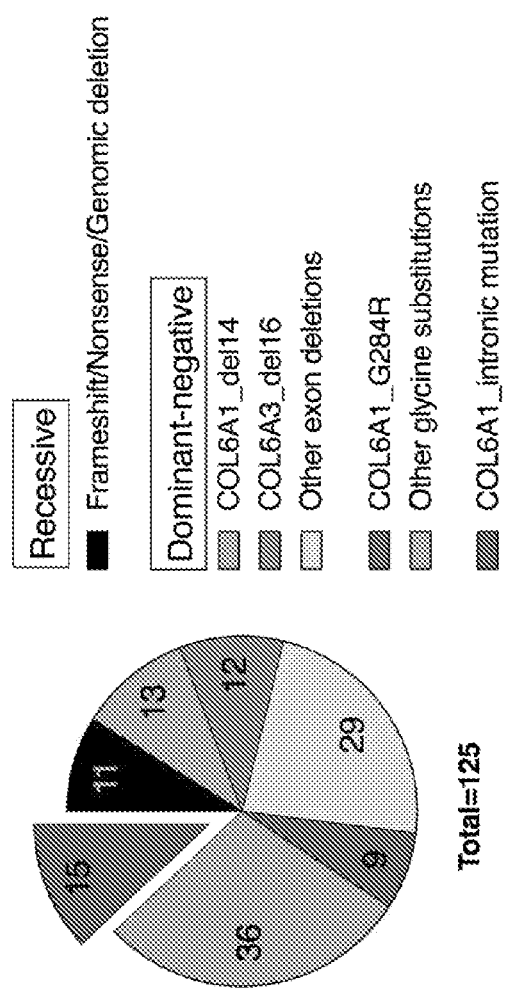
FIG. 3 shows the frequency in the NIH cohort of known mutations in COL6 genes, as well as the COL6A1 intronic mutation of this disclosure. In the NIH cohort, the COL6A1 intronic mutation was the most common mutation.

Example 2. Frequency and Clinical Effect of the Intronic Mutation in the COL6A1 Gene The intronic COL6A1 mutation was the most common molecular defect associated with severe COL6-RD in the NIH cohort. By investigating the NIH cohort of molecularly unconfirmed collagen VI-like patients, the inventors uncovered a total of 15 cases carrying the intronic mutation (C>T) on one allele. Similarly, additional cohorts of patients from Utah, Italy, France and the UK were screened and identified this new intronic mutation in as many additional patients. In the NIH cohort, the intronic mutation was the single most common molecular defect associated with severe COL6-RD, surpassing the COL6A3 deletion of exon 16 mutation (n=12), also associated with a severe Ullrich phenotype (FIG. 3).

This mutation is associated with a severe phenotype, typical of dominant-negative mutations, causing Ullrich muscular dystrophy, although with a delayed onset. On histology, the main findings were the increased degeneration/regeneration, increased centrally localized nuclei. Immunohistofluorescence showed absence of colocalization of collagen VI to the basement membrane. The phenotype of dermal fibroblasts was fairly normal for all cases tested, with only slight reduction of matrix deposition, and slight intracellular retention. When parental DNA samples were available (five or more cases total), segregation analyses showed that this mutation was de novo in all cases. Despite lack of prominent neonatal symptoms, all patients progressed to Ullrich congenital muscular dystrophy (UCMD), the severe end of the COL6-RD spectrum (wheelchair dependence beginning at 7-10 years, respiratory insufficiency with nocturnal non-invasive ventilation started by teenage years).

Example 3. Expression of the Intronic Mutation in the COL6A1 Gene

The intronic mutation creates a new 5' splice donor that can be used as an alternative splicing site. Using end-point PCR and gel quantification, the inventors found that the level of expression of the mutant allele was lower than the expression level from the normal allele in all individuals tested (FIG. 2). In muscle biopsies, the expression was on average around 26% of total COL6A1 expression (FIG. 2), whereas in cultured dermal fibroblasts, it was on average of 9% (FIG. 2). The low levels of expression of the mutant allele is consistent with the mild matrix dysfunction in cultured cells, but is unexpected for a dominant-negative mutation associated with severe clinical hallmarks.

Example 4. Expression of the Pseudo-Exon Transcripts

To verify whether the low levels of expression of the pseudo-exon transcripts could be the result of an alternative usage of the mutant 5' splice site, one patient (US14) was identified who carried an exonic polymorphism in close proximity to the pseudo-exon insertion site (r51980982 T>C in exon 15), which can be used to track the allelic origin of transcript isoforms. Sequencing of gel-separated RT-PCR products showed that pseudo-exon-containing transcripts were derived solely from the T allele of rs1980982, but that normal transcripts (i.e. excluding the pseudo-exon insertion) originated from both the C and T alleles, suggesting that the mutant splice donor site in intron 11 is alternatively used to include or exclude the pseudo-exon (Data not shown; the alternative usage of the mutant splice site is illustrated in FIG. 6).

Example 5. Effect of the Intronic Mutation on Splice Site Selection

To gain further insight into the splicing behavior of the intronic mutation, three different minigene constructs were prepared that used an exon-trap vector (pET01): one containing the intron 11 sequence (pET+Int-11), one containing exons 11 to 13 (pET+Ex-11-13), and one containing exons 10 to 13 (pET+Ex-10-13), each in both normal and mutant versions (FIG. 4). Expression of pET+Int-11 in different cell types did not result in the inclusion of the pseudo-exon, whereas expression of pET+Ex-11-13 did result in an alternative splicing event, as seen by the presence of an additional PCR product (FIG. 5). But this splicing event was different than the one found in the patient samples, as it used a different 3' acceptor splice site. These results confirm that the intronic mutation does create a donor splice site.

Figure 8:
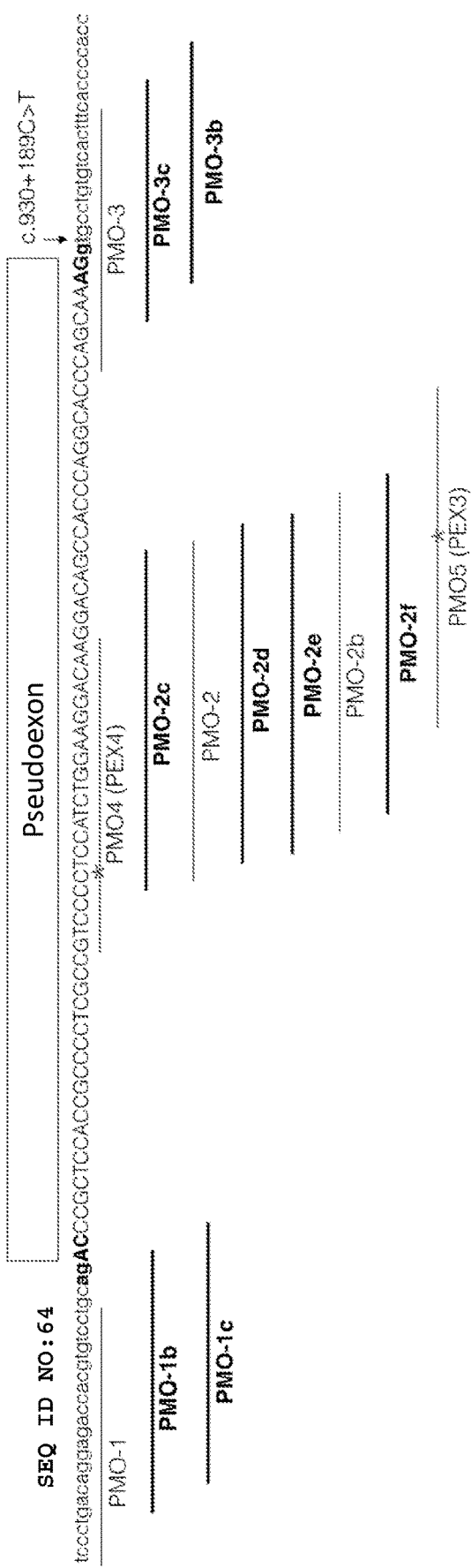
FIGS. 8A-8C.
Figure 8:
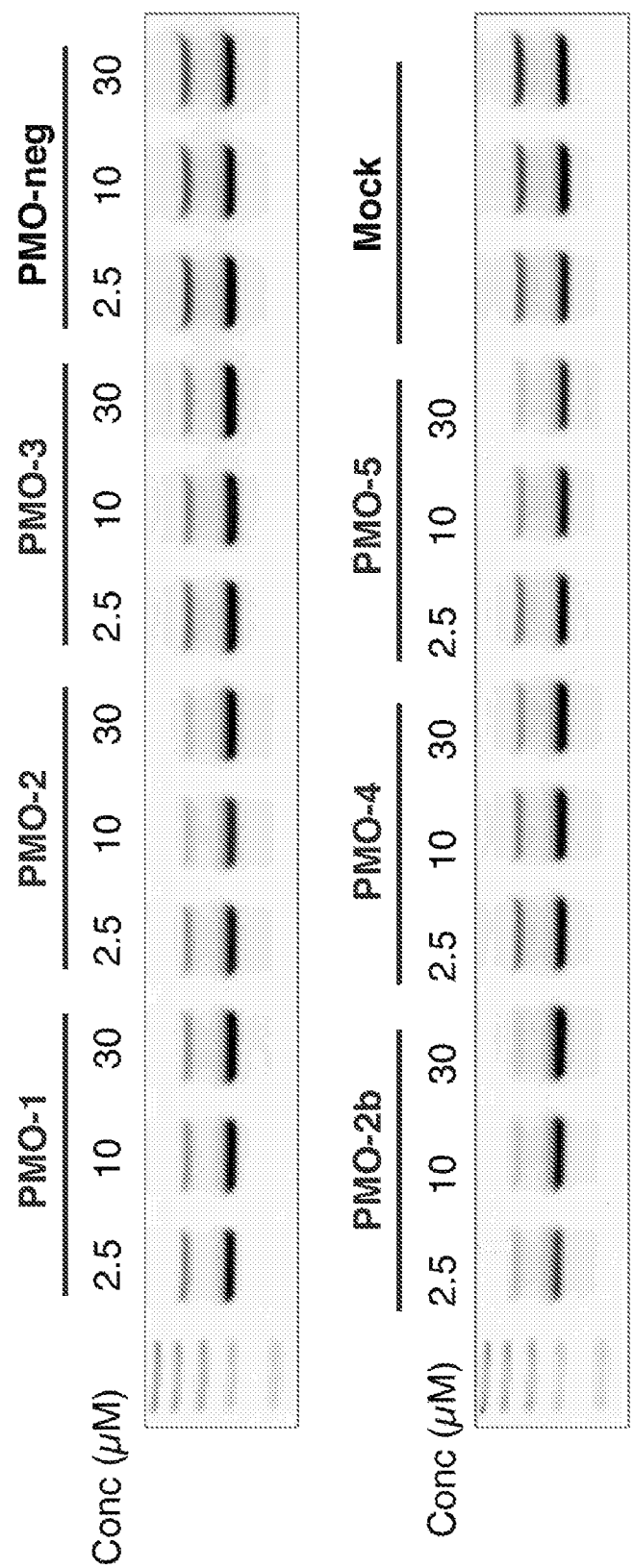
Figure 8:
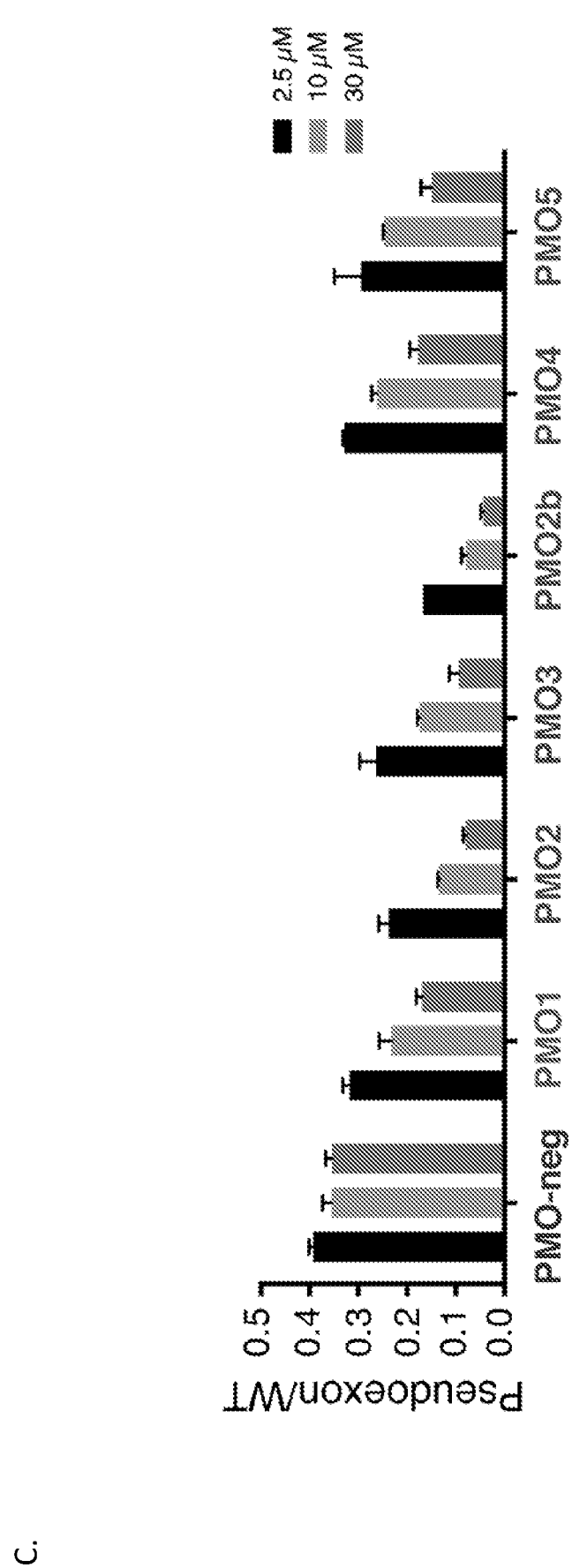

Example 6. Effect of Morpholino Antisense Oligonucleotides on Pseudo-Exon Exclusion Splice-switching oligonucleotides can suppress a pseudo-exon inclusion. To test whether antisense oligonucleotides could be used to exclude the COL6A1 intron 11 pseudo-exon, the inventors designed phosphorothioate morpholino antisense oligonucleotides (PMO) targeting different locations: either the splice acceptor site (PMO-1, PMO-1b, PMO1-c), the splice donor site (PMO-3, PMO-3b, PMO-3c) or within the pseudo-exon, at a predicted splicing enhancer site (PMO-2, PMO-2b, PMO-2c, PMO-2d, PMO-2e, PMO-2f, PMO-4, PMO-5) (FIG. 8A). PMO treatment of pET-Ex-11-13-transfected cells showed that PMO-2 and PMO-2b were the most effective at suppressing the pseudo-exon inclusion (FIG. 8B, FIG. 8C), whereas PMO-1 and PMO-3 had only mild effect on the splicing outcome (FIG. 8B). The target sequences of PMO-2 and PMO-2b contain several predicted binding sites for splicing enhancer factors SRSF2 and SRSF6.

Figure 9:
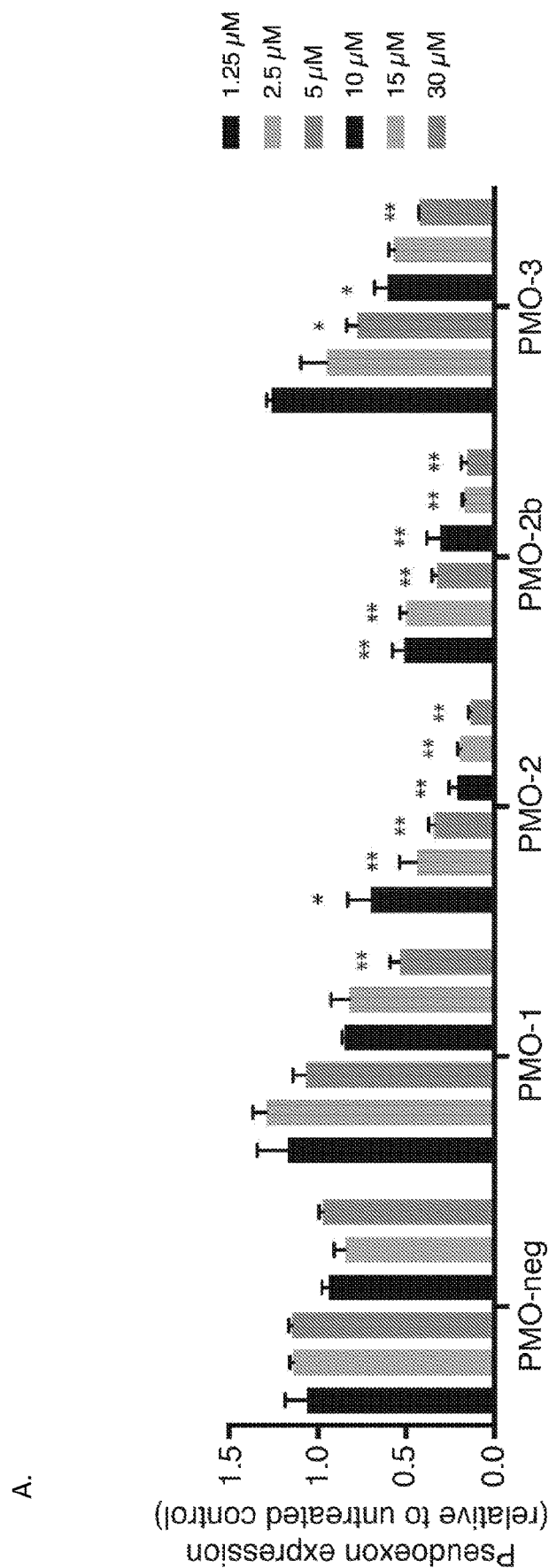
FIGS. 9A-9D.
Figure 9:
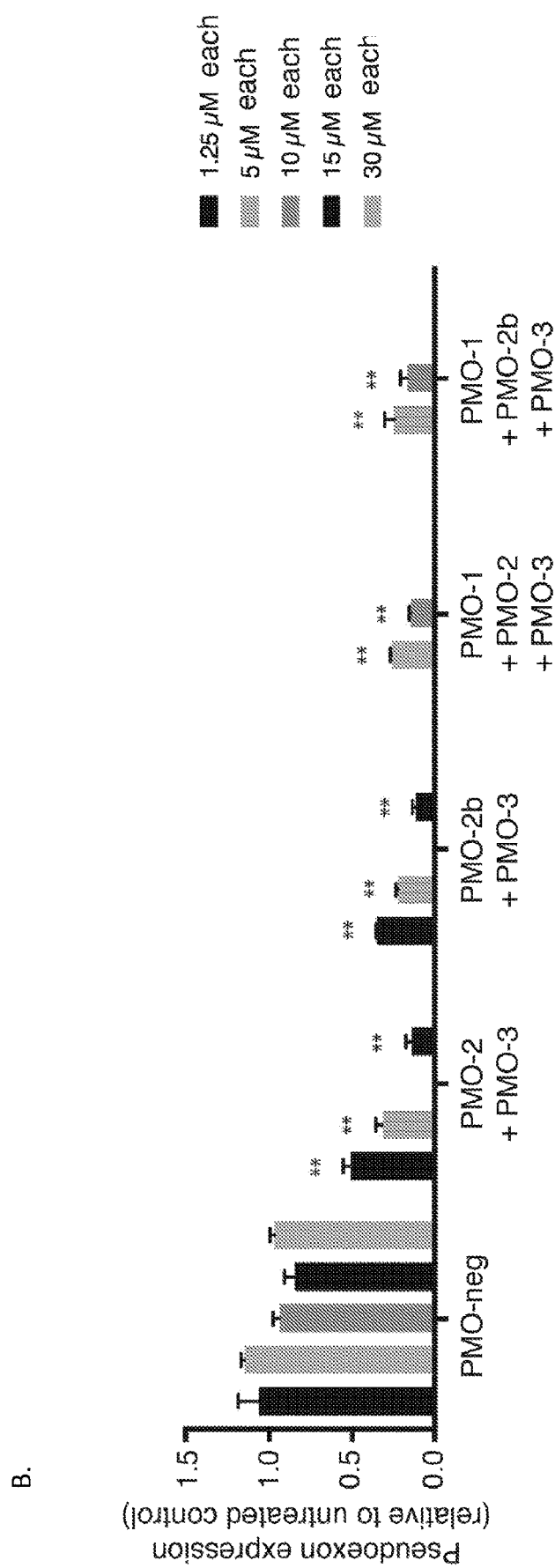
Figure 9:
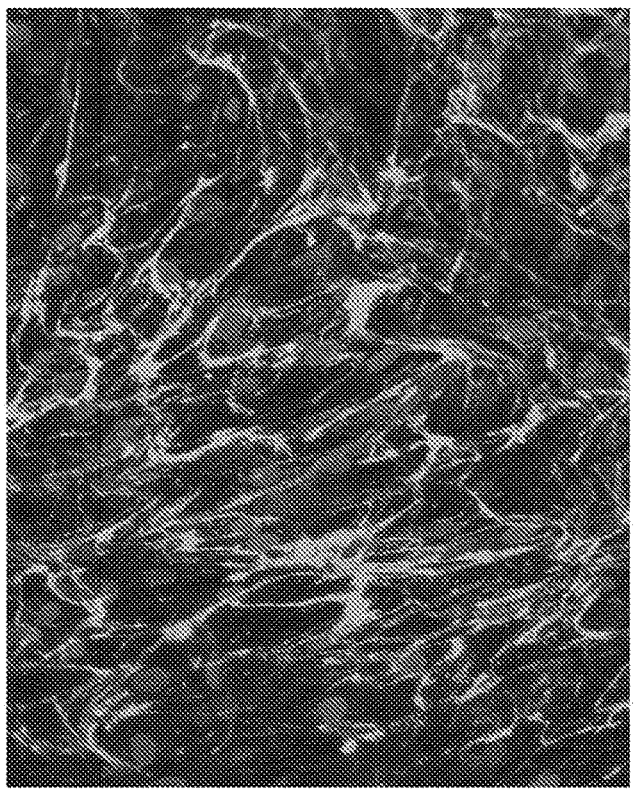
Figure 9:
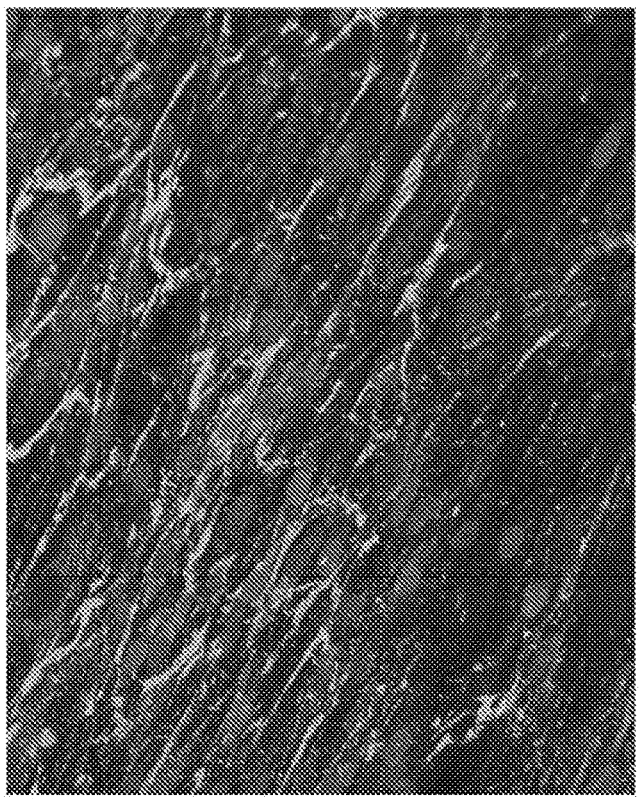
Figure 9:
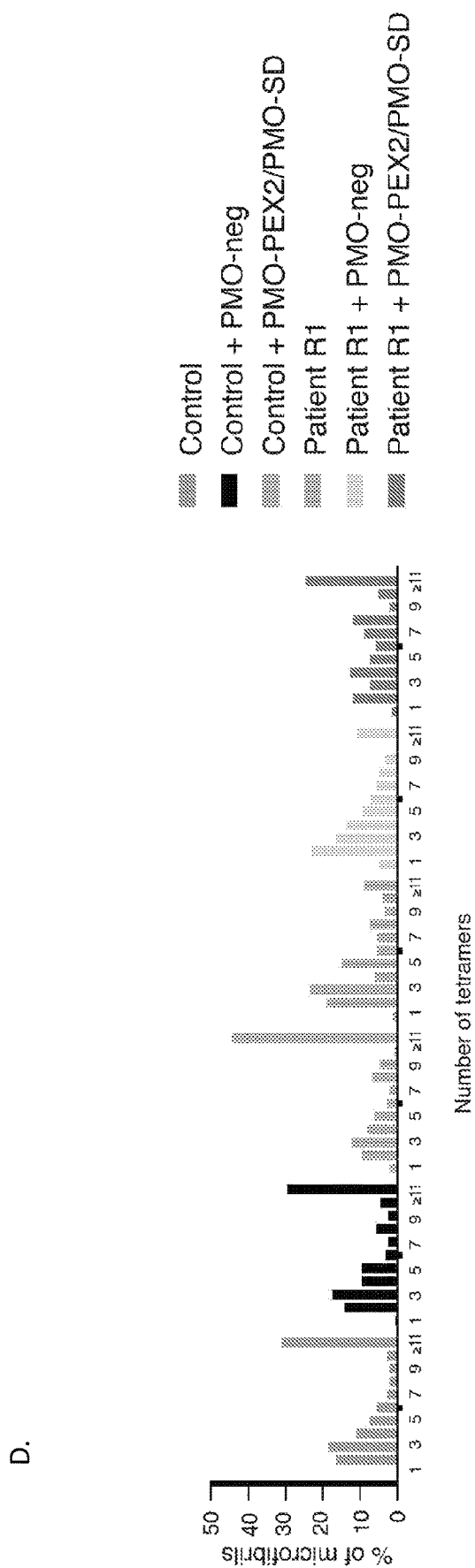

Example 7. Effect of Morpholino Antisense Oligonucleotides on Pseudoexon Expression and Microfibril Formation Patient-Derived Cells The effect of the described PMOs on patient-derived fibroblasts was determined by first comparing pseudoexon expression levels in patient-derived fibroblasts treated for 48 h either with single PMOs (FIG. 9A), or with a combination of PMOs (FIG. 9B) at various doses. Following treatment, the cells were harvested, cellular RNA isolated and amplified, and the amplified RNA analyzed using an allele-specific quantitative reverse transcriptase PCR (RT-PCR) assay normalized to phosphoglycerate kinase 1 (PGK1). The results of this analysis are shown in FIGS. 9A and 9B. The results show that the individual PMOs caused a decrease of pseudoexon expression (FIG. 9A). The results also show that pseudoexon expression was lower in cells treated with combinations of PMOs than in cells treated with an individual PMO (FIG. 9B).

Treated and untreated fibroblasts were also stained for matrix-deposited collagen, and examined by fluorescent microscopy. This analysis showed that deposition of collagen VI microfibrils on the matrix was greater in PMO-treated cells, compared with cells treated with a non-targeting PMO (PMO-neg) (FIG. 9C). Further, rotary shadowing electron microscopy showed that microfibril length in PMO-treated cells was greater, when compared with the length of microfibrils in PMO-neg-treated cells. Thus, PMO treatment increased the length of collagen VI microfibrils, as seen by the higher number of tetramers per microfibrils following treatment (FIG. 9D).

Example 8. Modeling of COL6A1 Intron 11+189C>T Mutation in Mouse/Human Chimeric Reporter A chimeric splicing reporter plasmid was prepared by cloning the mouse genomic sequence encompassing exon 11 to exon 13, and by replacing the intron 11 sequence with human intron 11, in presence of the wildtype (+189C) or the mutant (+189T) genotype. A schematic of this design in shown in FIG. 10A.

Figure 10:
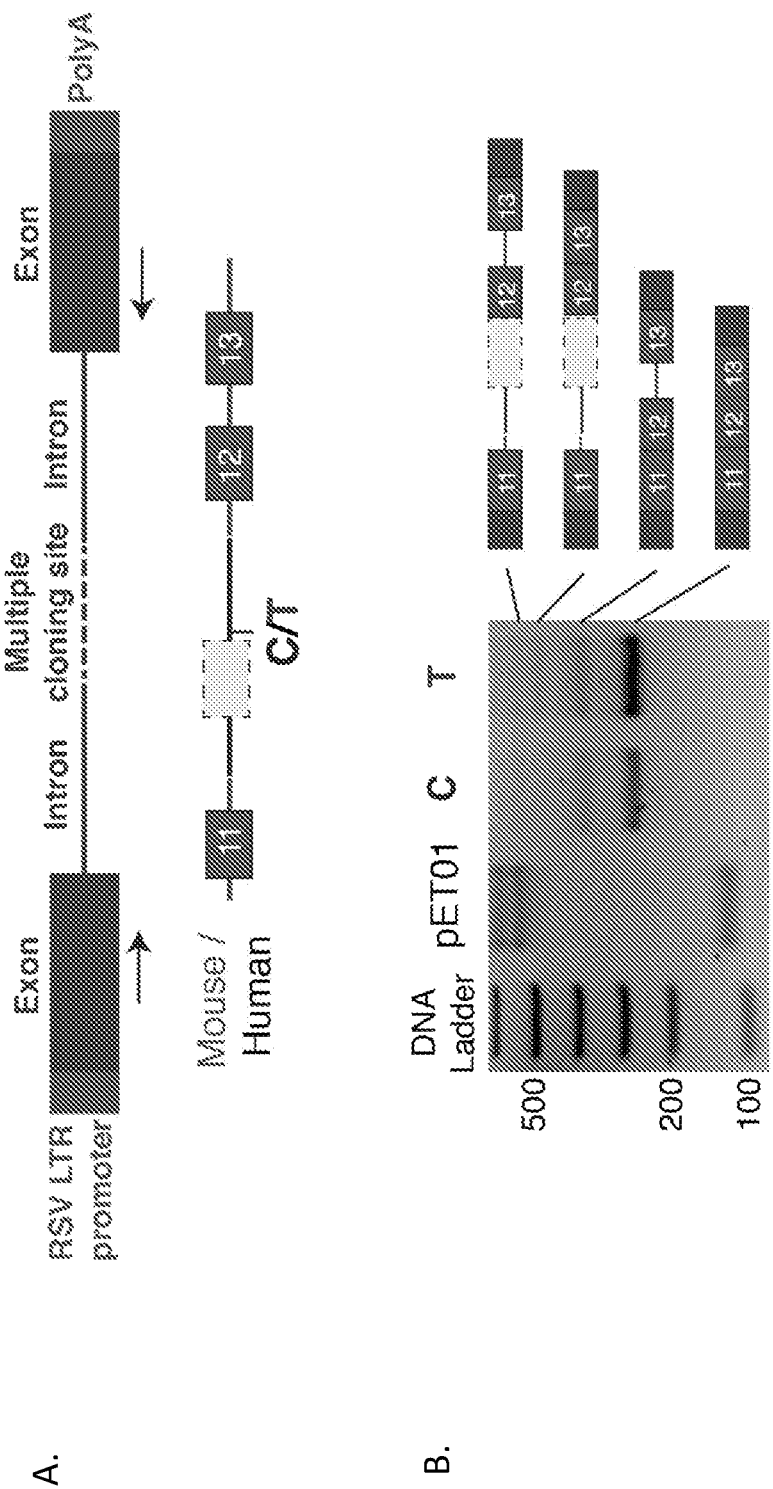
FIGS. 10A and B.
FIG. 10B shows the results of assays in which reporter constructs were transfected in murine primary skin fibroblasts, and expression from the splicing reporter analyzed by reverse transcriptase PCR (RT-PCR).
Figure 11:
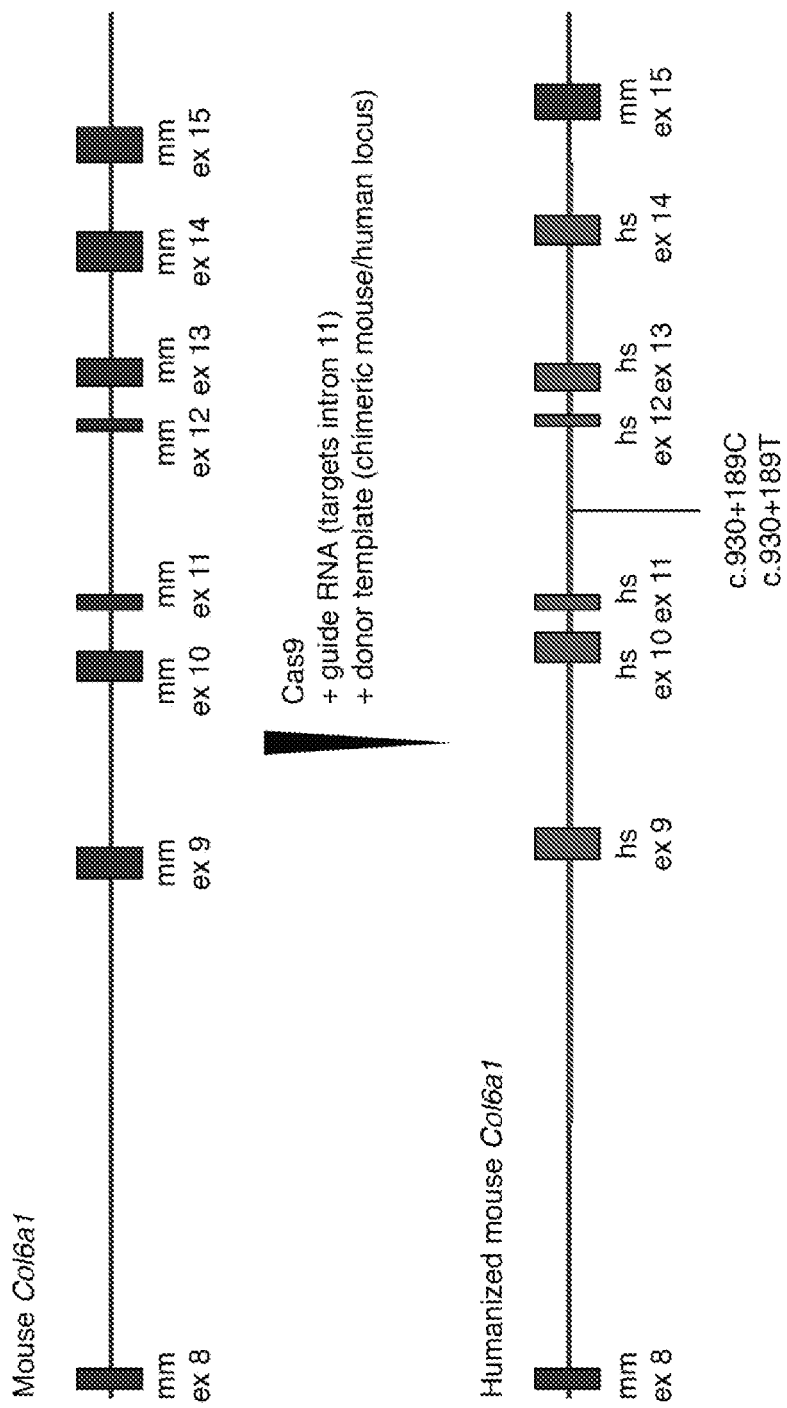
FIG. 11 is a schematic of the CRISPR/Cas9 strategy to replace mouse sequence spanning exon 9 to exon 14 with its human counterpart. The donor template will be synthesized in two versions: one carrying the normal allele (+189C), one carrying the mutant allele (+189T), to generate two humanized alleles.

To determine if the chimeric splicing sites were recognized in mouse cells, the reporter plasmids were transfected in murine primary skin fibroblasts, and expression from the splicing reporter was analyzed by reverse transcriptase PCR (RT-PCR) and sequencing. The results, which are shown in FIG. 10B demonstrate that the mutant splice donor was recognized within this mouse-human chimeric genomic context. Retention of intron 12 was also found as an unexpected splicing event.

Discussion

In these Examples, the inventors have described a new mutational mechanism for collagen VI-related disorders: an intronic mutation in COL6A1 causing the retention of an in-frame pseudo exon. The c.930+189C>T mutation is located in intron 11, and creates a new 5' donor splice site that when used inserts 72 bp of intronic sequence (24 aa) at the N-terminal part of the TH domain. Similar to exon deletions at this location, this exon insertion is likely to act as dominant-negative, as the mutant chain would take part in monomer formation, but would interrupt the repeated Gly-X-Y motif at the end of the collagenous domain. Additionally, the mutation does not affect the critical cysteine residue, so that the chain that carries it is likely to assemble into dimer and tetramer molecules, which may account for its strong dominant-negative effect.

Patient muscle biopsies showed accumulation of collagen VI in endomysium, with absence of localization at the basement membrane, which is consistent with dominant-negative mutations. However, dermal fibroblasts in culture did not show the expected reduction in collagen VI matrix deposition and increase of retention. This can be explained by the low levels of expression of the mutant allele in these cells, likely the result of alternative splicing which increases the ratio of normal versus mutant chain. This also makes the dermal fibroblasts a poor model to study this mutation in vitro.

This COL6A1 intronic mutation, despite being common in the patient population, was originally missed because of the low level of expression in dermal fibroblasts. This observation emphasizes once again the relevance of performing thorough clinical examinations, in addition to using alternative methods of mutation detection.

In the NIH cohort of patients, this mutation was the single most common individual mutation identified to date for COL6-RD. It was also identified in patients from different populations after screening several cohorts of undiagnosed collagen VI-like patients. This mutation manifests as a severe Ullrich muscular dystrophy but possibly with a slightly delayed onset compared to the classic Ullrich presentation. The reasons for a low abundance of mutant expression being associated with severe phenotype are still elusive. With different quantification methods (RNA-seq, gel quantification, qRT-PCR), the inventors demonstrated that the mutant allele is expressed at lower levels than the 1:1 expected ratio, in dermal fibroblasts but also in RNA samples freshly isolated from muscle. It is possible that the mutant chain has different biochemical properties such as longer half-life or increased stability that make them prone to accumulation, and lead to deleterious effects over time.

The minigene assays confirmed that the mutation creates a strong 5' splice site, although the choice of the 3' acceptor may be tissue-dependent.

Intronic mutations leading to aberrant splicing events have been described for other disorders including other muscular dystrophies, although most frequently as loss-of-function mutations causing out-of-frame intron retention. Mutations causing pseudo exon retention offer opportunity for treatment using splice-modulating oligomers. The inventors tested PMO antisense oligonucleotides, and the oligonucleotide directly targeting the mutant 5' splice site did not promote skipping, possibly because RNA secondary structure makes it a poor choice of target. The most efficient oligonucleotide was one targeting a potential exonic splicing enhancer site, suggesting that trans factors facilitate the insertion of the pseudoexon.

The foregoing description of the specific embodiments will so fully reveal the general nature of the invention that others can, by applying knowledge within the skill of the art, readily modify and/or adapt for various applications such specific embodiments, without undue experimentation, without departing from the general concept of this disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

What is claimed is:

1. A synthetic antisense oligomer that
   a) comprises a sequence selected from the group consisting of SEQ ID NO: 15, SEQ ID NO: 16, SEQ ID NO: 17, SEQ ID NO: 18, SEQ ID NO: 19, SEQ ID NO:20, SEQ ID NO:21, SEQ ID NO:22, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, and SEQ ID NO:44;
   wherein the antisense oligomer consists of a number of monomers no more than 5 monomers greater than its respective SEQ ID NO; or
   b) consists of a sequence of monomers identical to a sequence comprised by one of SEQ ID NO: 15, SEQ ID NO: 16, SEQ ID NO: 17, SEQ ID NO: 18, SEQ ID NO: 19, SEQ ID NO:20, SEQ ID NO:21, SEQ ID NO:22, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, and SEQ ID NO:44, where said sequence of monomers is not less than 5 monomers shorter than its respective SEQ ID NO,
   wherein the antisense oligomer is an antisense RNA molecule having a chemical modification that increases its affinity for its target RNA, increases its nuclease resistance, and/or alters its pharmacokinetics,
   wherein the chemical modification is selected from the group consisting of;
   substitution of a sugar for a sugar mimetic or sugar analog, substitution of a sugar-internucleoside linkage combination for an analog or mimetic; substitution of a nucleobase for an analog or mimetic; and, any combination thereof,
   and wherein the presence of the antisense oligomer in a splicing reaction comprising a COL6A1 pre-mRNA molecule having a non-native splice donor site in intron 11, results in normal splicing of the COL6A1 pre-mRNA molecule.

2. A method of modulating splicing of a COL6A1 pre-mRNA molecule having a non-native splice donor or splice acceptor site, the method comprising contacting a cell expressing the COL6A1 pre-mRNA molecule having the non-native splice donor or splice acceptor site, with the antisense oligomer of claim 1.

3. The A method of claim 2, wherein the cell is from an individual having a collagen VI-related disorder (COLVI-RD).

4. An expression vector encoding the antisense oligomer of claim 1, wherein said expression vector is from a plasmid, bacteriophage, yeast or virus.

5. The antisense oligomer of claim 1, wherein the oligomer has been modified to reduce degradation of the oligomer in comparison with an unmodified oligomer that is targeted to the same sequence.

6. The antisense oligomer of claim 5, wherein modification of the oligomer comprises a modification selected from the group consisting of a nucleoside modification, an internucleoside modification, a sugar modification, a sugar-internucleoside linkage modification, a peptide addition, and combinations thereof.

7. The antisense oligomer of claim 5, wherein the oligomer is a morpholino oligomer.

8. A kit comprising the synthetic antisense oligomer of claim 1.

* * * * *

SEQUENCE LISTING

<160> NUMBER OF SEQ ID NOS: 64

<210> SEQ ID NO 1
<211> LENGTH: 27
<212> TYPE: DNA
<213> ORGANISM: Homo sapiens

<400> SEQUENCE: 1
ggagaaaaag ggagccgtgg ggagaag                                        27

```
<210> SEQ ID NO 2
<211> LENGTH: 9
<212> TYPE: PRT
<213> ORGANISM: Homo sapiens

<400> SEQUENCE: 2

Gly Glu Lys Gly Ser Arg Gly Glu Lys
1               5

<210> SEQ ID NO 3
<211> LENGTH: 479
<212> TYPE: DNA
<213> ORGANISM: Homo sapiens

<400> SEQUENCE: 3
gtgagtgagg ctcgacctcg gagctggtct ctccaggcgc agatgtgcca tcctggacga      60
gggtgtcccc ggggatgagg acagtgtccc tgacaggaga ccacgtgtcc tgcagacccg     120
ctccaccgcc cctcgccgtc ccctccatct ggaaggacag ggacagccac ccaggcaccc     180
agcaaaggcg cctgtgtcac tttcacccca ccccagagca ggggtccccc gggcggttac     240
cctctgcgga gccggggggtc ccccgggcgg ttaccctctg cggagccggg ggtccccgg     300 gcggttaccc tctgcagagc ggcccctccc catcactgtc agtccccatg attctcagca     360
gtgatgttgt ccctcgggt tgggggcacc caagcccctg cctcgcgtgg gcctaagcca     420
ggcttgccct gccctcccca ccccaaatac cccctcacac ccgcttcctg tctccgcag     479

<210> SEQ ID NO 4
<211> LENGTH: 72
<212> TYPE: DNA
<213> ORGANISM: Homo sapiens

<400> SEQUENCE: 4
acccgctcca ccgcccctcg ccgtcccctc catctggaag gacaaggaca gccacccagg      60
cacccagcaa ag                                                         72

<210> SEQ ID NO 5
<211> LENGTH: 24
<212> TYPE: PRT
<213> ORGANISM: Homo sapiens

<400> SEQUENCE: 5

Thr Arg Ser Thr Ala Pro Arg Arg Pro Leu His Leu Glu Gly Gln Gly
1               5                   10                  15

Gln Pro Pro Arg His Pro Ala Lys
            20

<210> SEQ ID NO 6
<211> LENGTH: 42
<212> TYPE: DNA
<213> ORGANISM: Homo sapiens

<400> SEQUENCE: 6
acccaggcac ccagcaaagg cgcctgtgtc actttcaccc ct                         42

<210> SEQ ID NO 7
<211> LENGTH: 27
<212> TYPE: DNA
<213> ORGANISM: Homo sapiens

<400> SEQUENCE: 7
```

```
ggctccaggg gacccaaggg ctacaag                                           27
```

<210> SEQ ID NO 8
<211> LENGTH: 9
<212> TYPE: PRT
<213> ORGANISM: Homo sapiens

<400> SEQUENCE: 8

Gly Ser Arg Gly Pro Lys Gly Tyr Lys
1               5

<210> SEQ ID NO 9
<211> LENGTH: 24
<212> TYPE: DNA
<213> ORGANISM: Homo sapiens

<400> SEQUENCE: 9

```
cgtggggaga agacccgctc cacc                                              24
```

<210> SEQ ID NO 10
<211> LENGTH: 8
<212> TYPE: PRT
<213> ORGANISM: Homo sapiens

<400> SEQUENCE: 10

Arg Gly Glu Lys Thr Arg Ser Thr
1               5

<210> SEQ ID NO 11
<211> LENGTH: 24
<212> TYPE: DNA
<213> ORGANISM: Homo sapiens

<400> SEQUENCE: 11

```
cacccagcaa agggctccag ggga                                              24
```

<210> SEQ ID NO 12
<211> LENGTH: 8
<212> TYPE: PRT
<213> ORGANISM: Homo sapiens

<400> SEQUENCE: 12

His Pro Ala Lys Gly Ser Arg Gly
1               5

<210> SEQ ID NO 13
<211> LENGTH: 24
<212> TYPE: DNA
<213> ORGANISM: Homo sapiens

<400> SEQUENCE: 13

```
cgtggggaga agggctccag ggga                                              24
```

<210> SEQ ID NO 14
<211> LENGTH: 8
<212> TYPE: PRT
<213> ORGANISM: Homo sapiens

<400> SEQUENCE: 14

Arg Gly Glu Lys Gly Ser Arg Gly
1               5

<210> SEQ ID NO 15

<211> LENGTH: 25
<212> TYPE: RNA
<213> ORGANISM: Artificial sequence
<220> FEATURE:
<223> OTHER INFORMATION: Synthetic

<400> SEQUENCE: 15
guggagcggg ucugcaggac acgug                                              25

<210> SEQ ID NO 16
<211> LENGTH: 25
<212> TYPE: RNA
<213> ORGANISM: Artificial sequence
<220> FEATURE:
<223> OTHER INFORMATION: Synthetic

<400> SEQUENCE: 16
ggcuguccuu guccucccag augga                                              25

<210> SEQ ID NO 17
<211> LENGTH: 25
<212> TYPE: RNA
<213> ORGANISM: Artificial sequence
<220> FEATURE:
<223> OTHER INFORMATION: Synthetic

<400> SEQUENCE: 17
aggcaccuuu gcugggugcc ugggu                                              25

<210> SEQ ID NO 18
<211> LENGTH: 25
<212> TYPE: RNA
<213> ORGANISM: Artificial sequence
<220> FEATURE:
<223> OTHER INFORMATION: Synthetic

<400> SEQUENCE: 18
ugaaagugac acaggcaccu uugcu                                              25

<210> SEQ ID NO 19
<211> LENGTH: 23
<212> TYPE: RNA
<213> ORGANISM: Artificial sequence
<220> FEATURE:
<223> OTHER INFORMATION: Synthetic

<400> SEQUENCE: 19
ggugaaagug acacaggcaa ccu                                                23

<210> SEQ ID NO 20
<211> LENGTH: 20
<212> TYPE: RNA
<213> ORGANISM: Artificial sequence
<220> FEATURE:
<223> OTHER INFORMATION: Synthetic

<400> SEQUENCE: 20
agauggaggg gacggcgagg                                                    20

<210> SEQ ID NO 21
<211> LENGTH: 20
<212> TYPE: RNA
<213> ORGANISM: Artificial sequence
<220> FEATURE:
<223> OTHER INFORMATION: Synthetic

<400> SEQUENCE: 21

```
ggcuguccuu guccuuccag                                              20

<210> SEQ ID NO 22
<211> LENGTH: 20
<212> TYPE: RNA
<213> ORGANISM: Artificial sequence
<220> FEATURE:
<223> OTHER INFORMATION: Synthetic

<400> SEQUENCE: 22
gugccugggu ggcuguccuu                                              20

<210> SEQ ID NO 23
<211> LENGTH: 25
<212> TYPE: RNA
<213> ORGANISM: Homo sapiens

<400> SEQUENCE: 23
cacguguccu gcagacccgc uccac                                        25

<210> SEQ ID NO 24
<211> LENGTH: 25
<212> TYPE: RNA
<213> ORGANISM: Homo sapiens

<400> SEQUENCE: 24
uccaucugga aggacaagga cagcc                                        25

<210> SEQ ID NO 25
<211> LENGTH: 25
<212> TYPE: RNA
<213> ORGANISM: Homo sapiens

<400> SEQUENCE: 25
acccaggcac ccagcaaagg ugccu                                        25

<210> SEQ ID NO 26
<211> LENGTH: 25
<212> TYPE: RNA
<213> ORGANISM: Homo sapiens

<400> SEQUENCE: 26
agcaaaggug ccugugucac uuuca                                        25

<210> SEQ ID NO 27
<211> LENGTH: 22
<212> TYPE: RNA
<213> ORGANISM: Homo sapiens

<400> SEQUENCE: 27
aggugccugu gucacuuuca cc                                           22

<210> SEQ ID NO 28
<211> LENGTH: 20
<212> TYPE: RNA
<213> ORGANISM: Homo sapiens

<400> SEQUENCE: 28
ccucgccguc cccuccaucu                                              20

<210> SEQ ID NO 29
<211> LENGTH: 20
<212> TYPE: RNA
```

<213> ORGANISM: Homo sapiens

<400> SEQUENCE: 29
cuggaaggac aaggacagcc                                                      20

<210> SEQ ID NO 30
<211> LENGTH: 20
<212> TYPE: RNA
<213> ORGANISM: Homo sapiens

<400> SEQUENCE: 30
aaggacagcc acccaggcac                                                      20

<210> SEQ ID NO 31
<211> LENGTH: 25
<212> TYPE: DNA
<213> ORGANISM: Artificial sequence
<220> FEATURE:
<223> OTHER INFORMATION: Synthetic

<400> SEQUENCE: 31
aggacacctg gtctcctgtc aggga                                                25

<210> SEQ ID NO 32
<211> LENGTH: 25
<212> TYPE: DNA
<213> ORGANISM: Artificial sequence
<220> FEATURE:
<223> OTHER INFORMATION: Synthetic

<400> SEQUENCE: 32
gctgtccttg tccttccaga tggag                                                25

<210> SEQ ID NO 33
<211> LENGTH: 25
<212> TYPE: DNA
<213> ORGANISM: Artificial sequence
<220> FEATURE:
<223> OTHER INFORMATION: Synthetic

<400> SEQUENCE: 33
tgaaagtgac acaggcacct ttgct                                                25

<210> SEQ ID NO 34
<211> LENGTH: 25
<212> TYPE: DNA
<213> ORGANISM: Artificial sequence
<220> FEATURE:
<223> OTHER INFORMATION: Synthetic

<400> SEQUENCE: 34
gtggctgtcc ttgtccttcc agatg                                                25

<210> SEQ ID NO 35
<211> LENGTH: 23
<212> TYPE: DNA
<213> ORGANISM: Artificial sequence
<220> FEATURE:
<223> OTHER INFORMATION: Synthetic

<400> SEQUENCE: 35
ttgtccttcc agatggacgg gac                                                  23

<210> SEQ ID NO 36
<211> LENGTH: 25

-continued

<212> TYPE: DNA
<213> ORGANISM: Artificial sequence
<220> FEATURE:
<223> OTHER INFORMATION: Synthetic

<400> SEQUENCE: 36
gtgcctgggt cgctgtcctt gtcct                                    25

<210> SEQ ID NO 37
<211> LENGTH: 25
<212> TYPE: DNA
<213> ORGANISM: Artificial sequence
<220> FEATURE:
<223> OTHER INFORMATION: Synthetic

<400> SEQUENCE: 37
tctgcaggac acgtggtctc ctgtc                                    25

<210> SEQ ID NO 38
<211> LENGTH: 25
<212> TYPE: DNA
<213> ORGANISM: Artificial sequence
<220> FEATURE:
<223> OTHER INFORMATION: Synthetic

<400> SEQUENCE: 38
ggtctgcagg acacgtggtc tcctg                                    25

<210> SEQ ID NO 39
<211> LENGTH: 25
<212> TYPE: DNA
<213> ORGANISM: Artificial sequence
<220> FEATURE:
<223> OTHER INFORMATION: Synthetic

<400> SEQUENCE: 39
ctgtccttgt ccttccagat ggagg                                    25

<210> SEQ ID NO 40
<211> LENGTH: 25
<212> TYPE: DNA
<213> ORGANISM: Artificial sequence
<220> FEATURE:
<223> OTHER INFORMATION: Synthetic

<400> SEQUENCE: 40
ggctgtcctt gtccttccag atgga                                    25

<210> SEQ ID NO 41
<211> LENGTH: 25
<212> TYPE: DNA
<213> ORGANISM: Artificial sequence
<220> FEATURE:
<223> OTHER INFORMATION: Synthetic

<400> SEQUENCE: 41
tggctgtcct tgtccttcca gatgg                                    25

<210> SEQ ID NO 42
<211> LENGTH: 25
<212> TYPE: DNA
<213> ORGANISM: Artificial sequence
<220> FEATURE:
<223> OTHER INFORMATION: Synthetic

<400> SEQUENCE: 42
ggtggctgtc cttgtccttc cagat                                              25

<210> SEQ ID NO 43
<211> LENGTH: 25
<212> TYPE: DNA
<213> ORGANISM: Artificial sequence
<220> FEATURE:
<223> OTHER INFORMATION: Synthetic

<400> SEQUENCE: 43
tggggtgaaa gtgacacagg cacct                                              25

<210> SEQ ID NO 44
<211> LENGTH: 25
<212> TYPE: DNA
<213> ORGANISM: Artificial sequence
<220> FEATURE:
<223> OTHER INFORMATION: Synthetic

<400> SEQUENCE: 44
ggtgaaagtg acacaggcac ctttg                                              25

<210> SEQ ID NO 45
<211> LENGTH: 25
<212> TYPE: RNA
<213> ORGANISM: Homo sapiens

<400> SEQUENCE: 45
ucccugacag gagaccacgu guccu                                              25

<210> SEQ ID NO 46
<211> LENGTH: 25
<212> TYPE: RNA
<213> ORGANISM: Homo sapiens

<400> SEQUENCE: 46
cuccaucugg aaggacaagg acagc                                              25

<210> SEQ ID NO 47
<211> LENGTH: 25
<212> TYPE: RNA
<213> ORGANISM: Homo sapiens

<400> SEQUENCE: 47
agcaaaggug ccugugcac uuuca                                               25

<210> SEQ ID NO 48
<211> LENGTH: 25
<212> TYPE: RNA
<213> ORGANISM: Homo sapiens

<400> SEQUENCE: 48
caucuggaag gacaaggaca gccac                                              25

<210> SEQ ID NO 49
<211> LENGTH: 23
<212> TYPE: RNA
<213> ORGANISM: Homo sapiens

<400> SEQUENCE: 49
guccccucca ucuggaagga caa                                                23

<210> SEQ ID NO 50
<211> LENGTH: 25

<212> TYPE: RNA
<213> ORGANISM: Homo sapiens

<400> SEQUENCE: 50
aggacaagga cagccaccca ggcac                                              25

<210> SEQ ID NO 51
<211> LENGTH: 25
<212> TYPE: RNA
<213> ORGANISM: Homo sapiens

<400> SEQUENCE: 51
gacaggagac cacguguccu gcaga                                              25

<210> SEQ ID NO 52
<211> LENGTH: 25
<212> TYPE: RNA
<213> ORGANISM: Homo sapiens

<400> SEQUENCE: 52
caggagacca cguguccugc agacc                                              25

<210> SEQ ID NO 53
<211> LENGTH: 25
<212> TYPE: RNA
<213> ORGANISM: Homo sapiens

<400> SEQUENCE: 53
ccuccaucug gaaggacaag gacag                                              25

<210> SEQ ID NO 54
<211> LENGTH: 25
<212> TYPE: RNA
<213> ORGANISM: Homo sapiens

<400> SEQUENCE: 54
uccaucugga aggacaagga cagcc                                              25

<210> SEQ ID NO 55
<211> LENGTH: 25
<212> TYPE: RNA
<213> ORGANISM: Homo sapiens

<400> SEQUENCE: 55
ccaucuggaa ggacaaggac agcca                                              25

<210> SEQ ID NO 56
<211> LENGTH: 25
<212> TYPE: RNA
<213> ORGANISM: Homo sapiens

<400> SEQUENCE: 56
aucuggaagg acaaggacag ccacc                                              25

<210> SEQ ID NO 57
<211> LENGTH: 25
<212> TYPE: RNA
<213> ORGANISM: Homo sapiens

<400> SEQUENCE: 57
aggugccugu gucacuuuca cccca                                              25

<210> SEQ ID NO 58

```
<211> LENGTH: 25
<212> TYPE: RNA
<213> ORGANISM: Homo sapiens

<400> SEQUENCE: 58
caaaggugcc ugugucacuu ucacc                                              25

<210> SEQ ID NO 59
<211> LENGTH: 30
<212> TYPE: DNA
<213> ORGANISM: Homo sapiens

<400> SEQUENCE: 59
agccgtgggg agaaggtgag tgaggctcga                                         30

<210> SEQ ID NO 60
<211> LENGTH: 30
<212> TYPE: DNA
<213> ORGANISM: Homo sapiens

<400> SEQUENCE: 60
ttcctgtctc cgcagggctc caggggaccc                                         30

<210> SEQ ID NO 61
<211> LENGTH: 4246
<212> TYPE: DNA
<213> ORGANISM: Homo sapiens

<400> SEQUENCE: 61
gctctcactc tggctgggag cagaaggcag cctcggtctc tgggcggcgg cggcggccca        60
ctctgccctg gccgcgctgt gtggtgaccg caggccccag acatgagggc ggcccgtgct       120
ctgctgcccc tgctgctgca ggcctgctgg acagccgcgc aggatgagcc ggagaccccg       180
agggccgtgg ccttccagga ctgccccgtg gacctgttct ttgtgctgga cacctctgag       240
agcgtggccc tgaggctgaa gccctacggg ccctcgtgg acaaagtcaa gtccttcacc       300
aagcgcttca tcgacaacct gagggacagg tactaccgct gtgaccgaaa cctggtgtgg       360
aacgcaggcg cgctgcacta cagtgacgag gtggagatca tccaaggcct cacgcgcatg       420
cctggcggcc gcgacgcact caaaagcagc gtggacgcgg tcaagtactt tgggaagggc       480
acctacaccg actgcgctat caagaagggg ctggagcagc tcctcgtggg gggctcccac       540
ctgaaggaga ataagtacct gattgtggtg accgacgggc acccctggag gggctacaag       600
gaaccctgtg gggggctgga ggatgctgtg aacgaggcca agcacctggg cgtcaaagtc       660
ttctcggtgg ccatcacacc cgaccacctg agccgcgtc tgagcatcat cgccacggac       720
cacacgtacc ggcgcaactt cacggcggct gactgggggc agagccgcga cgcagaggag       780
gccatcagcc agaccatcga caccatcgtg gacatgatca aaaataacgt ggagcaagtg       840
tgctgctcct tcaatgcca gcctgcaaga ggacctccgg ggctccgggg cgaccccggc       900
tttgagggag aacgaggcaa gccggggctc ccaggagaga agggagaagc ggagatcct       960 ggaagacccg ggacctcgg acctgttggg taccagggaa tgaagggaga aaagggagc       1020 cgtgggaga agggctccag gggacccaag ggctacaagg agagaagggg caagcgtggc       1080
atcgacgggg tggacggcgt gaaggggag atggggtacc caggcctgcc aggctgcaag       1140
ggctcgcccg ggtttgacgg cattcaagga ccccctggcc caagggaga ccccggtgcc       1200 tttggactga aaggagaaaa gggcgagcct gagctgacg ggaggcggg gagaccaggg       1260 agctcgggac catctggaga cgagggccag ccggagagc ctgggccccc cggagagaaa       1320
```

```
ggagaggcgg gcgacgaggg gaacccagga cctgacggtg ccccgggga gcggggtggc    1380
cctggagaga gaggaccacg ggggacccca ggcacgcggg gaccaagagg agaccctggt    1440
gaagctggcc cgcagggtga tcagggaaga gaaggccccg ttggtgtccc tggagacccg    1500
ggcgaggctg gccctatcgg acctaaaggc taccgaggcg atgagggtcc cccagggtcc    1560
gagggtgcca gaggagcccc aggacctgcc ggaccccctg agacccggg gctgatgggt     1620
gaaagggag aagacggccc cgctggaaat ggcaccgagg gcttccccgg cttccccggg     1680
tatccgggca cagggcgc tcccgggata acggcacga agggctaccc cggcctcaag       1740
ggggacgagg gagaagccgg ggaccccgga cgataaca acgacattgc accccgagga      1800
gtcaaaggag caaaggggta ccggggtccc gagggccccc agggaccccc aggacaccaa   1860
ggaccgcctg ggccggacga atgcgagatt ttggacatca tcatgaaaat gtgctcttgc   1920
tgtgaatgca agtgcggccc catcgacctc ctgttcgtgc tggacagctc agagagcatt   1980
ggcctgcaga acttcgagat tgccaaggac ttcgtcgtca aggtcatcga ccggctgagc   2040
cgggacgagc tggtcaagtt cgagccaggg cagtcgtacg cgggtgtggt gcagtacagc   2100
cacagccaga tgcaggagca cgtgagcctg cgcagcccca gcatccggaa cgtgcaggag   2160
ctcaaggaag ccatcaagag cctgcagtgg atggcgggcg gcaccttcac ggggaggcc    2220
ctgcagtaca cgcgggacca gctgctgccg cccagcccga caaccgcat cgccctggtc    2280
atcactgacg ggcgctcaga cactcagagg gacaccacac cgctcaacgt gctctgcagc   2340
cccggcatcc aggtggtctc cgtgggcatc aaagacgtgt ttgacttcat cccaggctca   2400
gaccagctca atgtcatttc ttgccaaggc ctggcaccat cccagggccg gcccggcctc   2460
tcgctggtca aggagaacta tgcagagctg ctggaggatg ccttcctgaa gaatgtcacc   2520
gcccagatct gcatagacaa gaagtgtcca gattacacct gccccatcac gttctcctcc   2580
ccggctgaca tcaccatcct gctggacggc tccgccagcg tgggcagcca caactttgac   2640
accaccaagc gcttcgccaa cgcctggcc gagcgcttcc tcacagcggg caggacggac   2700
cccgccacg acgtgcgggt ggcggtggtg cagtacagcg gcacgggcca gcagcgccca   2760
gagcgggcgt cgctgcagtt cctgcagaac tacacggccc tggccagtgc cgtcgatgcc   2820
atggacttta tcaacgacgc caccgacgtc aacgatgccc tgggctatgt gacccgcttc   2880
taccgcgagg cctcgtccgg cgctgccaag aagaggctgc tgctcttctc agatggcaac   2940
tcgcagggcg ccacgcccgc tgccatcgag aaggccgtgc aggaagccca gcgggcaggc   3000
atcgagatct tcgtggtggt cgtgggccgc caggtgaatg agccccacat ccgcgtcctg   3060
gtcaccggca agacggccga gtacgacgtg gcctacggcg agagccacct gttccgtgtc   3120
cccagctacc aggccctgct ccgcggtgtc ttcaccagag cagtctccag gaaggtggcg   3180
ctgggctagc ccaccctgca cgccggcacc aaaccctgtc ctcccacccc tccccactca   3240
tcactaaaca gagtaaaatg tgatgcgaat tttcccgacc aacctgattc gctagatttt   3300
tttaaggaa aagcttggaa agccaggaca caacgctgct gcctgctttg tgcagggtcc   3360
tccgggctc agccctgagt tggcatcacc tgcgcagggc cctctggggc tcagccctga   3420
gctagtgtca cctgcacagg gccctctgag gctcagccct gagctggcgt cacctgtgca   3480
gggccctctg gggctcagcc ctgagctggc ctcacctggg ttccccaccc cgggctctcc   3540
tgccctgccc tcctgcccgc cctccctcct gcctgcgcag ctccttccct aggcacctct   3600
gtgctgcatc ccaccagcct gagcaagacg ccctctcggg gcctgtgccg cactagcctc   3660
```

```
cctctcctct gtccccatag ctggttttc ccaccaatcc tcacctaaca gttactttac    3720
aattaaactc aaagcaagct cttctcctca gcttggggca gccattggcc tctgtctcgt    3780
tttgggaaac caaggtcagg aggccgttgc agacataaat ctcggcgact cggcccgtc     3840 tcctgagggt cctgctggtg accggcctgg accttggccc tacagccctg gaggccgctg    3900
ctgaccagca ctgaccccga cctcagagag tactcgcagg ggcgctggct gcactcaaga    3960
ccctcgagat taacggtgct aaccccgtct gctcctccct cccgcagaga ctggggcctg    4020
gactggacat gagagcccct tggtgccaca gagggctgtg tcttactaga aacaacgcaa    4080
acctctcctt cctcagaata gtgatgtgtt cgacgtttta tcaaaggccc cctttctatg    4140
ttcatgttag ttttgctcct tctgtgtttt tttctgaacc atatccatgt tgctgacttt    4200
tccaaataaa ggttttcact cctctaaaaa aaaaaaaaaa aaaaaa                   4246
```

```
<210> SEQ ID NO 62
<211> LENGTH: 1028
<212> TYPE: PRT
<213> ORGANISM: Homo sapiens

<400> SEQUENCE: 62

Met Arg Ala Ala Arg Ala Leu Leu Pro Leu Leu Leu Gln Ala Cys Trp
1               5                   10                  15

Thr Ala Ala Gln Asp Glu Pro Glu Thr Pro Arg Ala Val Ala Phe Gln
                20                  25                  30

Asp Cys Pro Val Asp Leu Phe Phe Val Leu Asp Thr Ser Glu Ser Val
            35                  40                  45

Ala Leu Arg Leu Lys Pro Tyr Gly Ala Leu Val Asp Lys Val Lys Ser
        50                  55                  60

Phe Thr Lys Arg Phe Ile Asp Asn Leu Arg Asp Arg Tyr Tyr Arg Cys
65                  70                  75                  80

Asp Arg Asn Leu Val Trp Asn Ala Gly Ala Leu His Tyr Ser Asp Glu
                85                  90                  95

Val Glu Ile Ile Gln Gly Leu Thr Arg Met Pro Gly Gly Arg Asp Ala
            100                 105                 110

Leu Lys Ser Ser Val Asp Ala Val Lys Tyr Phe Gly Lys Gly Thr Tyr
        115                 120                 125

Thr Asp Cys Ala Ile Lys Lys Gly Leu Glu Gln Leu Leu Val Gly Gly
    130                 135                 140

Ser His Leu Lys Glu Asn Lys Tyr Leu Ile Val Val Thr Asp Gly His
145                 150                 155                 160

Pro Leu Glu Gly Tyr Lys Glu Pro Cys Gly Gly Leu Glu Asp Ala Val
                165                 170                 175

Asn Glu Ala Lys His Leu Gly Val Lys Val Phe Ser Val Ala Ile Thr
            180                 185                 190

Pro Asp His Leu Glu Pro Arg Leu Ser Ile Ile Ala Thr Asp His Thr
        195                 200                 205

Tyr Arg Arg Asn Phe Thr Ala Ala Asp Trp Gly Gln Ser Arg Asp Ala
    210                 215                 220

Glu Glu Ala Ile Ser Gln Thr Ile Asp Thr Ile Val Asp Met Ile Lys
225                 230                 235                 240

Asn Asn Val Glu Gln Val Cys Cys Ser Phe Glu Cys Gln Pro Ala Arg
                245                 250                 255

Gly Pro Pro Gly Leu Arg Gly Asp Pro Gly Phe Glu Gly Glu Arg Gly
            260                 265                 270
```

```
Lys Pro Gly Leu Pro Gly Glu Gly Glu Ala Gly Asp Pro Gly Arg
            275                 280                 285

Pro Gly Asp Leu Gly Pro Val Gly Tyr Gln Met Lys Gly Glu Lys
        290                 295                 300

Gly Ser Arg Gly Glu Lys Gly Ser Arg Gly Pro Lys Gly Tyr Lys Gly
305                 310                 315                 320

Glu Lys Gly Lys Arg Gly Ile Asp Gly Val Asp Gly Val Lys Gly Glu
                325                 330                 335

Met Gly Tyr Pro Gly Leu Pro Gly Cys Lys Gly Ser Pro Gly Phe Asp
            340                 345                 350

Gly Ile Gln Gly Pro Pro Gly Lys Gly Asp Pro Gly Ala Phe Gly
        355                 360                 365

Leu Lys Gly Glu Lys Gly Glu Pro Gly Ala Asp Gly Glu Ala Gly Arg
370                 375                 380

Pro Gly Ser Ser Gly Pro Ser Gly Asp Glu Gly Gln Pro Gly Glu Pro
385                 390                 395                 400

Gly Pro Pro Gly Glu Lys Gly Glu Ala Gly Asp Glu Gly Asn Pro Gly
        405                 410                 415

Pro Asp Gly Ala Pro Gly Glu Arg Gly Gly Pro Gly Glu Arg Gly Pro
        420                 425                 430

Arg Gly Thr Pro Gly Thr Arg Gly Pro Arg Gly Asp Pro Gly Glu Ala
        435                 440                 445

Gly Pro Gln Gly Asp Gln Gly Arg Glu Gly Pro Val Gly Val Pro Gly
        450                 455                 460

Asp Pro Gly Glu Ala Gly Pro Ile Gly Pro Lys Gly Tyr Arg Gly Asp
465                 470                 475                 480

Glu Gly Pro Pro Gly Ser Glu Gly Ala Arg Gly Ala Pro Gly Pro Ala
            485                 490                 495

Gly Pro Pro Gly Asp Pro Gly Leu Met Gly Glu Arg Gly Glu Asp Gly
        500                 505                 510

Pro Ala Gly Asn Gly Thr Glu Gly Phe Pro Gly Phe Pro Gly Tyr Pro
        515                 520                 525

Gly Asn Arg Gly Ala Pro Gly Ile Asn Gly Thr Lys Gly Tyr Pro Gly
        530                 535                 540

Leu Lys Gly Asp Glu Gly Glu Ala Gly Asp Pro Gly Asp Asp Asn
545                 550                 555                 560

Asp Ile Ala Pro Arg Gly Val Lys Gly Ala Lys Gly Tyr Arg Gly Pro
                565                 570                 575

Glu Gly Pro Gln Gly Pro Pro Gly His Gln Gly Pro Pro Gly Pro Asp
            580                 585                 590

Glu Cys Glu Ile Leu Asp Ile Ile Met Lys Met Cys Ser Cys Cys Glu
            595                 600                 605

Cys Lys Cys Gly Pro Ile Asp Leu Leu Phe Val Leu Asp Ser Ser Glu
        610                 615                 620

Ser Ile Gly Leu Gln Asn Phe Glu Ile Ala Lys Asp Phe Val Val Lys
625                 630                 635                 640

Val Ile Asp Arg Leu Ser Arg Asp Glu Leu Val Lys Phe Glu Pro Gly
                645                 650                 655

Gln Ser Tyr Ala Gly Val Val Gln Tyr Ser His Ser Gln Met Gln Glu
            660                 665                 670

His Val Ser Leu Arg Ser Pro Ser Ile Arg Asn Val Gln Glu Leu Lys
            675                 680                 685

Glu Ala Ile Lys Ser Leu Gln Trp Met Ala Gly Gly Thr Phe Thr Gly
```

```
                690                 695                 700
Glu Ala Leu Gln Tyr Thr Arg Asp Gln Leu Leu Pro Pro Ser Pro Asn
705                 710                 715                 720

Asn Arg Ile Ala Leu Val Ile Thr Asp Gly Arg Ser Asp Thr Gln Arg
                725                 730                 735

Asp Thr Thr Pro Leu Asn Val Leu Cys Ser Pro Gly Ile Gln Val Val
            740                 745                 750

Ser Val Gly Ile Lys Asp Val Phe Asp Phe Ile Pro Gly Ser Asp Gln
        755                 760                 765

Leu Asn Val Ile Ser Cys Gln Gly Leu Ala Pro Ser Gln Gly Arg Pro
    770                 775                 780

Gly Leu Ser Leu Val Lys Glu Asn Tyr Ala Glu Leu Leu Glu Asp Ala
785                 790                 795                 800

Phe Leu Lys Asn Val Thr Ala Gln Ile Cys Ile Asp Lys Lys Cys Pro
                805                 810                 815

Asp Tyr Thr Cys Pro Ile Thr Phe Ser Ser Pro Ala Asp Ile Thr Ile
                820                 825                 830

Leu Leu Asp Gly Ser Ala Ser Val Gly Ser His Asn Phe Asp Thr Thr
            835                 840                 845

Lys Arg Phe Ala Lys Arg Leu Ala Glu Arg Phe Leu Thr Ala Gly Arg
        850                 855                 860

Thr Asp Pro Ala His Asp Val Arg Val Ala Val Val Gln Tyr Ser Gly
865                 870                 875                 880

Thr Gly Gln Gln Arg Pro Glu Arg Ala Ser Leu Gln Phe Leu Gln Asn
                885                 890                 895

Tyr Thr Ala Leu Ala Ser Ala Val Asp Ala Met Asp Phe Ile Asn Asp
            900                 905                 910

Ala Thr Asp Val Asn Asp Ala Leu Gly Tyr Val Thr Arg Phe Tyr Arg
        915                 920                 925

Glu Ala Ser Ser Gly Ala Ala Lys Lys Arg Leu Leu Leu Phe Ser Asp
    930                 935                 940

Gly Asn Ser Gln Gly Ala Thr Pro Ala Ala Ile Glu Lys Ala Val Gln
945                 950                 955                 960

Glu Ala Gln Arg Ala Gly Ile Glu Ile Phe Val Val Val Gly Arg
                965                 970                 975

Gln Val Asn Glu Pro His Ile Arg Val Leu Val Thr Gly Lys Thr Ala
            980                 985                 990

Glu Tyr Asp Val Ala Tyr Gly Glu  Ser His Leu Phe Arg Val Pro Ser
        995                 1000                1005

Tyr Gln  Ala Leu Leu Arg Gly  Val Phe His Gln Thr  Val Ser Arg
    1010                1015                1020

Lys Val  Ala Leu Gly
    1025

<210> SEQ ID NO 63
<211> LENGTH: 1052
<212> TYPE: PRT
<213> ORGANISM: Homo sapiens

<400> SEQUENCE: 63

Met Arg Ala Ala Arg Ala Leu Leu Pro Leu Leu Leu Gln Ala Cys Trp
1               5                   10                  15

Thr Ala Ala Gln Asp Glu Pro Glu Thr Pro Arg Ala Val Ala Phe Gln
            20                  25                  30
```

```
Asp Cys Pro Val Asp Leu Phe Phe Val Leu Asp Thr Ser Glu Ser Val
         35                  40                  45

Ala Leu Arg Leu Lys Pro Tyr Gly Ala Leu Val Asp Lys Val Lys Ser
 50                  55                  60

Phe Thr Lys Arg Phe Ile Asp Asn Leu Arg Asp Arg Tyr Tyr Arg Cys
 65                  70                  75                  80

Asp Arg Asn Leu Val Trp Asn Ala Gly Ala Leu His Tyr Ser Asp Glu
                 85                  90                  95

Val Glu Ile Ile Gln Gly Leu Thr Arg Met Pro Gly Gly Arg Asp Ala
            100                 105                 110

Leu Lys Ser Ser Val Asp Ala Val Lys Tyr Phe Gly Lys Gly Thr Tyr
            115                 120                 125

Thr Asp Cys Ala Ile Lys Lys Gly Leu Glu Gln Leu Leu Val Gly Gly
        130                 135                 140

Ser His Leu Lys Glu Asn Lys Tyr Leu Ile Val Val Thr Asp Gly His
145                 150                 155                 160

Pro Leu Glu Gly Tyr Lys Glu Pro Cys Gly Gly Leu Glu Asp Ala Val
                165                 170                 175

Asn Glu Ala Lys His Leu Gly Val Lys Val Phe Ser Val Ala Ile Thr
            180                 185                 190

Pro Asp His Leu Glu Pro Arg Leu Ser Ile Ile Ala Thr Asp His Thr
        195                 200                 205

Tyr Arg Arg Asn Phe Thr Ala Ala Asp Trp Gly Gln Ser Arg Asp Ala
210                 215                 220

Glu Glu Ala Ile Ser Gln Thr Ile Asp Thr Ile Val Asp Met Ile Lys
225                 230                 235                 240

Asn Asn Val Glu Gln Val Cys Cys Ser Phe Glu Cys Gln Pro Ala Arg
                245                 250                 255

Gly Pro Pro Gly Leu Arg Gly Asp Pro Gly Phe Glu Gly Glu Arg Gly
            260                 265                 270

Lys Pro Gly Leu Pro Gly Glu Lys Gly Glu Ala Gly Asp Pro Gly Arg
        275                 280                 285

Pro Gly Asp Leu Gly Pro Val Gly Tyr Gln Gly Met Lys Gly Glu Lys
290                 295                 300

Gly Ser Arg Gly Glu Lys Thr Arg Ser Thr Ala Pro Arg Arg Pro Leu
305                 310                 315                 320

His Leu Glu Gly Gln Gly Gln Pro Pro Arg His Pro Ala Lys Gly Ser
                325                 330                 335

Arg Gly Pro Lys Gly Tyr Lys Gly Glu Lys Gly Lys Arg Gly Ile Asp
            340                 345                 350

Gly Val Asp Gly Val Lys Gly Glu Met Gly Tyr Pro Gly Leu Pro Gly
        355                 360                 365

Cys Lys Gly Ser Pro Gly Phe Asp Gly Ile Gln Gly Pro Pro Gly Pro
370                 375                 380

Lys Gly Asp Pro Gly Ala Phe Gly Leu Lys Gly Glu Lys Gly Glu Pro
385                 390                 395                 400

Gly Ala Asp Gly Glu Ala Gly Arg Pro Gly Ser Ser Gly Pro Ser Gly
                405                 410                 415

Asp Glu Gly Gln Pro Gly Glu Pro Gly Pro Gly Glu Lys Gly Glu
            420                 425                 430

Ala Gly Asp Glu Gly Asn Pro Gly Pro Asp Gly Ala Pro Gly Glu Arg
        435                 440                 445

Gly Gly Pro Gly Glu Arg Gly Pro Arg Gly Thr Pro Gly Thr Arg Gly
```

-continued

```
            450             455             460
Pro Arg Gly Asp Pro Gly Glu Ala Gly Pro Gln Gly Asp Gln Gly Arg
465             470             475             480

Glu Gly Pro Val Gly Val Pro Gly Asp Pro Gly Glu Ala Gly Pro Ile
            485             490             495

Gly Pro Lys Gly Tyr Arg Gly Asp Glu Gly Pro Pro Gly Ser Glu Gly
            500             505             510

Ala Arg Gly Ala Pro Gly Pro Ala Gly Pro Gly Asp Pro Gly Leu
        515             520             525

Met Gly Glu Arg Gly Glu Asp Gly Pro Ala Gly Asn Gly Thr Glu Gly
        530             535             540

Phe Pro Gly Phe Pro Gly Tyr Pro Gly Asn Arg Gly Ala Pro Gly Ile
545             550             555             560

Asn Gly Thr Lys Gly Tyr Pro Gly Leu Lys Gly Asp Glu Gly Glu Ala
            565             570             575

Gly Asp Pro Gly Asp Asn Asn Asp Ile Ala Pro Arg Gly Val Lys
        580             585             590

Gly Ala Lys Gly Tyr Arg Gly Pro Glu Gly Pro Gln Gly Pro Pro Gly
        595             600             605

His Gln Gly Pro Pro Gly Pro Asp Glu Cys Glu Ile Leu Asp Ile Ile
        610             615             620

Met Lys Met Cys Ser Cys Cys Glu Cys Lys Cys Gly Pro Ile Asp Leu
625             630             635             640

Leu Phe Val Leu Asp Ser Ser Glu Ser Ile Gly Leu Gln Asn Phe Glu
            645             650             655

Ile Ala Lys Asp Phe Val Val Lys Val Ile Asp Arg Leu Ser Arg Asp
            660             665             670

Glu Leu Val Lys Phe Glu Pro Gly Gln Ser Tyr Ala Gly Val Val Gln
            675             680             685

Tyr Ser His Ser Gln Met Gln Glu His Val Ser Leu Arg Ser Pro Ser
        690             695             700

Ile Arg Asn Val Gln Glu Leu Lys Glu Ala Ile Lys Ser Leu Gln Trp
705             710             715             720

Met Ala Gly Gly Thr Phe Thr Gly Glu Ala Leu Gln Tyr Thr Arg Asp
            725             730             735

Gln Leu Leu Pro Pro Ser Pro Asn Asn Arg Ile Ala Leu Val Ile Thr
            740             745             750

Asp Gly Arg Ser Asp Thr Gln Arg Asp Thr Thr Pro Leu Asn Val Leu
        755             760             765

Cys Ser Pro Gly Ile Gln Val Val Ser Val Gly Ile Lys Asp Val Phe
        770             775             780

Asp Phe Ile Pro Gly Ser Asp Gln Leu Asn Val Ile Ser Cys Gln Gly
785             790             795             800

Leu Ala Pro Ser Gln Gly Arg Pro Gly Leu Ser Leu Val Lys Glu Asn
            805             810             815

Tyr Ala Glu Leu Leu Glu Asp Ala Phe Leu Lys Asn Val Thr Ala Gln
            820             825             830

Ile Cys Ile Asp Lys Lys Cys Pro Asp Tyr Thr Cys Pro Ile Thr Phe
        835             840             845

Ser Ser Pro Ala Asp Ile Thr Ile Leu Leu Asp Gly Ser Ala Ser Val
        850             855             860

Gly Ser His Asn Phe Asp Thr Thr Lys Arg Phe Ala Lys Arg Leu Ala
865             870             875             880
```

```
Glu Arg Phe Leu Thr Ala Gly Arg Thr Asp Pro Ala His Asp Val Arg
                885                 890                 895

Val Ala Val Val Gln Tyr Ser Gly Thr Gly Gln Gln Arg Pro Glu Arg
            900                 905                 910

Ala Ser Leu Gln Phe Leu Gln Asn Tyr Thr Ala Leu Ala Ser Ala Val
        915                 920                 925

Asp Ala Met Asp Phe Ile Asn Asp Ala Thr Asp Val Asn Asp Ala Leu
    930                 935                 940

Gly Tyr Val Thr Arg Phe Tyr Arg Glu Ala Ser Ser Gly Ala Ala Lys
945                 950                 955                 960

Lys Arg Leu Leu Leu Phe Ser Asp Gly Asn Ser Gln Gly Ala Thr Pro
                965                 970                 975

Ala Ala Ile Glu Lys Ala Val Gln Glu Ala Gln Arg Ala Gly Ile Glu
            980                 985                 990

Ile Phe Val Val Val Val Gly Arg  Gln Val Asn Glu Pro  His Ile Arg
        995                 1000                1005

Val Leu Val Thr Gly Lys Thr  Ala Glu Tyr Asp Val  Ala Tyr Gly
    1010                1015                1020

Glu Ser His Leu Phe Arg Val  Pro Ser Tyr Gln Ala  Leu Leu Arg
    1025                1030                1035

Gly Val  Phe His Gln Thr Val  Ser Arg Lys Val Ala  Leu Gly
    1040                1045                1050

<210> SEQ ID NO 64
<211> LENGTH: 126
<212> TYPE: DNA
<213> ORGANISM: Homo sapiens

<400> SEQUENCE: 64
tccctgacag gagaccacgt gtcctgcaga cccgctccac cgcccctcgc cgtcccctcc      60
atctggaagg acaaggacag ccacccaggc acccagcaaa ggtgcctgtg tcactttcac     120
cccacc                                                                126
```